United States Patent
Labib et al.

(10) Patent No.: US 11,701,622 B2
(45) Date of Patent: *Jul. 18, 2023

(54) CARTRIDGES AND SYSTEMS FOR MEMBRANE-BASED THERAPIES

(71) Applicant: Novaflux Inc., Princeton, NJ (US)

(72) Inventors: Mohamed E. Labib, Princeton, NJ (US); Stanislav S. Dukhin, Goldens Bridge, NY (US); Jeffrey C. Robertson, Rochester, NY (US)

(73) Assignee: Novaflux Inc., Princeton, NJ (US)

( * ) Notice: Subject to any disclaimer, the term of this patent is extended or adjusted under 35 U.S.C. 154(b) by 84 days.

This patent is subject to a terminal disclaimer.

(21) Appl. No.: 16/556,851

(22) Filed: Aug. 30, 2019

(65) Prior Publication Data
US 2020/0129929 A1  Apr. 30, 2020

Related U.S. Application Data

(63) Continuation of application No. 15/274,279, filed on Sep. 23, 2016, now Pat. No. 10,399,040.
(Continued)

(51) Int. Cl.
*B01D 69/08* (2006.01)
*A61M 1/16* (2006.01)
(Continued)

(52) U.S. Cl.
CPC ............. *B01D 69/08* (2013.01); *A61M 1/16* (2013.01); *B01D 61/28* (2013.01); *B01D 63/02* (2013.01);
(Continued)

(58) Field of Classification Search
CPC .. A61M 1/16; A61M 1/34; A61M 2205/3334; B01D 2313/10;
(Continued)

(56) References Cited

U.S. PATENT DOCUMENTS

| 3,827,563 A | 8/1974 | Boe et al. |
| 4,038,191 A | 7/1977 | Davis et al. |

(Continued)

FOREIGN PATENT DOCUMENTS

| EP | 0 001 736 A1 | 5/1979 |
| EP | 0 167 162 A2 | 1/1986 |

(Continued)

OTHER PUBLICATIONS

Office Action for European Application No. 16774826.8 dated Oct. 6, 2020.
(Continued)

*Primary Examiner* — Pranav N Patel
(74) *Attorney, Agent, or Firm* — Merchant & Gould P.C.

(57) ABSTRACT

A cartridge is provided for dialysis or other blood processing therapy. In the cartridge, fibers may be substantially uniformly distributed near a midplane, but near an end, in the inter fiber space, there may be void flow channels, which may cause fluid flow in the inter fiber space to transition within a short region to uniform flow with minimal stagnation zones. Void flow channels may be be radially oriented, introducing fluid from the outer circumference, or axially oriented, introducing fluid along the axial direction through passageways through the potting material. The fluid flow in the inter fiber space may be perpendicular to the fibers, or radial with respect to a cartridge longitudinal axis. The cartridge may have blood flow in the inter fiber space, and flow of dialysate or ultrafiltrate in the lumens of the fibers, or the opposite situation.

15 Claims, 37 Drawing Sheets

Related U.S. Application Data

(60) Provisional application No. 62/238,214, filed on Oct. 7, 2015, provisional application No. 62/222,901, filed on Sep. 24, 2015.

(51) Int. Cl.
   *B01D 61/28* (2006.01)
   *B01D 63/02* (2006.01)
   *A61M 1/34* (2006.01)

(52) U.S. Cl.
   CPC ......... *B01D 63/022* (2013.01); *B01D 63/026* (2013.01); *A61M 1/34* (2013.01); *A61M 2205/3334* (2013.01); *B01D 2313/10* (2013.01); *B01D 2313/21* (2013.01); *B01D 2313/44* (2013.01)

(58) Field of Classification Search
   CPC ............ B01D 2313/21; B01D 2313/44; B01D 61/28; B01D 63/02; B01D 63/022; B01D 63/026; B01D 69/08; B01D 63/021; B01D 2313/08; B01D 2313/086; B01D 2313/20; B01D 2313/105; B01D 2313/12; B01D 2313/19; B01D 2313/14; B01D 2313/23; B01D 2053/224; C02F 1/44
   See application file for complete search history.

(56) References Cited

U.S. PATENT DOCUMENTS

| | | |
|---|---|---|
| 4,146,480 A | 3/1979 | Holanek et al. |
| 4,164,468 A | 8/1979 | Raible |
| 4,179,380 A | 12/1979 | Amicel et al. |
| 4,201,673 A | 5/1980 | Kanno et al. |
| 4,212,744 A | 7/1980 | Oota |
| 4,220,535 A | 9/1980 | Leonard |
| 4,271,023 A | 6/1981 | Giovannetti et al. |
| 4,346,006 A | 8/1982 | Kopp et al. |
| 4,374,088 A | 2/1983 | Stenberg et al. |
| 4,396,510 A * | 8/1983 | Hsei ............ B01D 63/02 210/321.8 |
| 4,620,965 A | 11/1986 | Fukusawa et al. |
| 4,666,603 A | 5/1987 | Madsen et al. |
| 4,707,268 A | 11/1987 | Shah et al. |
| 4,789,473 A | 12/1988 | Mathieu et al. |
| 4,861,485 A | 8/1989 | Fecondini |
| 4,906,375 A | 3/1990 | Heilmann |
| 4,921,612 A | 5/1990 | Sirkar |
| 4,929,259 A | 5/1990 | Caskey et al. |
| 4,990,251 A | 2/1991 | Spranger et al. |
| 5,037,610 A | 8/1991 | Fukusawa et al. |
| 5,072,498 A | 12/1991 | Raff et al. |
| 5,096,582 A | 3/1992 | Lombardi et al. |
| 5,106,579 A | 4/1992 | Fukazawa et al. |
| 5,139,741 A | 8/1992 | Hagiwara |
| 5,143,612 A | 9/1992 | Hamanaka et al. |
| 5,162,101 A * | 11/1992 | Cosentino ............ F28F 21/062 422/46 |
| 5,162,102 A | 11/1992 | Nogawa et al. |
| 5,188,801 A * | 2/1993 | Fini ............ B01D 63/02 128/DIG. 3 |
| 5,198,110 A | 3/1993 | Hanai et al. |
| 5,256,294 A | 10/1993 | van Reis |
| 5,522,998 A | 6/1996 | Polaschegg |
| 5,525,144 A | 6/1996 | Gollan |
| 5,578,267 A | 11/1996 | Cosentino et al. |
| 5,626,759 A | 5/1997 | Krantz et al. |
| 5,700,372 A | 12/1997 | Takesawa et al. |
| 5,730,712 A | 3/1998 | Falkvall et al. |
| 5,779,897 A | 7/1998 | Kalthod et al. |
| 5,833,896 A | 11/1998 | Jacobs et al. |
| 5,871,693 A | 2/1999 | Lindsay |
| 5,882,516 A | 3/1999 | Gross et al. |
| 5,942,112 A | 8/1999 | Ishak |
| 6,074,559 A | 6/2000 | Hahmann et al. |
| 6,149,817 A | 11/2000 | Peterson et al. |
| 6,264,627 B1 | 7/2001 | Liska et al. |
| 6,346,090 B1 | 2/2002 | Liska et al. |
| 6,368,557 B1 | 4/2002 | Piplani et al. |
| 6,432,309 B1 | 8/2002 | Fuke et al. |
| 6,478,969 B2 | 11/2002 | Brantley et al. |
| 6,495,101 B1 | 12/2002 | Yokoyama et al. |
| 6,555,006 B2 | 4/2003 | van Reis |
| 6,596,167 B2 | 7/2003 | Ji et al. |
| 6,613,279 B1 | 9/2003 | Elgas et al. |
| 6,623,441 B1 | 9/2003 | Kihara et al. |
| 6,623,638 B2 | 9/2003 | Watkins et al. |
| 6,638,477 B1 | 10/2003 | Treu et al. |
| 6,719,907 B2 | 4/2004 | Collins et al. |
| 6,764,761 B2 | 7/2004 | Eu et al. |
| 6,811,542 B2 | 11/2004 | Liska et al. |
| 6,890,315 B1 | 5/2005 | Levin et al. |
| 6,994,824 B2 | 2/2006 | Mochizuki et al. |
| 7,128,837 B2 | 10/2006 | Behrendt et al. |
| 7,250,108 B2 | 7/2007 | Boivin et al. |
| 7,267,658 B2 | 9/2007 | Treu et al. |
| 7,285,106 B2 | 10/2007 | Collins et al. |
| 7,316,780 B1 | 1/2008 | Fendya et al. |
| 7,335,334 B2 | 2/2008 | Olsen et al. |
| 7,410,582 B2 | 8/2008 | Bernard et al. |
| 7,537,701 B2 | 5/2009 | Mahendran et al. |
| 7,585,412 B2 | 9/2009 | Gorsuch |
| 7,713,412 B2 | 5/2010 | Heilmann et al. |
| 7,776,219 B2 | 8/2010 | Brugger et al. |
| 7,790,029 B2 | 9/2010 | Dannenmaier et al. |
| 8,136,675 B2 | 3/2012 | Buck |
| 8,182,686 B2 | 5/2012 | Witthaus et al. |
| 8,187,410 B2 | 5/2012 | Noh et al. |
| 8,202,428 B2 | 6/2012 | Heilmann et al. |
| 8,229,546 B2 | 7/2012 | Falken et al. |
| 8,246,826 B2 | 8/2012 | Wilt et al. |
| 8,343,347 B2 | 1/2013 | Collins et al. |
| 8,387,804 B2 | 3/2013 | Buck et al. |
| 8,394,049 B2 | 3/2013 | Reggiani et al. |
| 8,430,832 B2 | 4/2013 | Humes et al. |
| 8,444,587 B2 | 5/2013 | Kelly et al. |
| 8,496,826 B2 | 7/2013 | Uchi et al. |
| 8,596,467 B2 | 12/2013 | Krause |
| 8,603,021 B2 | 12/2013 | Levin et al. |
| 8,747,980 B2 | 6/2014 | Bikson et al. |
| 8,795,220 B2 | 8/2014 | Reggiani et al. |
| 8,834,780 B2 | 9/2014 | Ying |
| 8,877,062 B2 | 11/2014 | Mullick et al. |
| 8,883,008 B2 | 11/2014 | Mishkin |
| 8,992,463 B2 | 3/2015 | Hogard et al. |
| 9,005,152 B2 | 4/2015 | Kelly et al. |
| 9,216,246 B2 | 12/2015 | Kelly et al. |
| 9,248,409 B2 | 2/2016 | Noh et al. |
| 9,254,464 B2 | 2/2016 | Keller et al. |
| 9,352,283 B2 | 5/2016 | Ying et al. |
| 10,369,263 B2 | 8/2019 | Labib et al. |
| 10,399,040 B2 | 9/2019 | Labib et al. |
| 10,426,884 B2 | 10/2019 | Labib et al. |
| 2001/0037964 A1 | 11/2001 | Won et al. |
| 2002/0091350 A1 | 7/2002 | Belson |
| 2002/0103453 A1 | 8/2002 | Burbank et al. |
| 2002/0190000 A1 | 12/2002 | Baurmeister |
| 2002/0195390 A1 | 12/2002 | Zha et al. |
| 2003/0075498 A1 | 4/2003 | Watkins et al. |
| 2006/0041216 A1 | 2/2006 | McLaughlin et al. |
| 2006/0243653 A1 | 11/2006 | Heinrich et al. |
| 2007/0007193 A1 | 1/2007 | Uchi et al. |
| 2007/0107884 A1 | 5/2007 | Sirkar et al. |
| 2007/0119781 A1 | 5/2007 | Huang et al. |
| 2009/0004053 A1 | 1/2009 | Kenley |
| 2009/0124963 A1 | 5/2009 | Hogard et al. |
| 2009/0218274 A1 | 9/2009 | Sakashita et al. |
| 2009/0234266 A1 | 9/2009 | Solomon et al. |
| 2009/0321344 A1 | 12/2009 | Lee et al. |
| 2010/0000936 A1 | 1/2010 | Osabe et al. |
| 2010/0089817 A1 | 4/2010 | Heilmann et al. |
| 2010/0125235 A1 | 5/2010 | Cauley, III et al. |
| 2011/0011786 A1 | 1/2011 | Feichtner et al. |

(56) References Cited

U.S. PATENT DOCUMENTS

| | | |
|---|---|---|
| 2012/0043271 A1 | 2/2012 | Maurer |
| 2012/0234746 A1 | 9/2012 | Howard et al. |
| 2012/0318727 A1 | 12/2012 | Kawatani et al. |
| 2013/0094997 A1 | 4/2013 | Wang et al. |
| 2014/0158605 A1 | 6/2014 | Mishkin |
| 2014/0208948 A1 | 7/2014 | Cao |
| 2015/0314057 A1 | 11/2015 | Labib et al. |
| 2016/0051936 A1* | 2/2016 | Kim .................. B01D 63/02 210/636 |
| 2016/0129172 A1 | 5/2016 | Hornung et al. |
| 2016/0375188 A1 | 12/2016 | Labib et al. |
| 2017/0106341 A1 | 4/2017 | Labib et al. |
| 2020/0061274 A1 | 2/2020 | Labib et al. |
| 2020/0197595 A1 | 6/2020 | Labib et al. |

FOREIGN PATENT DOCUMENTS

| | | |
|---|---|---|
| EP | 0 217 759 A1 | 4/1987 |
| EP | 1 634 639 A1 | 3/2006 |
| EP | 1 790 364 A1 | 5/2007 |
| EP | 1 964 603 A1 | 9/2008 |
| EP | 2 083 939 B1 | 11/2010 |
| EP | 2 659 914 A1 | 11/2013 |
| EP | 2 796 185 A1 | 10/2014 |
| JP | 53-30990 | 3/1978 |
| JP | 56-100605 | 8/1981 |
| JP | 2006088148 A | 4/2006 |
| WO | WO 2004056460 | 7/2004 |
| WO | WO 2008/088293 A1 | 7/2008 |
| WO | WO 2010/128044 A1 | 11/2010 |
| WO | WO 2011/032154 A1 | 3/2011 |
| WO | WO 2011/105495 A1 | 9/2011 |
| WO | WO 2013/094533 A1 | 6/2013 |
| WO | WO 2015/118046 A1 | 8/2015 |
| WO | WO 2015/153370 A2 | 10/2015 |
| WO | WO 2017/048224 A1 | 3/2017 |
| WO | WO 2017/053805 A1 | 3/2017 |

OTHER PUBLICATIONS

Ayaka Hirano et al., "Experimental evaluation of flow and dialysis performance of hollow-fiber dialyzers with different packing densities," Journal of Artificial Organs, vol. 15, pp. 168-17 (2012).
C. Ronco et al., "Dialysate flow distribution in hollow fiber hemodialyzers with different dialysate pathway configurations," The International Journal of Artificial Organs, vol. 23, No. 9, pp. 601-609 (2000).
Churn K. Poh et al., "Effect of Flow Baffles on the Dialysate Flow Distribution of Hollow-Fiber Hemodialyzers: A Nonintrusive Experimental Sstudy Using MRI," Journal of Biomechanical Engineering, Transactions of the ASME, vol. 125, pp. 481-489 (Aug. 2003).
Churn K. Poh et al., "Effect of Spacer Yarns on the Dialysate Flow Distribution of Hemodialysers: A Magnetic Resonance Imaging Study," ASAIO Journal, vol. 49, pp. 440-448 (2003).
Claudio Ronco et al., "Flow distribution analysis by helical scanning in polysulfone hemodialyzers: Effects of fiber structure and design on flow pattersn and solute clearnaces," Hemodialysis International, vol. 10, pp. 380-388 (2006).
Claudio Ronco, "Fluid Mechanics and Crossfiltration in Hollow-Fiber Hemodialyzers," Contributions to Nephrology, vol. 158, pp. 34-49 (2007).
Dukhin et al., "Outside-in hemofiltration for prolonged operation without clogging," Journal of Membrane Science, vol. 464, pp. 173-178 (2014).
Fealy et al., "The Effect of Circuit "Down-Time" on Uraemic Control During Continuous Veno-Venous Haemoflitration," Critical Care and Resuscitation, vol. 4, pp. 266-270 (2002).
Feng Ding et al., "A Biomimetic Membrane Device That Modulates the Excessive Inflammatory Response to Sepsis," PLoS One, vol. 6, Issue 4, e18584, pp. 1-14 (Apr. 2011)

Feng Shen et al., "Threshold Response of Initiation of Blood Coagulation by Tissue Factor in Patterned Microfluidic Capillaries is Controlled by Shear Rate," Arteriosclerosis, Thrombosis, and Vascular Biology, vol. 28, pp. 2035-2041 (2008) and Supp.
Frank Lipnizki et al., "Mass transfer performance for hollow fibre modules with shell-side axial feed flow: using an engineering approach to develop a framework," Journal of Membrane Science, vol. 193, pp. 195-208 (2001).
Grudtner et al., "Histological analysis of cobalt-chromium stents with and without Camouflage polymer coating: experimental porcine carotid artery model," Vascular, vol. 19, No. 2, pp. 89-96 (2011).
Hashimoto et al., "Effect of Shear Rate on Clot Growth at Foreign Surfaces," Artificial Organs, Abstract (Nov. 1985).
Horng-Ruey Chua et al., "Circuit lifespan during continuous renal replacement therapy for combined liver and kidney failure," Journal of Critical Care, vol. 27, pp. 744.e7-744.e15 (2012).
Search Report for PCT/US2016/053452 dated Dec. 23, 2016.
International Search Report and Written Opinion for Application No. PCT/US2016/053452 dated Feb. 14, 2017.
Jasmin Wu et al., "Shell-side mass transfer performance of randomly packed hollow fiber modules," Journal of Membrane Science, vol. 172, pp. 59-74 (2000).
John K. Leypoldt et al., "Hollow Fiber Shape Alters Solute Clearances in High Flux Hemodialyzers," ASAIO Journal, vol. 49, pp. 81-87 (2003).
Ken-ichiro Yamamoto et al., "Computational Evaluation of Dialysis Fluid Flow in Dialyzers With Variously Designed Jackets," Artificial Organs, vol. 33, No. 6, pp. 481-486 (2009).
Linneweber et al., "The effect of surface roughness on activation of the coagulation system and platelet adhesion in rotary blood pumps," Artif Organs, vol. 31, No. 5, Abstract (May 2007).
Isao Noda et al., "Effect of Flow Maldistribution on Hollow Fiber Dialysis—Experimental Studies," Journal of Membrane Science, vol. 5, pp. 209-225 (1979).
M.J. Costello et al., "The effect of shell side hydrodynamics on the performance of axial flow hollow fitbre modules," Journal of Membrane Science, vol. 80, pp. 1-11 (1993).
Norfamilabinti Che Mat et al., "Hollow fiber membrane modules," Current Opinion in Chemical Engineering, vol. 4, pp. 18-24 (2014).
P.W.T. Dierickx et al., "Blood flow around hollow fibers," The International Journal of Artificial Organs, vol. 23, No. 9, pp. 610-617 (2000)
ReNews® a publication on dialyzer reprocessing, vol. 13, Downloaded from http://www.medivators.com/renal/renews/, pp. 1-4 (2008).
Richard A. Ward et al., "Dialysate Flow Rate and Delivered Kt/Vurea for Dialyzers with Enhanced Dialysate Flow Distribution," Clinical Journal of the American Society of Nephrology, vol. 6, pp. 2235-2239 (2011).
Runolfur et al., "Regional citrate anticoagulation in continuous venovenous hemofiltration in critically ill patients with a high risk of bleeding," Kidney International, vol. 55, pp. 1991-1997 (1999).
Uchino et al., "Continuous is not continuous: the incidence and impact of circuit "down-time" on uraemic control during continuous veno-venous haemofiltration," Intensive Care Med, vol. 29, pp. 575-578 (2003).
William R. Clark et al., "Solute Removal by Hollow-Fiber Dialyzers," Contributions to Nephrology, vol. 158, pp. 20-33 (2007).
Yujun Wang et al., "Effect of random packing on shell-side flow and mass transfer in hollow fiber module described by normal distribution function," Journal of Membrane Science, vol. 216, pp. 81-93 (2003).
Zumoff, Rebecca, "Creating a Wearable Artificial Kidney: A Difficult But Necessary Goal," Nephrology News & Issues, https://www.nephrologynews.com/the-wearable-artificial-kidney-a-difficult-but-necessary-goal/, 7 pages (Apr. 21, 2017).
Office Action for European Application No. 16774826.8 dated Feb. 19, 2020.
Exhibit A—Pending claims for U.S. Appl. No. 16/460,643.
Exhibit B—Pending claims for U.S. Appl. No. 16/583,612.
Zhang et al., "Preparation of Polyvinylidene Fluoride (PVDF) Hollow Fiber Hemodialysis Membranes," Membranes 2014, 4, 81-95.

(56) References Cited

OTHER PUBLICATIONS

Kim, Fabrication of polyacrylonitrile hollow fiber membranes from ionic liquid solutions, Polymer Chemistry, Dec. 2015; https://www.researchgate.net/pubication/283244065.

* cited by examiner

CARTRIDGES AND SYSTEMS FOR MEMBRANE-BASED THERAPIES

CROSS-REFERENCE TO RELATED APPLICATION

The present application is a continuation of U.S. application Ser. No. 15/274,279 that was filed with the United States Patent and Trademark Office on Sep. 23, 2016, and that granted as U.S. Pat. No. 10,399,040 on Sep. 3, 2019. U.S. application Ser. No. 15/274,279 includes the disclosure of U.S. provisional Ser. No. 62/222,901 that was filed with the United States Patent and Trademark Office on Sep. 24, 2015, and U.S. provisional Ser. No. 62/238,214 that was filed on Oct. 7, 2015. A priority right is claimed to U.S. application Ser. No. 15/274,279, U.S. provisional application Ser. No. 62/222,901, and U.S. provisional application Ser. No. 62/238,214, to the extent appropriate. The complete disclosures of U.S. application Ser. No. 15/274,279, U.S. provisional Ser. No. 62/222,901, and U.S. provisional Ser. No. 62/238,214 are incorporated herein by reference.

FIELD OF THE INVENTION

Embodiments of the invention pertain to hemodialysis and related therapies and processes, and pertain to cartridges and filters to perform such therapies and processes.

BACKGROUND OF THE INVENTION

Hemodialysis and related processes are used to treat large numbers of patients suffering from renal failure and other conditions, including both acute and chronic conditions. However, improvement is still needed in, among other features, the length of time that an individual filter cartridge can be used without suffering from clot formation and filter clogging. There also is a need, for whatever fluid is flowing in the inter fiber space, for more uniform flow distribution in the inter fiber space, with stagnation regions being either non-existent or as small as possible.

SUMMARY OF THE INVENTION

In an embodiment of the invention, there may be provided: a cartridge for processing a fluid, the cartridge comprising: a housing that is generally tubular, having a housing wall and having a midplane; a plurality of fibers, at least some of the fibers being hollow and having porous walls or a semipermeable membrane, at least portions of the fibers being contained within the housing, the fibers being potted near their ends in a potting material, wherein the plurality of fibers are arranged as a fiber bundle of fibers that are generally parallel to each other at least at the midplane, the fibers in the fiber bundle having an average fiber-centerline-to-fiber-centerline spacing at the midplane, wherein, adjacent to the potting material, the fiber region contains at least one void flow channel that is substantially open and has a transverse dimension that is at least 3 times the average fiber-centerline-to-fiber-centerline spacing at a midplane of the cartridge, wherein the void flow channel adjoins an outer circumference of the fiber bundle and extends inward to a radially more inward location.

It is possible that the pattern of the void flow channel can be observed on the cut and polished end of the potting material. The pattern of the void flow channel can be observed on the surface of the potting that faces the inter fiber space. The void flow channels may comprise two different sizes of void flow channels, which may alternate with each other proceeding around the circumference of the fiber bundle. The void flow channels may be distributed at equiangular locations around the perimeter of the fiber bundle. The cartridge can include fanning of the fibers near the end of the cartridge, such as by virtue of a tapered internal surface of the housing. The geometry of the cartridge may be such that there is a midplane porosity fraction, and the geometric fanning factor and the porosity fraction increase upon getting closer to the end of the cartridge. The housing internal taper that helps to produce fanning may begin closer to the midplane of the cartridge than the potting tool fingers are located during manufacture. In this situation, the porosity of the fiber bundle may be calculated as the porosity of the fiber bundle excluding the void flow channel(s), i.e., a void-adjusted porosity. The void-adjusted porosity may increase continuously toward the end of the cartridge. The void-adjusted porosity may be larger immediately next to the potting material than it is anywhere else between the midplane and that end.

In an embodiment of the invention, there may be provided: a cartridge for processing a fluid, the cartridge comprising: a housing that is generally tubular, having a housing wall; a plurality of fibers, at least some of the fibers being hollow and having porous walls or a semipermeable membrane, at least portions of the fibers being contained within the housing, wherein the plurality of fibers are arranged as a bundle of fibers that are generally parallel to each other at a cartridge midplane, the fibers in the bundle having an average fiber-centerline-to-fiber-centerline spacing at the cartridge midplane, wherein, near an end of the cartridge, the fiber region contains at least one void flow channel that is substantially open and has a transverse dimension that is at least 3 times the average fiber-centerline-to-fiber-centerline spacing at a midplane of the cartridge, wherein the cartridge has a potted region that adjoins ends of the fibers, and a supply passageway extends through the potted region from an outward-facing surface of the potted region to an opposed inward-facing surface of the potted region and is in fluid communication with the void flow channel.

In an embodiment of the invention, there may be provided: a cartridge for processing a fluid, the cartridge comprising: a housing, having a housing wall; a plurality of fibers, at least some of the fibers being hollow and having porous walls or a semipermeable membrane, at least portions of the fibers being contained within the housing, wherein the plurality of fibers are arranged as a bundle of fibers that are generally parallel to each other, wherein blood flows over the exterior surfaces of the fibers in a direction substantially perpendicular to the fiber axis, wherein fluid in an inter fiber space flows perpendicular to the fibers and generally parallel to a surface of the housing.

In an embodiment of the invention, there may be provided: a cartridge for processing a fluid, the cartridge comprising: a housing, having a housing wall; a plurality of fibers, at least some of the fibers being hollow and having porous walls or a semipermeable membrane, at least portions of the fibers being contained within the housing, wherein the plurality of fibers are arranged as a bundle of fibers that are generally parallel to each other, wherein fluid in the inter fiber space flows perpendicular to the fibers and generally radially with respect to a longitudinal axis of the cartridge.

BRIEF DESCRIPTION OF THE ILLUSTRATIONS

Embodiments of the invention are further described but are in no way limited by the following illustrations.

In FIG. 12D, eight such voids are shown.

Figure 14:
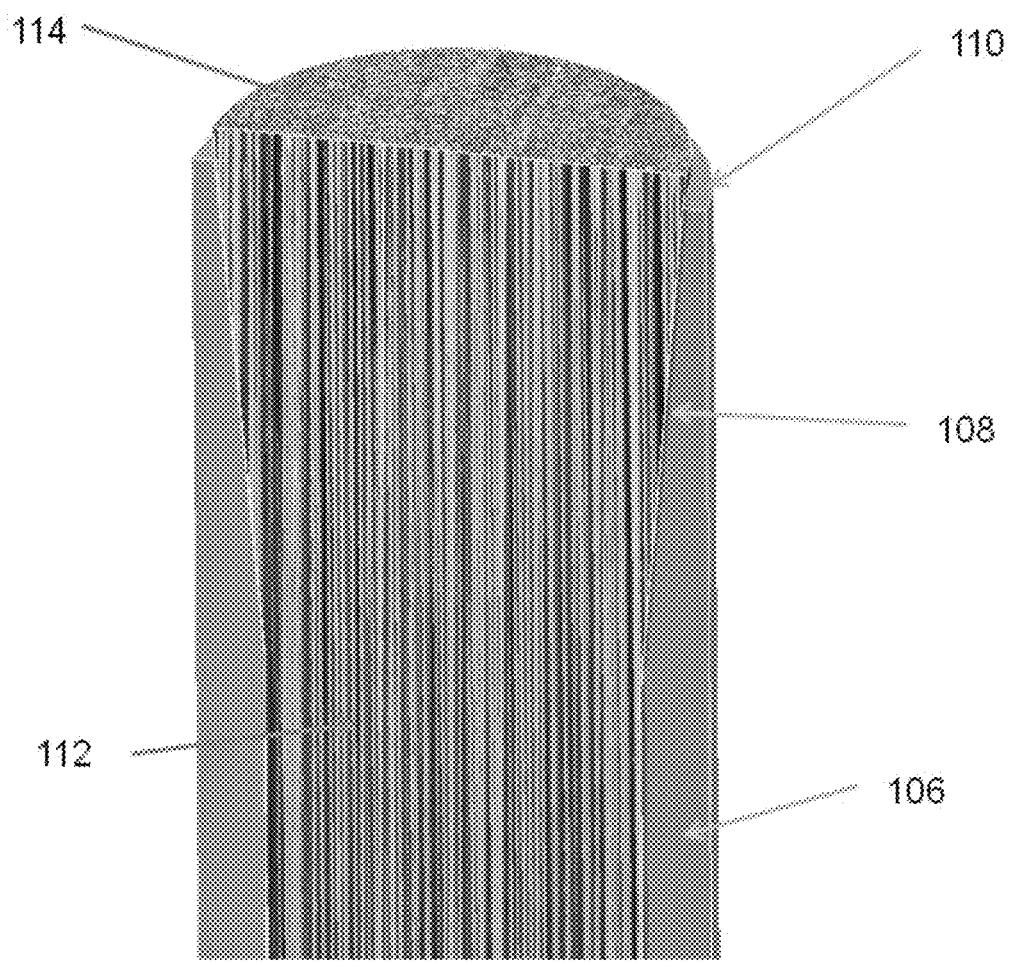

FIG. 14, for a second embodiment, is an oblique partial cross-sectional view of a housing containing a fiber bundle.

Figure 15:
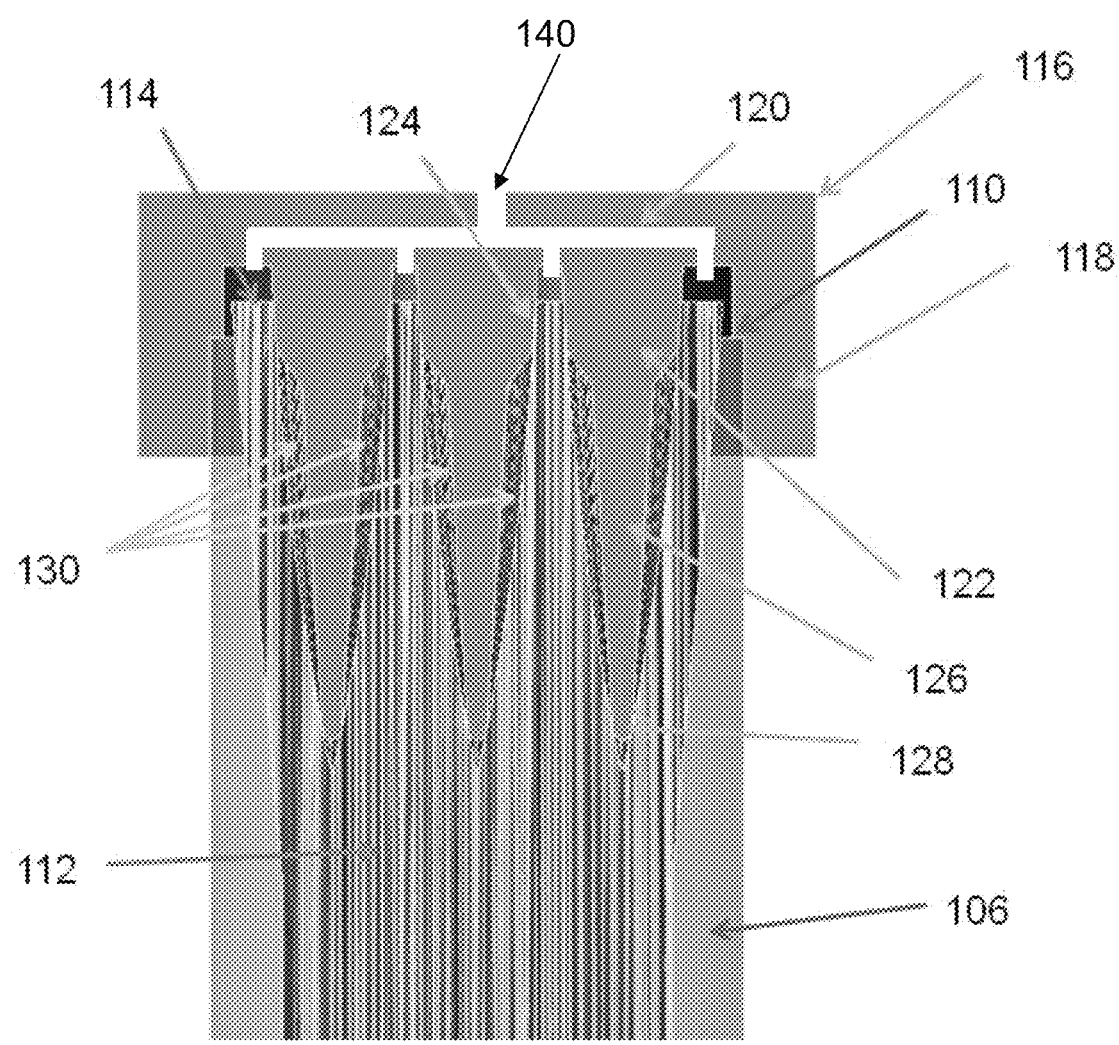

FIG. 15 is a front partial cross-sectional view of the housing of FIG. 14, with a potting cap applied.

Figure 16:
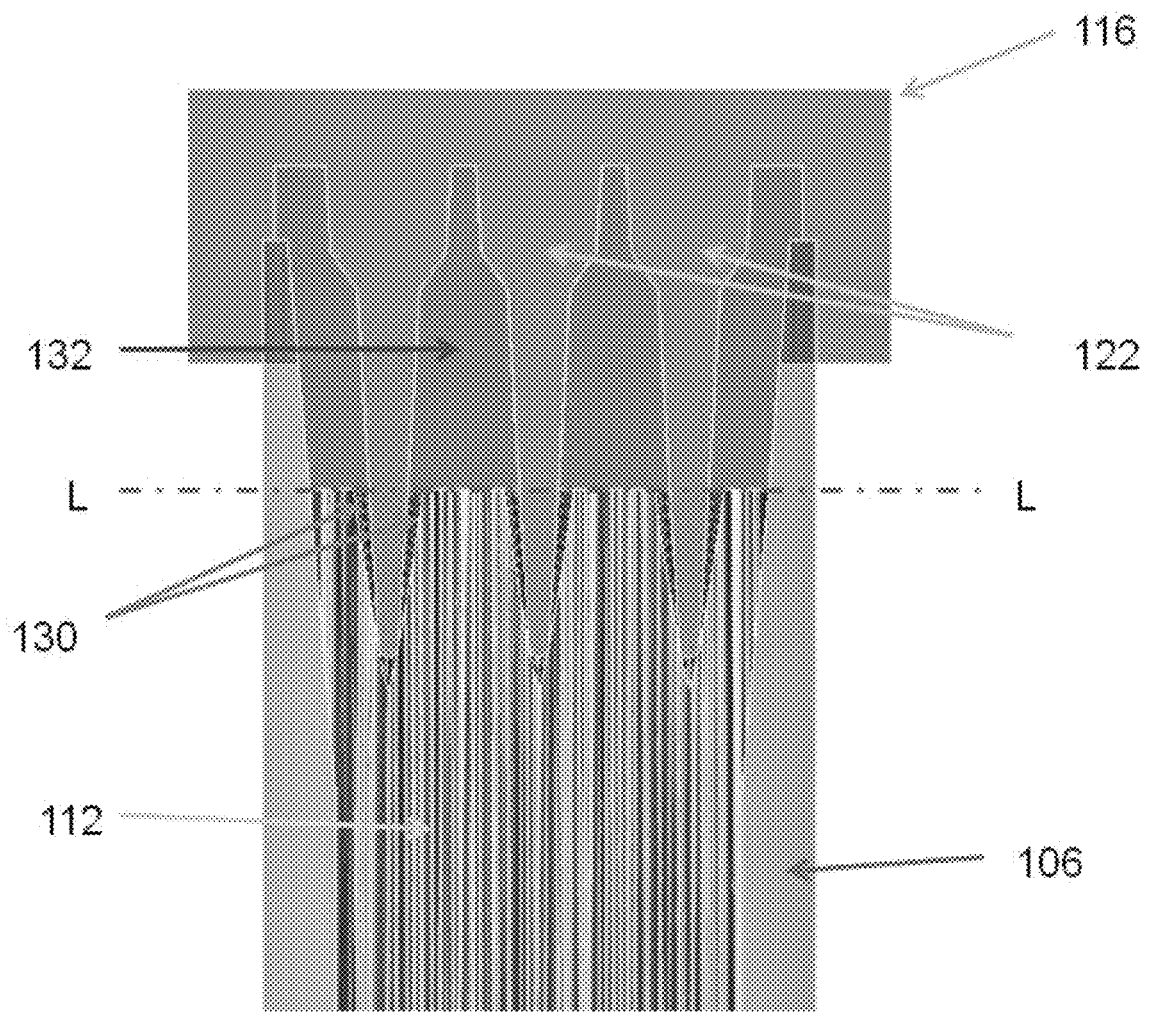

FIG. 16 is a front partial cross-sectional view of the housing and potting cap of FIG. 15, with potting material injected.

Figure 17A:
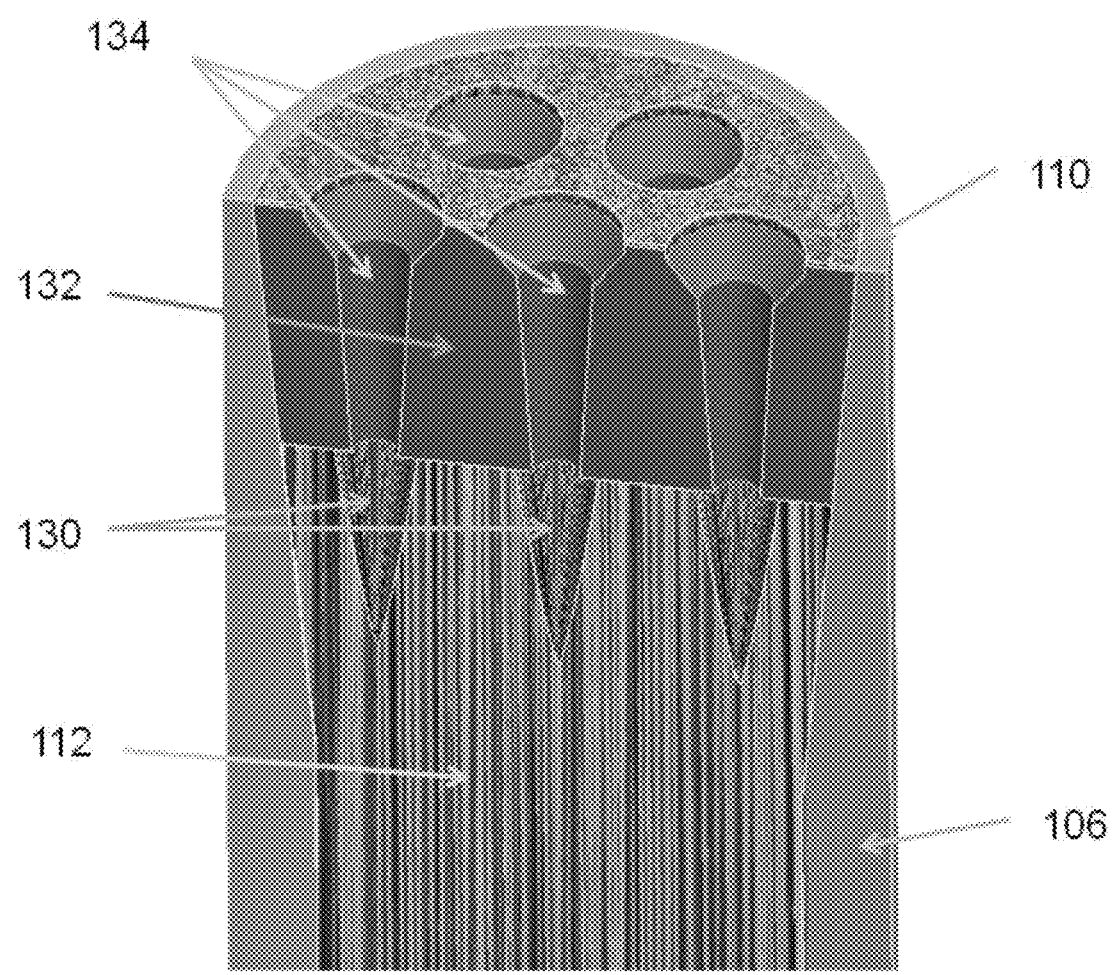

FIG. 17A is an oblique partial cross-sectional view of the filter assemblage of FIG. 16, with the potting cap removed, and the excess potting material and the fiber bundle cut back.

Figure 17B:
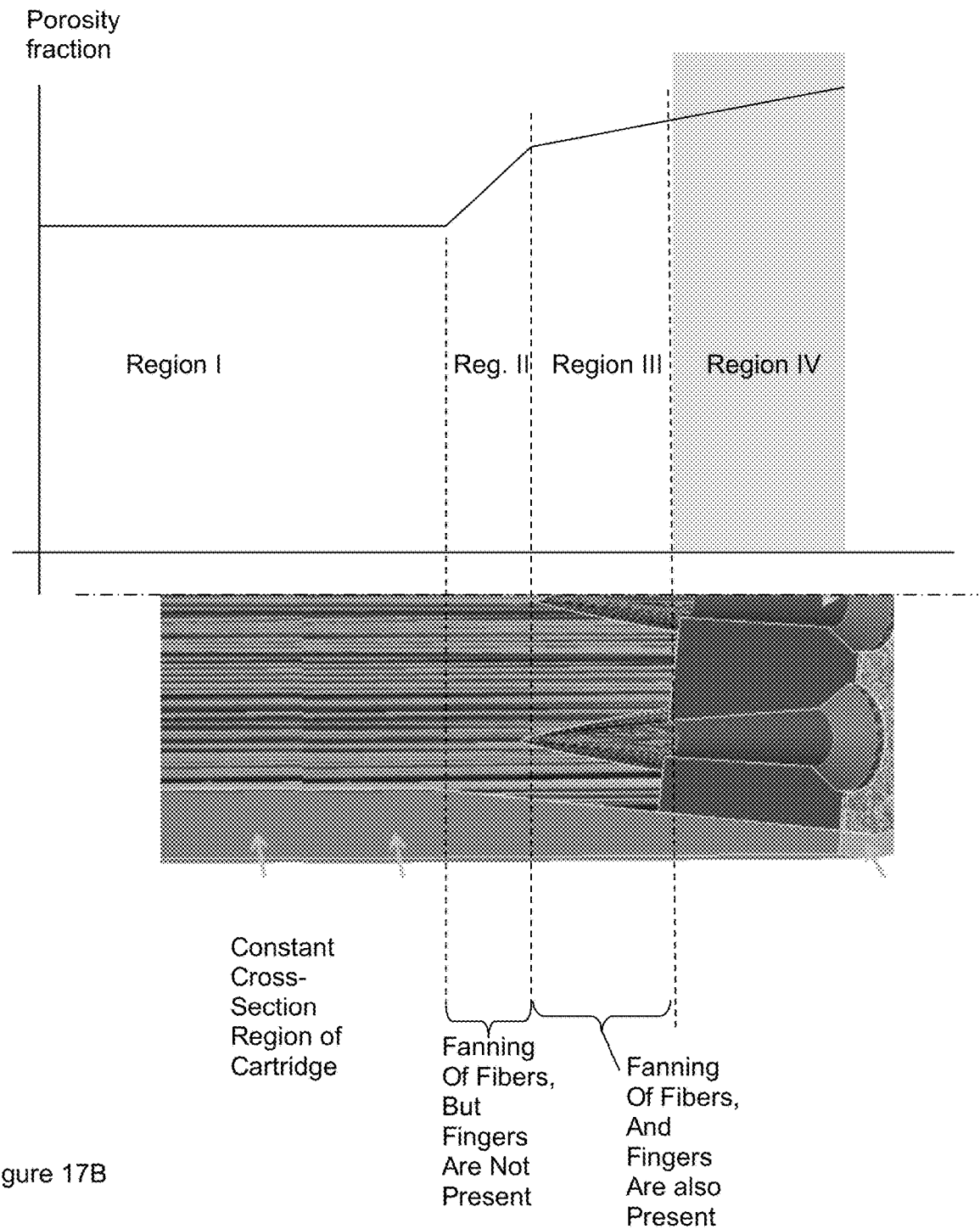

FIG. 17B is an illustration showing how the local fiber porosity could vary as a function of position along the longitudinal axis of the cartridge, taking into account both fanning of fibers and fiber rearrangement caused by the potting tool fingers.

Figure 18:
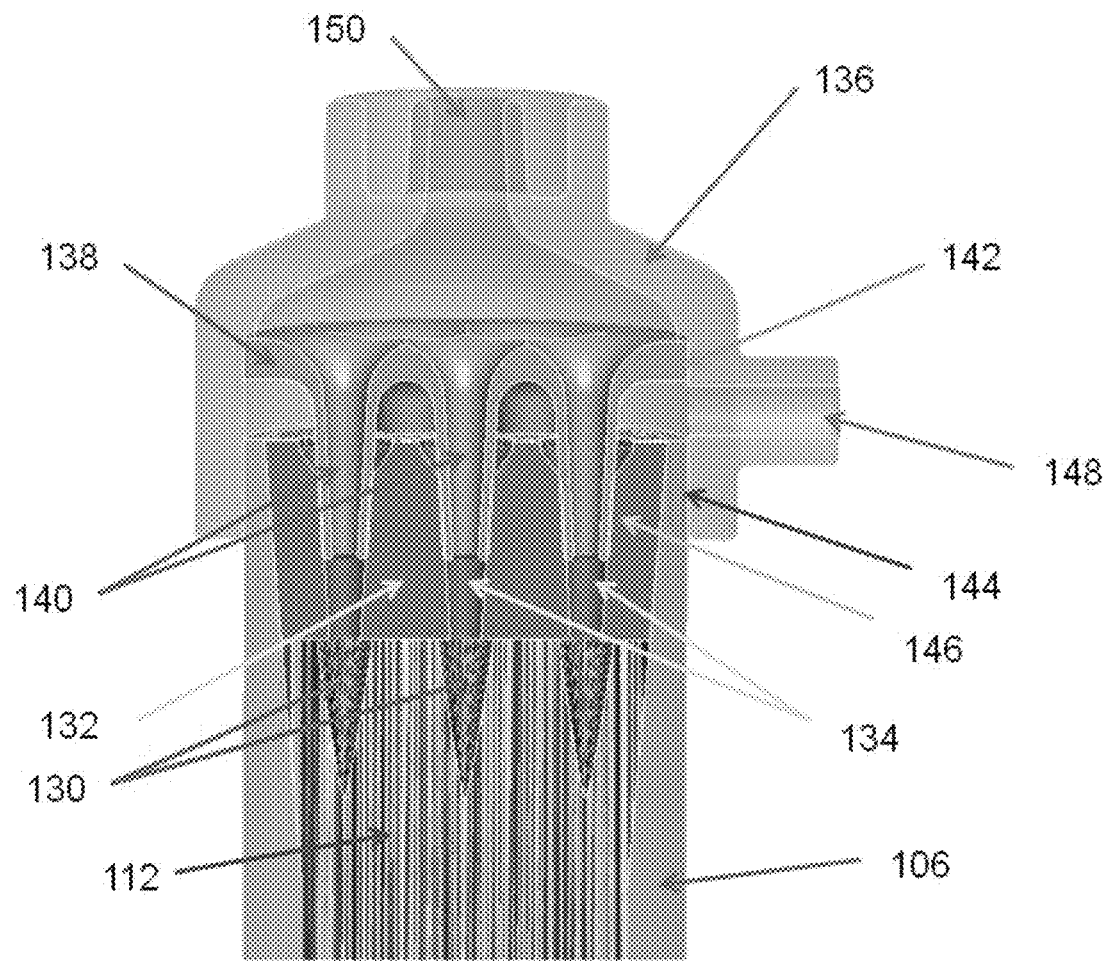

FIG. 18 is a partial front cross-sectional view of the completed filter of the second embodiment.

Figure 19:
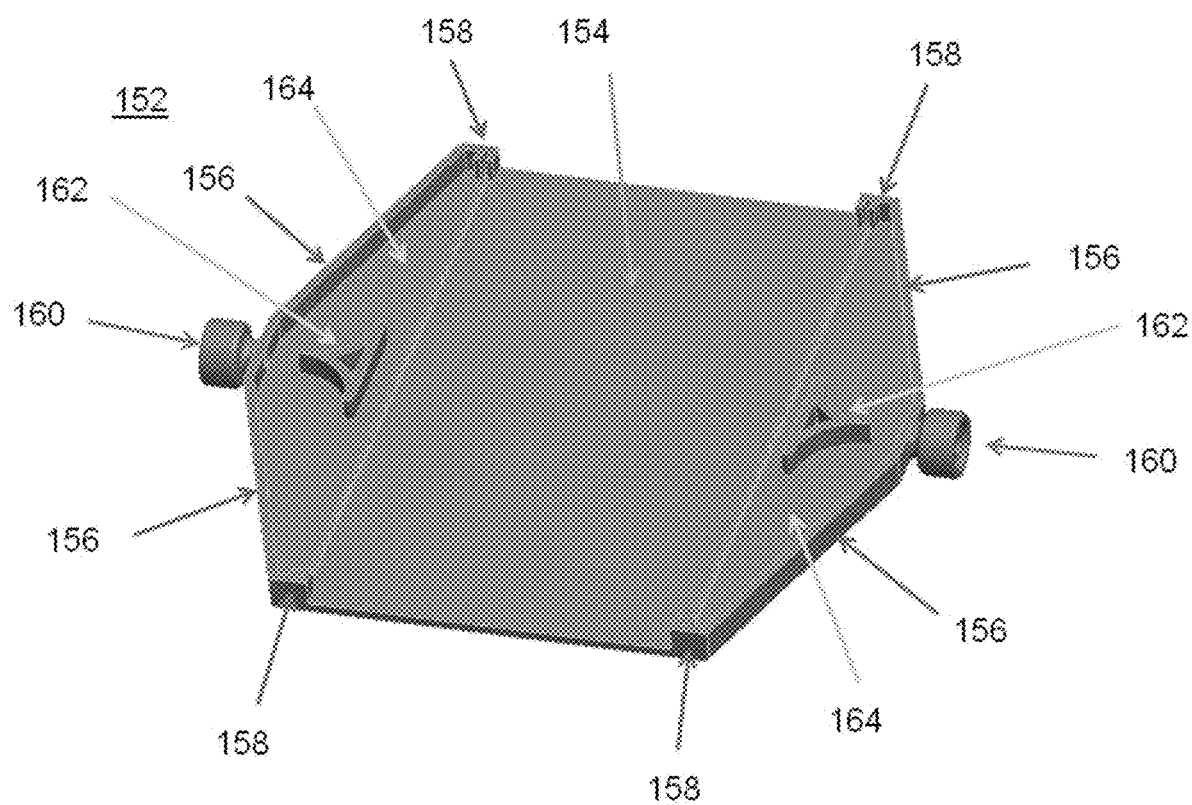

FIG. 19 is an oblique view of a filter base for a flat cross-flow filter of a third embodiment of the invention.

Figure 20:
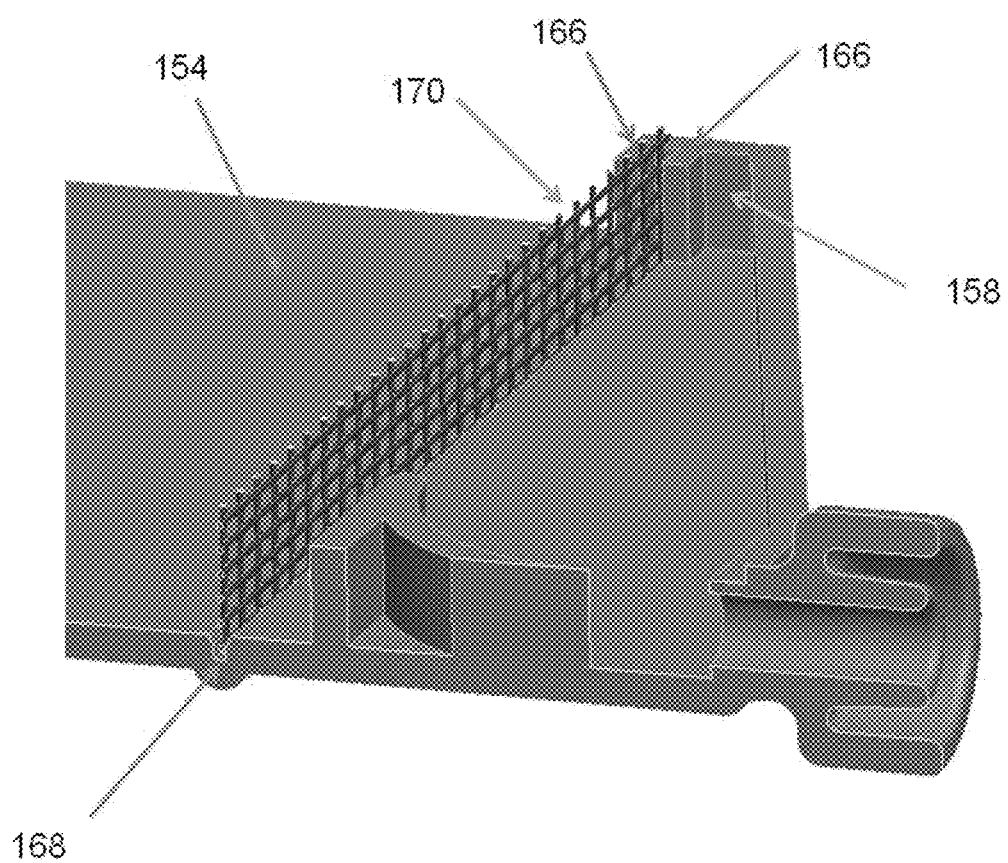

FIG. 20 is an oblique partial cross-sectional view of the filter base of FIG. 19, with a screen installed.

Figure 21:
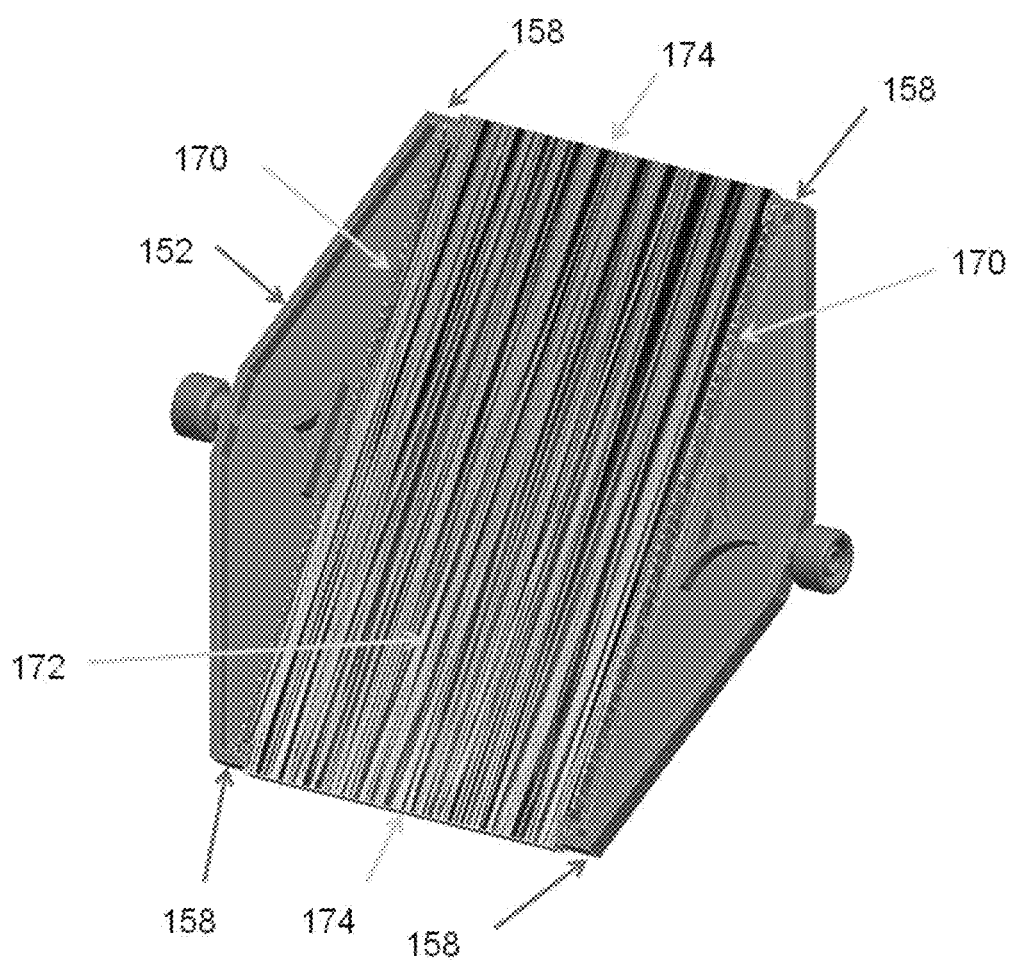

FIG. 21 is an oblique view of the filter base of FIG. 19, with screens and fiber bundle installed.

Figure 22:
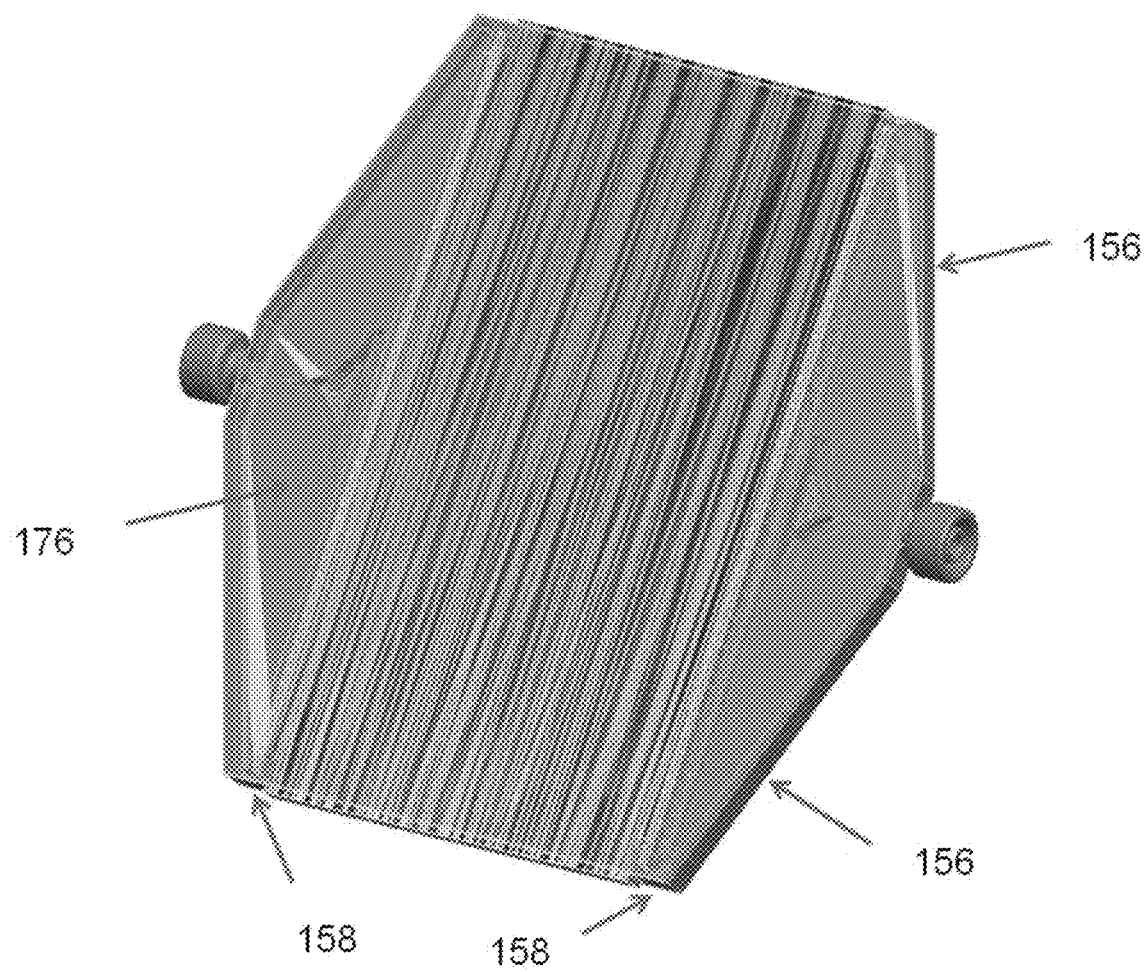

FIG. 22 is an oblique view of the filter assemblage of FIG. 21, with cover installed.

Figure 23:
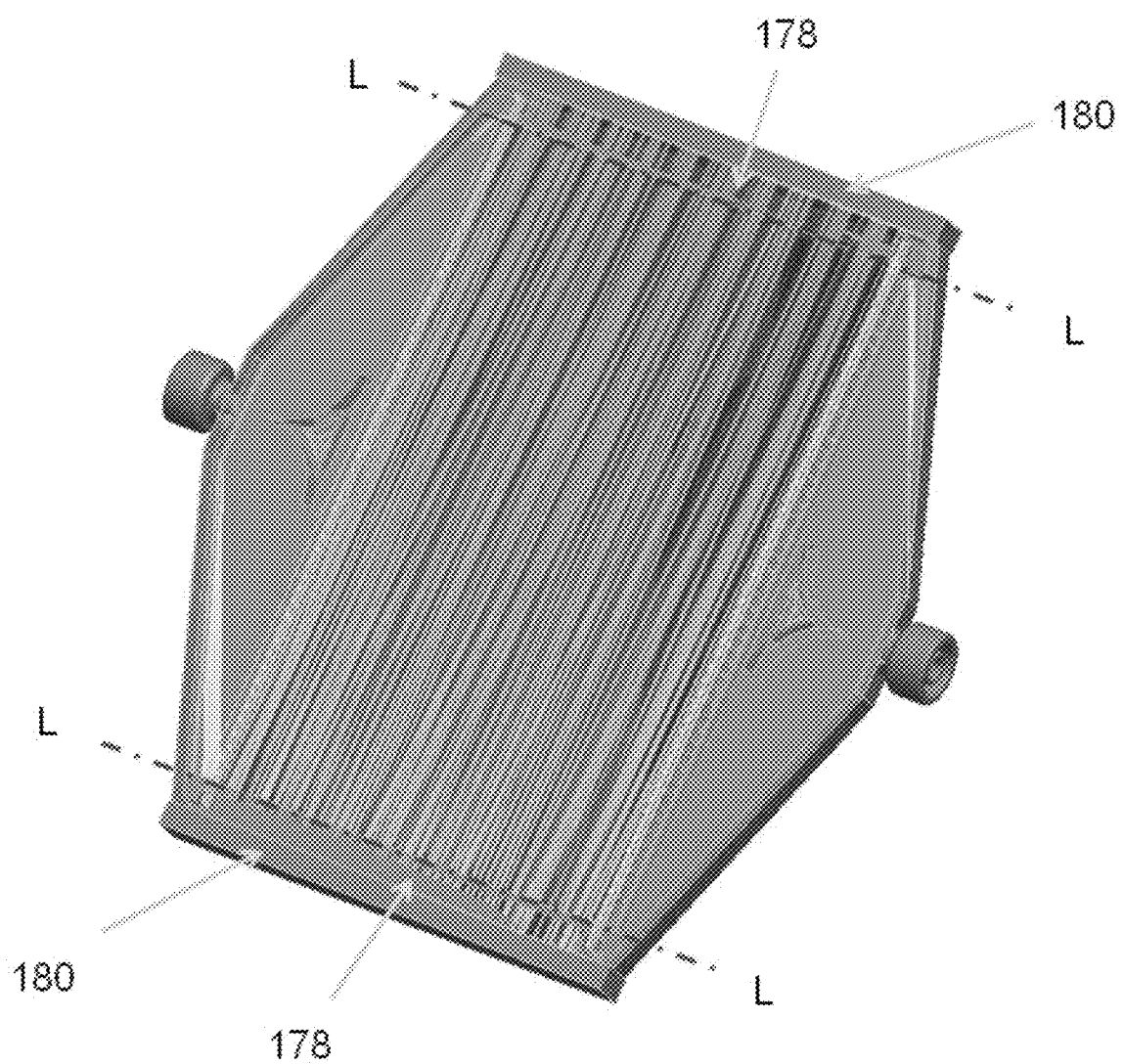

FIG. 23 is an oblique view of the filter assemblage of FIG. 22, after potting.

Figure 24:
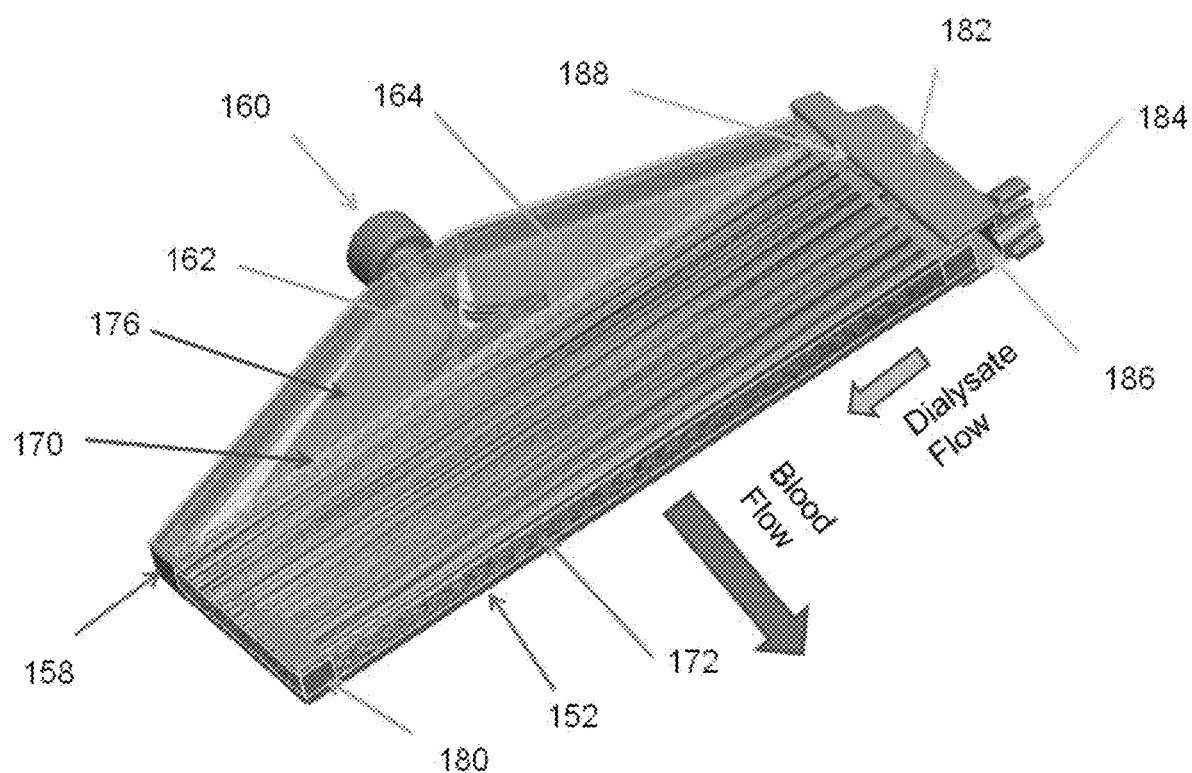

FIG. 24 is an oblique cross-sectional view of the filter assemblage of FIG. 23, with potting and fiber ends trimmed, illustrated with one dialysate cap in place.

Figure 25:
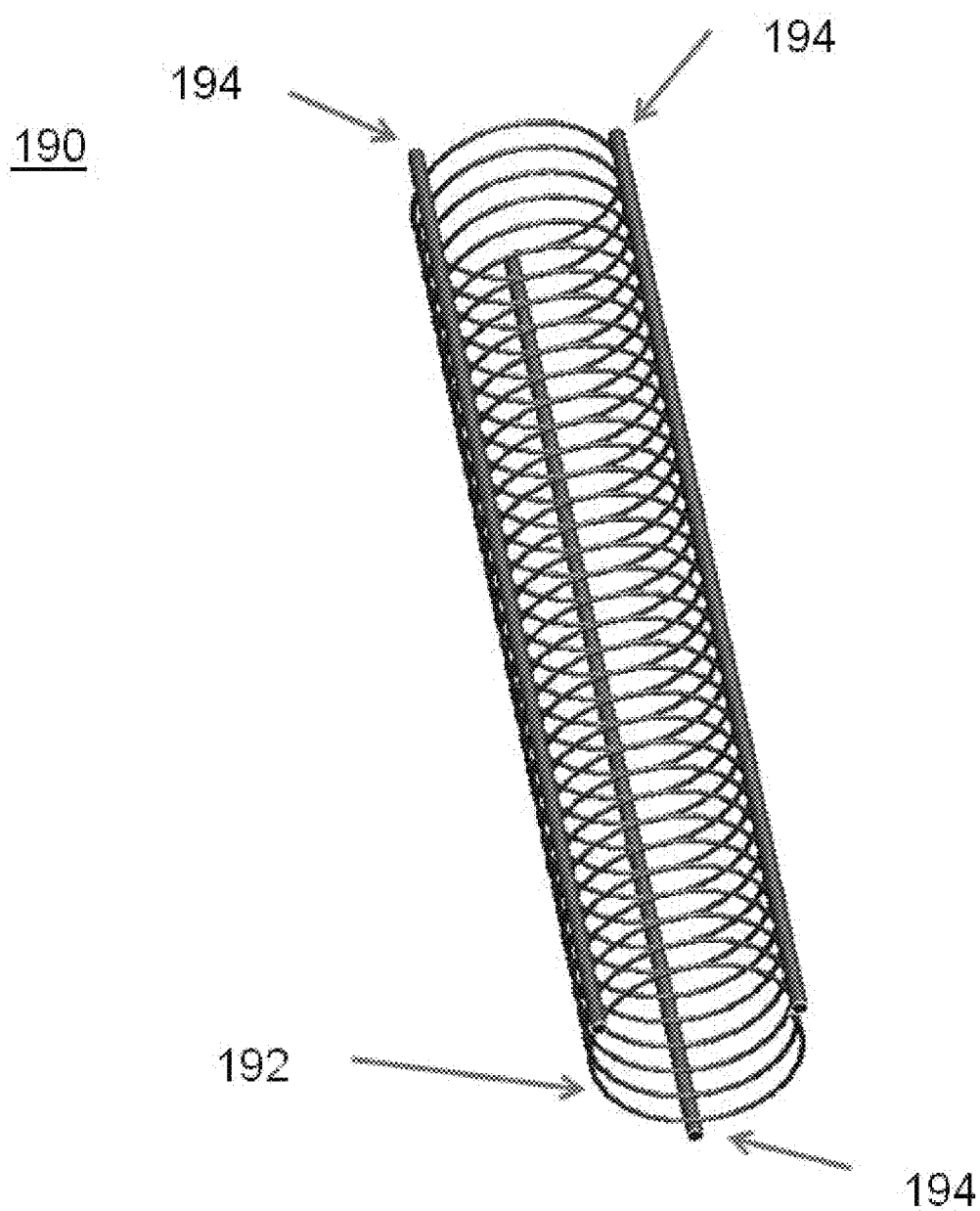

FIG. 25 is an oblique view of a filter screen used in the construction of a fourth embodiment of a filter cartridge for dialysis or ultrafiltration.

Figure 26:
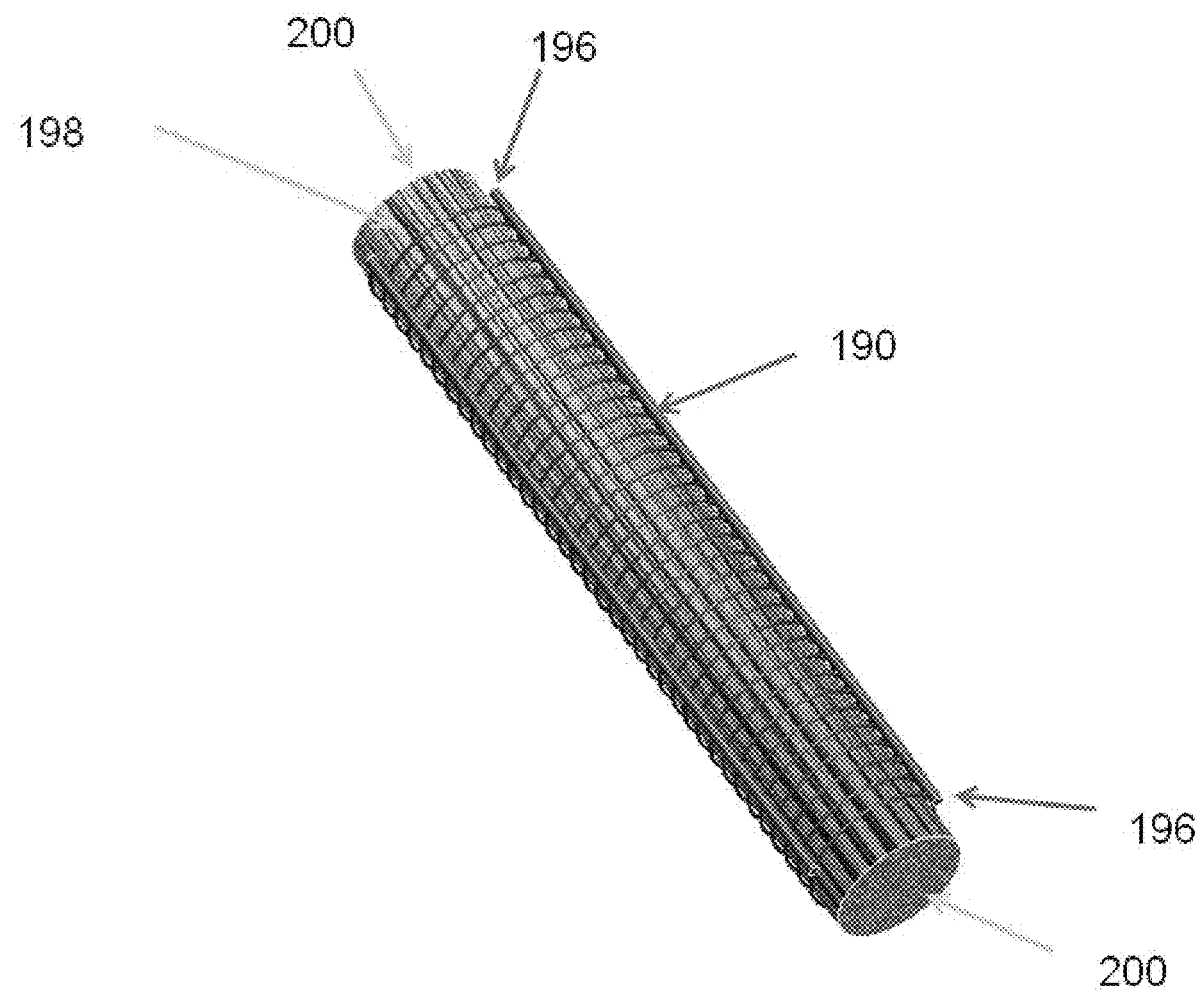

FIG. 26 is an oblique view of the filter screen of FIG. 25, with a fiber bundle inserted therein.

Figure 27:
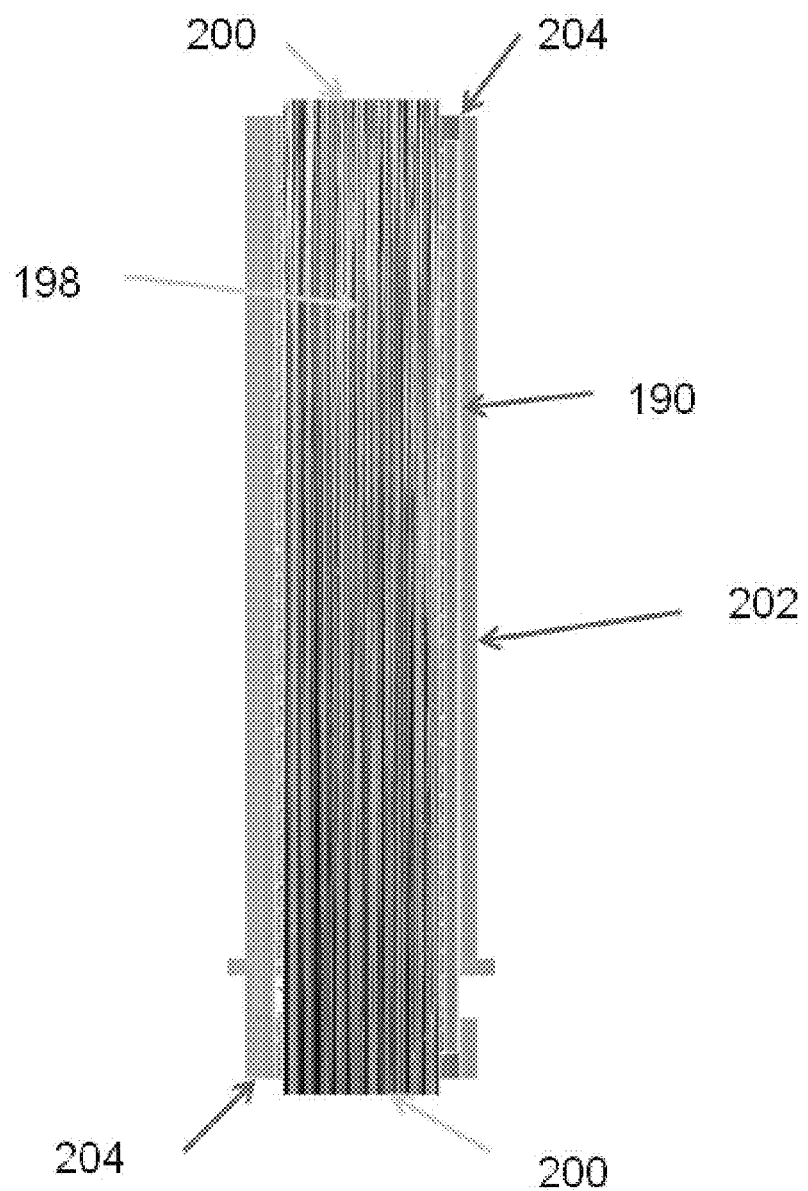

FIG. 27 is a front cross-sectional view of the filter screen and fiber bundle of FIG. 26 inserted into a housing.

Figure 28:
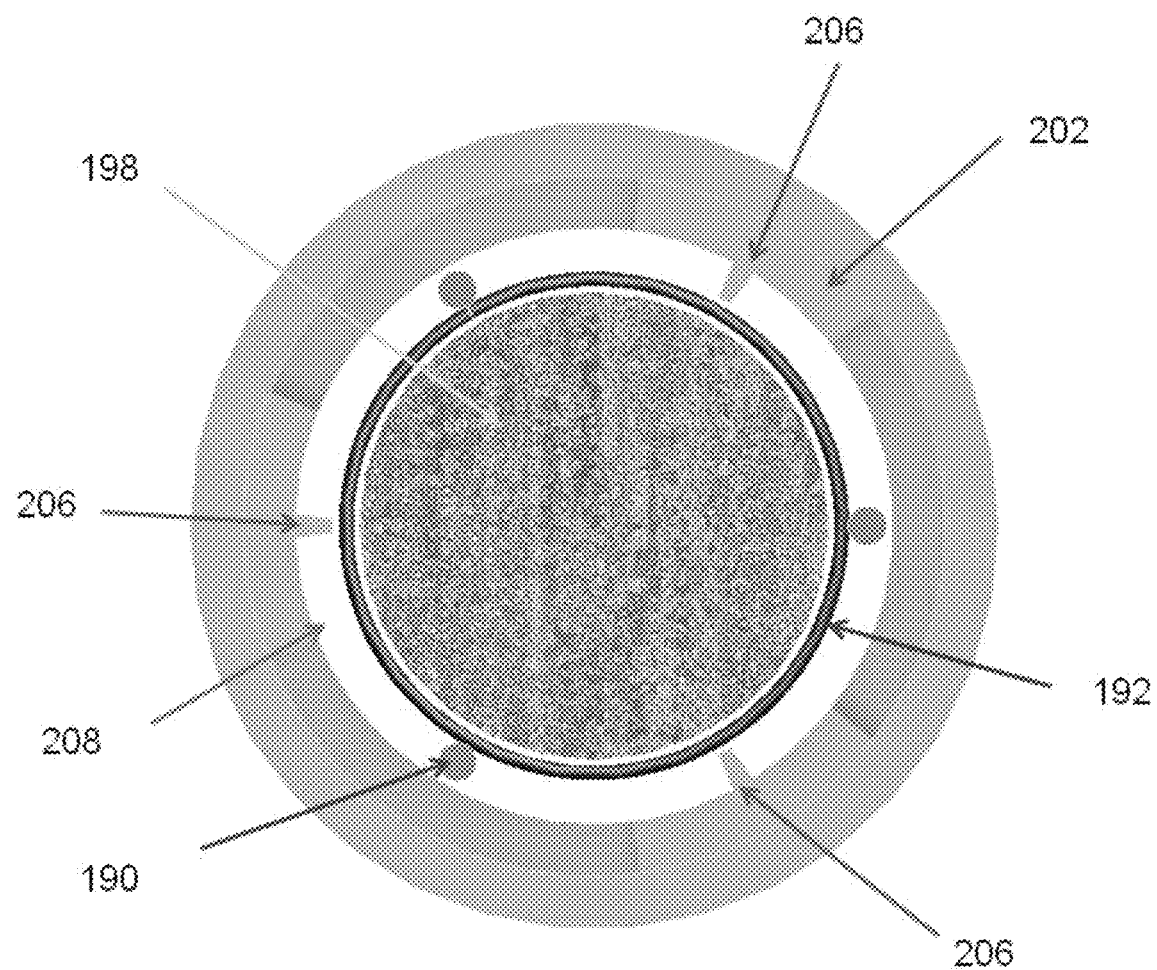

FIG. 28 is a top view of the filter screen, fiber bundle, and housing of FIG. 27.

Figure 29:
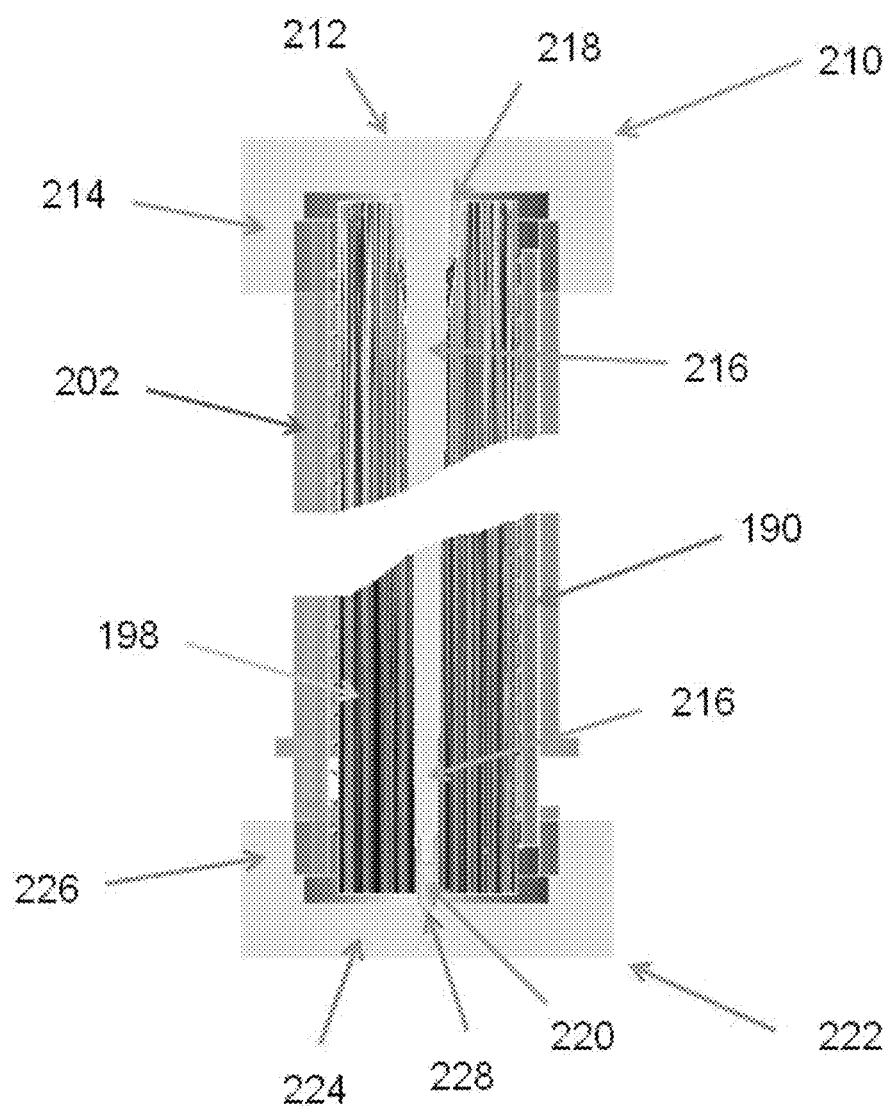

FIG. 29 is a broken front cross-sectional view of the filter assemblage of FIG. 28, with first and second potting tools.

Figure 30:
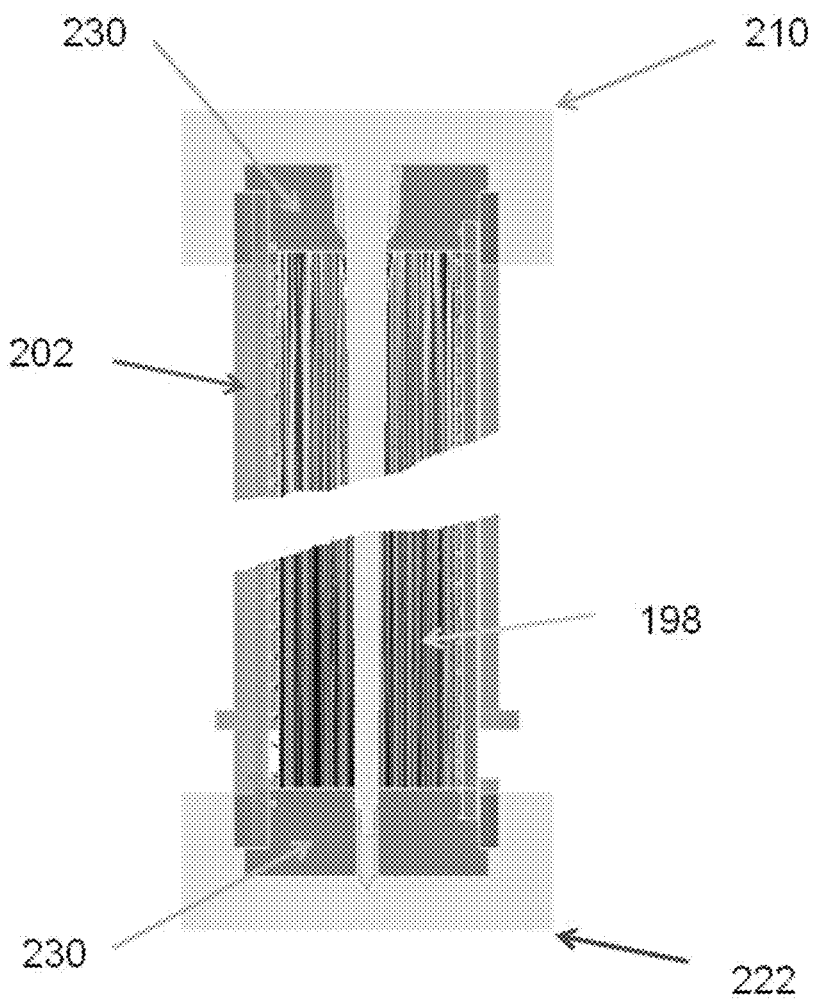

FIG. 30 is a broken front cross-sectional view of the filter assemblage and potting tools of FIG. 29, after potting material injection.

Figure 31:
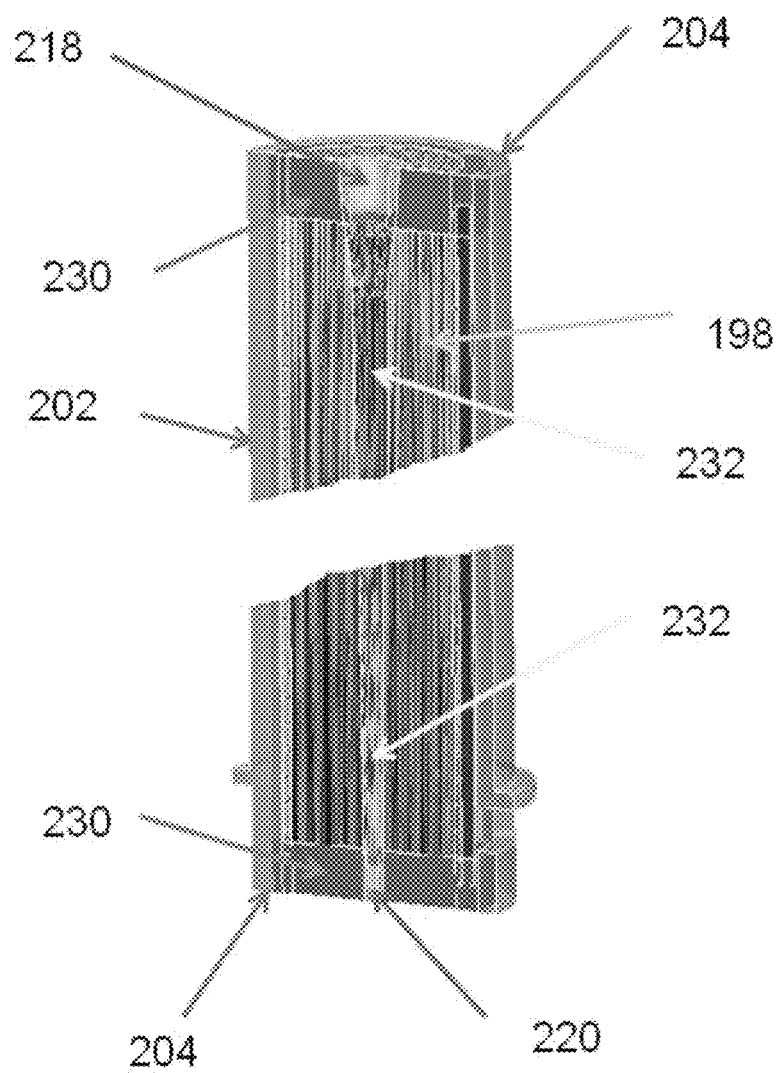

FIG. 31 is a broken oblique cross-sectional view of the filter assemblage of FIG. 28, after trimming.

Figure 32:
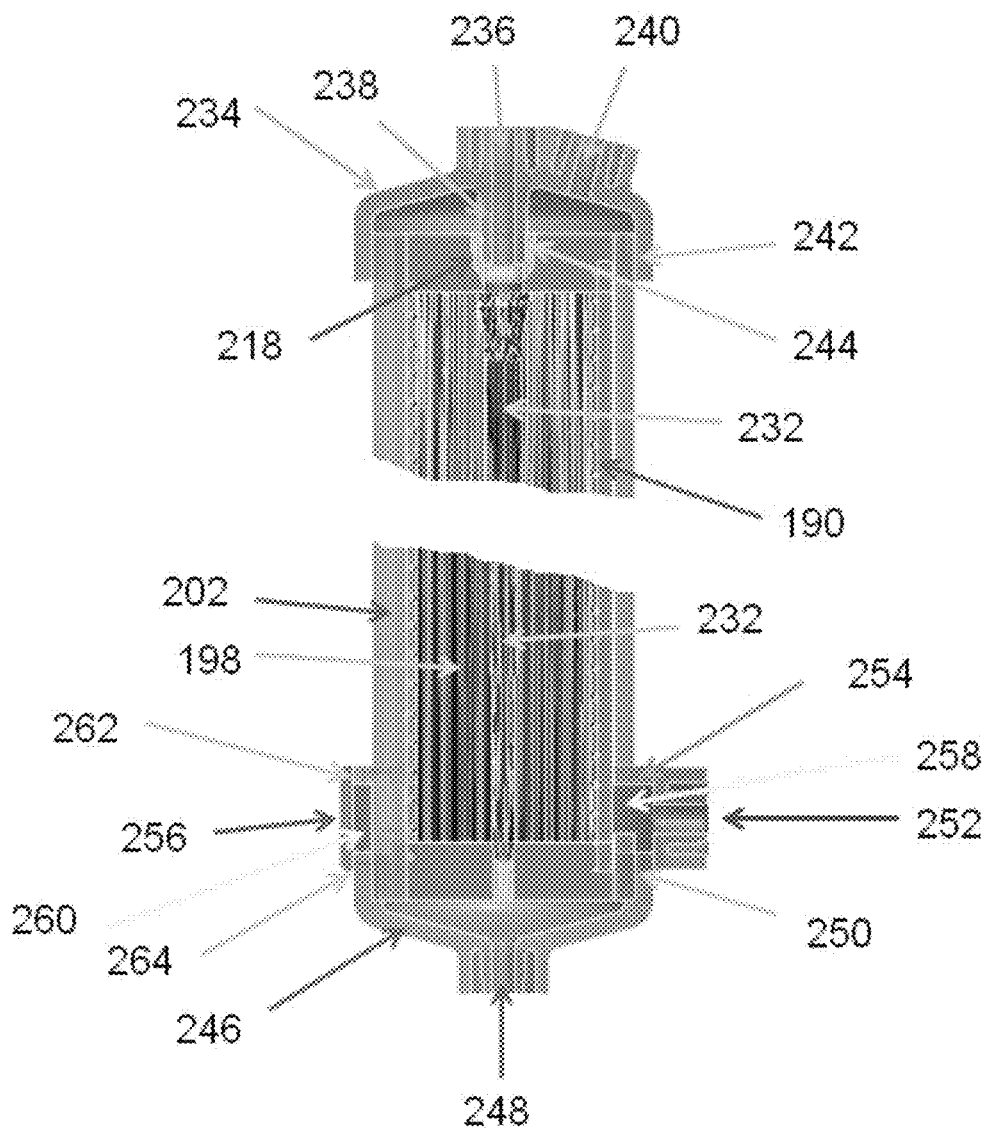

FIG. 32 is a broken front cross-sectional view of the completed fourth embodiment of the filter cartridge.

DETAILED DESCRIPTION OF THE INVENTION

Figure 1:
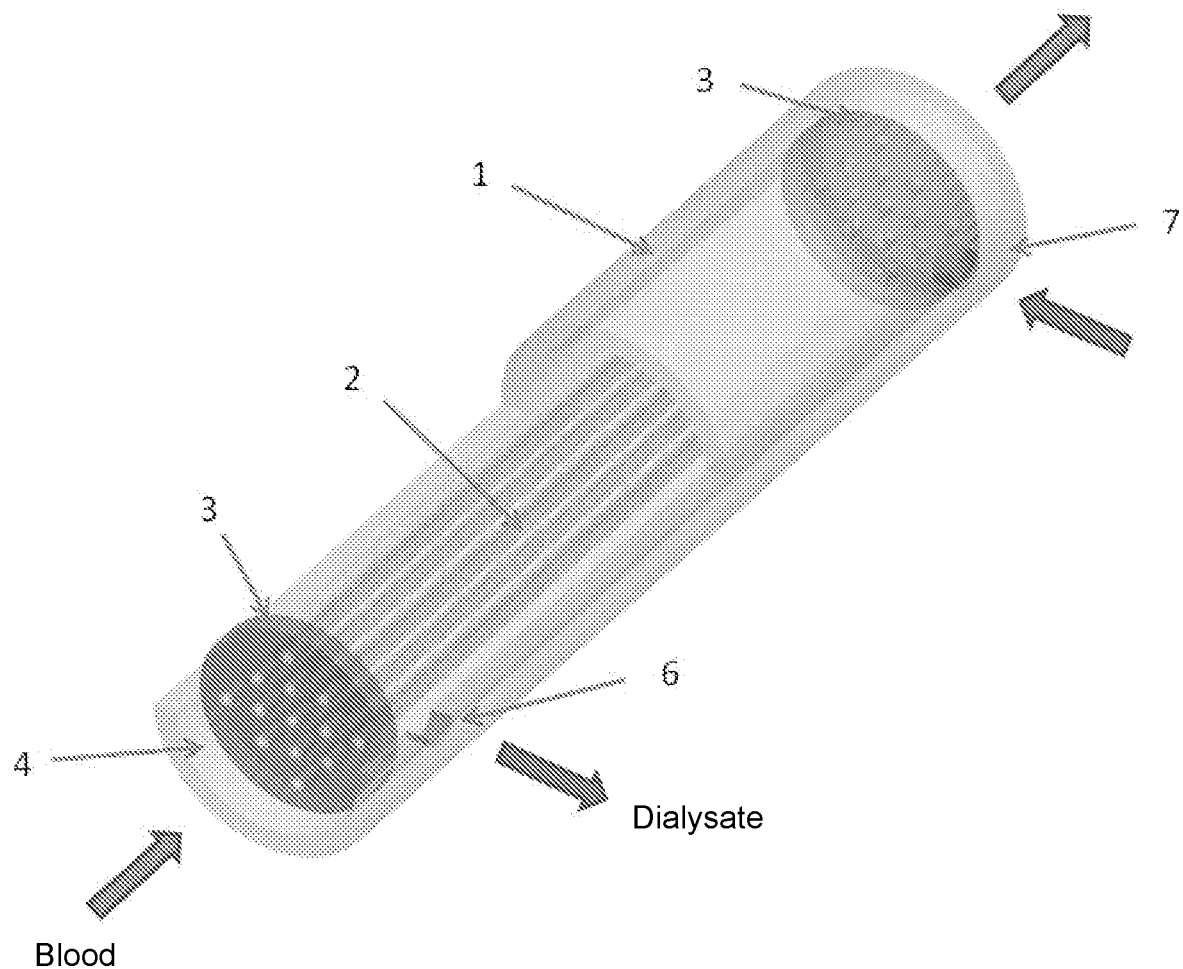
FIG. 1 is an oblique cut away view showing the construction and use of a typical filter cartridge used in medical procedures.

Referring now to FIG. 1, FIG. 1 illustrates a Prior Art cartridge that may be used to treat patients requiring hemodialysis or other related therapies. Such cartridges generally comprise a fiber bundle 2 positioned within a housing 1. Fiber bundle 2 comprises a plurality of hollow fibers, the ends of which are embedded in a potting material 3, commonly a thermosetting material, such as urethane. The potting material 3 is generally introduced as a liquid, and is cured to encapsulate the ends of all fibers. After curing, the potting resin 3 and the ends of fiber bundle 2 are cut away, to re-expose the lumens of the fibers.

In conventional forms of hemodialysis, a patient's blood is introduced to inlet header 4, flows through the lumens of the fibers of fiber bundle 2, and exits through an outlet header at the other end of the cartridge. A dialysate solution is introduced through inlet port 7, flows over the exterior surface of the fibers in fiber bundle 2, and exits through outlet port 6.

In some dialysis procedures, bodily waste products in the blood may diffuse or be transported by convection through the fiber walls or may pass through a plurality of microscopic pores in the fiber walls, or both. The removed waste products are carried away by the dialysate flow. In the management of hypervolemia, membrane hollow fibers are used to remove excess fluid from the blood by ultrafiltration. In related treatment modalities, a dialysate-like fluid may be introduced into inlet port 7, to carry excess patient fluids away through outlet port 7. Alternatively, inlet port 7 may be plugged, and outlet port 6 used to remove the excess patient fluids, such as in Slow Continuous UltraFiltration (SCUF) therapy.

Figure 2:
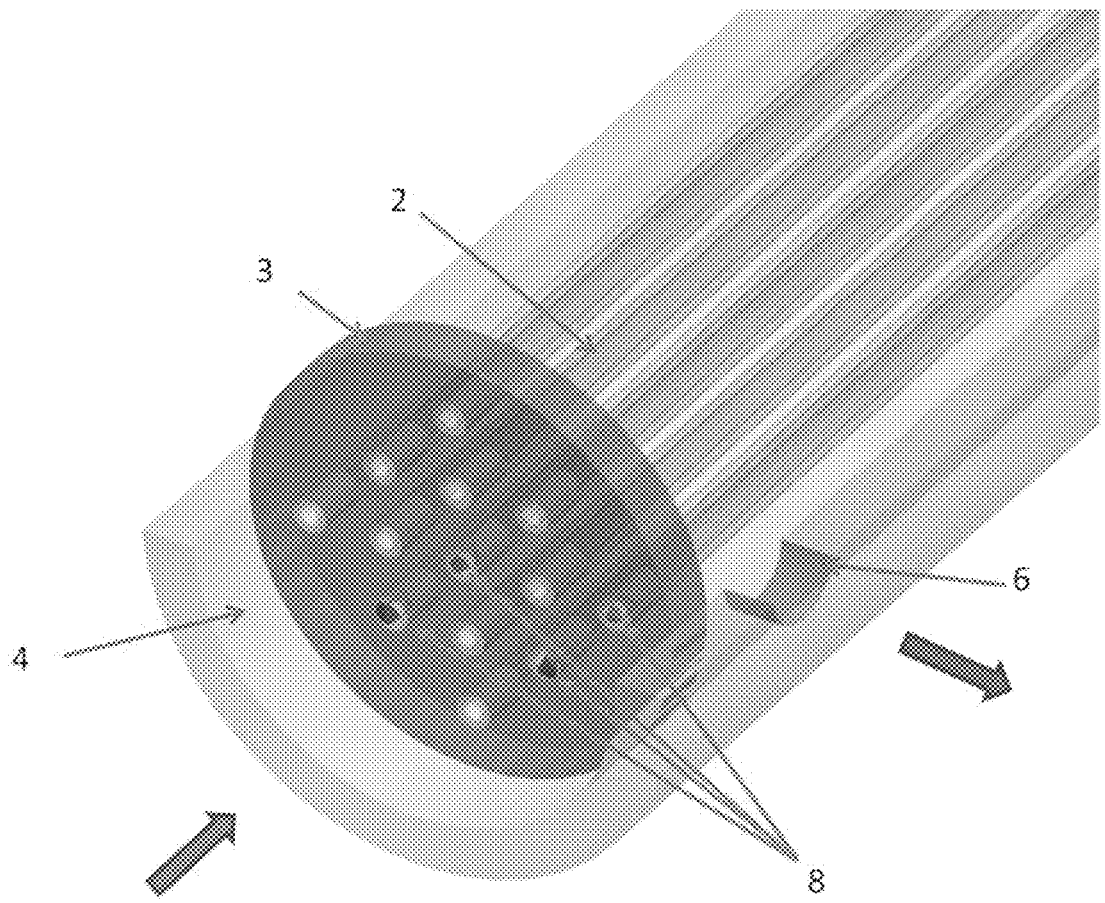
FIG. 2 is an oblique cutaway view of the inlet end of the filter cartridge of FIG. 1, illustrating typical clotting.
Figure 3:
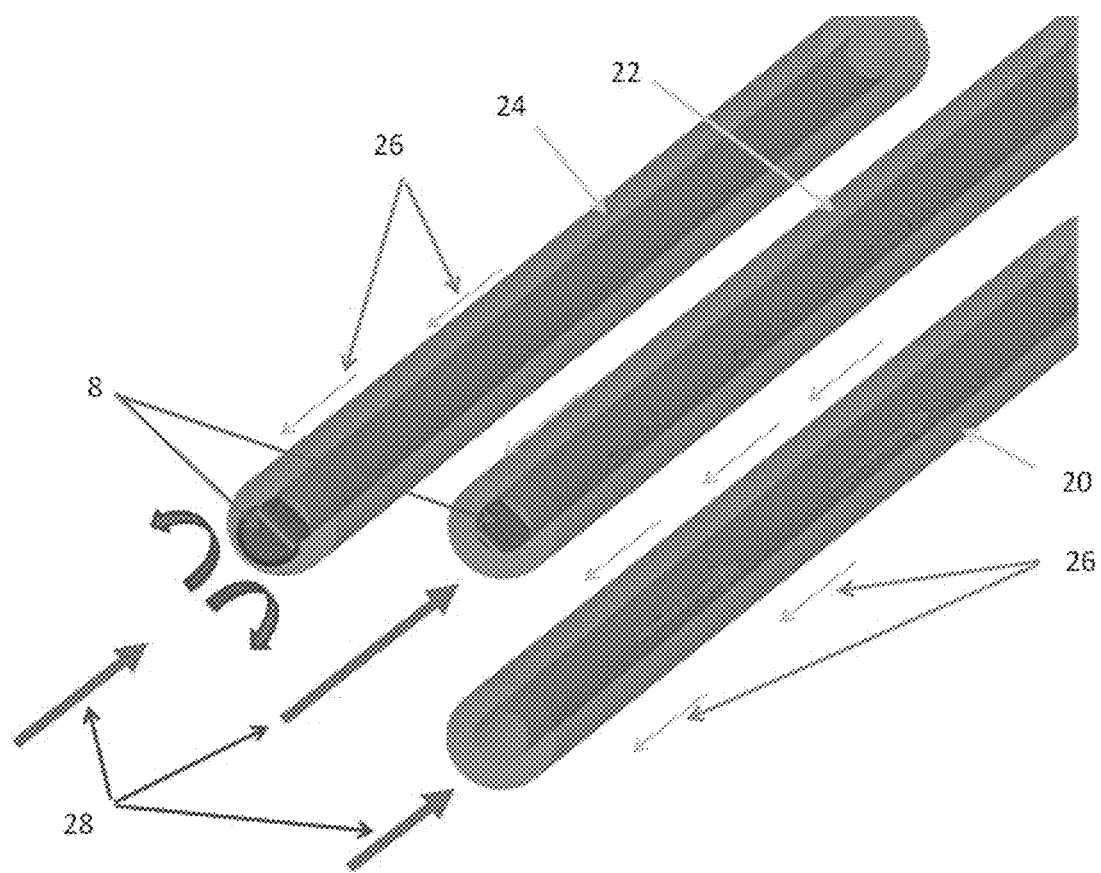
FIG. 3 is an oblique illustrative view of three fibers of the filter cartridge in FIG. 2, showing the effect of clotting.

FIG. 2, which is also Prior Art, depicts the inlet header 4 portion of the filter of FIG. 1, and illustrates the possible formation of blood clots 8, which may form and then occlude the lumens of fibers of fiber bundle 2, decreasing the effectiveness of the filter cartridge, or rendering it unusable after substantial clogging of the fibers in the bundle. FIG. 3, which is also Prior Art, illustrates three fibers of a typical fiber bundle 2 of the filter of FIG. 1 and of FIG. 2. Hollow fibers of the type used in dialysis and ultrafiltration commonly may be 150 to 300 microns in outside diameter, with lumens of 100 to 250 microns diameter. Even small blood clots 8 may partially or fully occlude the lumen of a fiber, thus rendering the entire length of that fiber less effective, or non-effective. As illustrated, some of the blood flow 28 is blocked by such clots in the lumens of fibers.

Such a filter cartridge 30 for dialysis or ultrafiltration is typically constructed by placing a fiber bundle 32 in a housing 31, and immersing the ends in a potting material 33, such that the ends of the fibers of fiber bundle 32 are encapsulated in the potting material 33, and then curing potting material 33. After curing, the potting material 33 and the ends of fiber bundle 32 are cut away, to re-expose the lumens of the fibers. Within fiber bundle 32, there exists some space between fibers, designated the inter fiber space.

Figure 4:
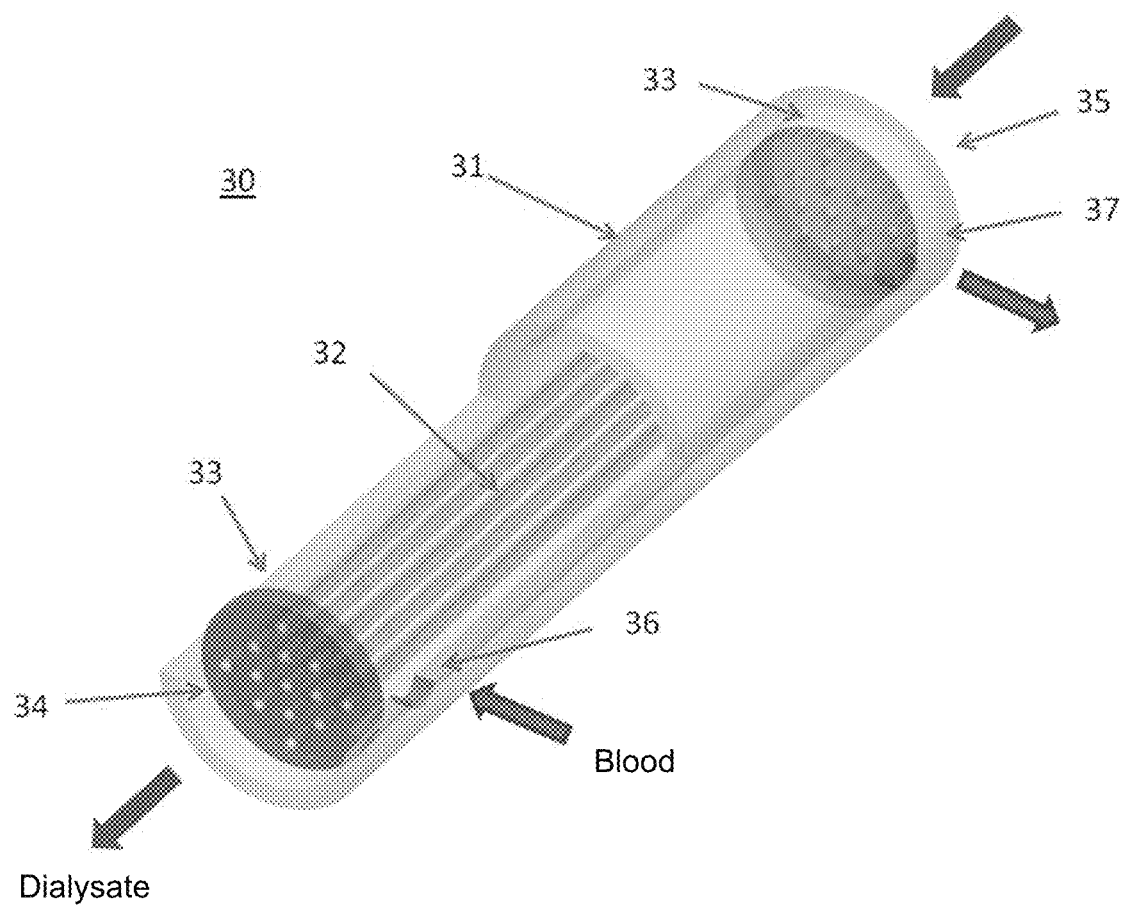
FIG. 4 is an oblique cutaway view showing an improved use of a filter cartridge for dialysis or ultrafiltration.

As shown in FIG. 4, in an embodiment of the invention, filter cartridge 30 may be used such that a patient's blood may be introduced to the inter fiber space of the cartridge through blood inlet 36, and may flow past the exterior surfaces of the fibers of fiber bundle 32, exiting through blood outlet 37. This configuration, which differs from common practice, may be termed Outside-In Flow Filtration. If dialysis is being performed, dialysate may be introduced through inlet port 35, and may flow through the lumens of the fibers of fiber bundle 32, and may exit through outlet port 34. In some treatments requiring additional ultrafiltration, a dialysate-like fluid may be introduced into inlet port 35, to carry excess patient fluids away through outlet port 34. Alternatively, inlet port 35 may be closed off, and outlet port 34 may be used to remove the excess patient fluids by means of an ultrafiltration process.

Figure 5:
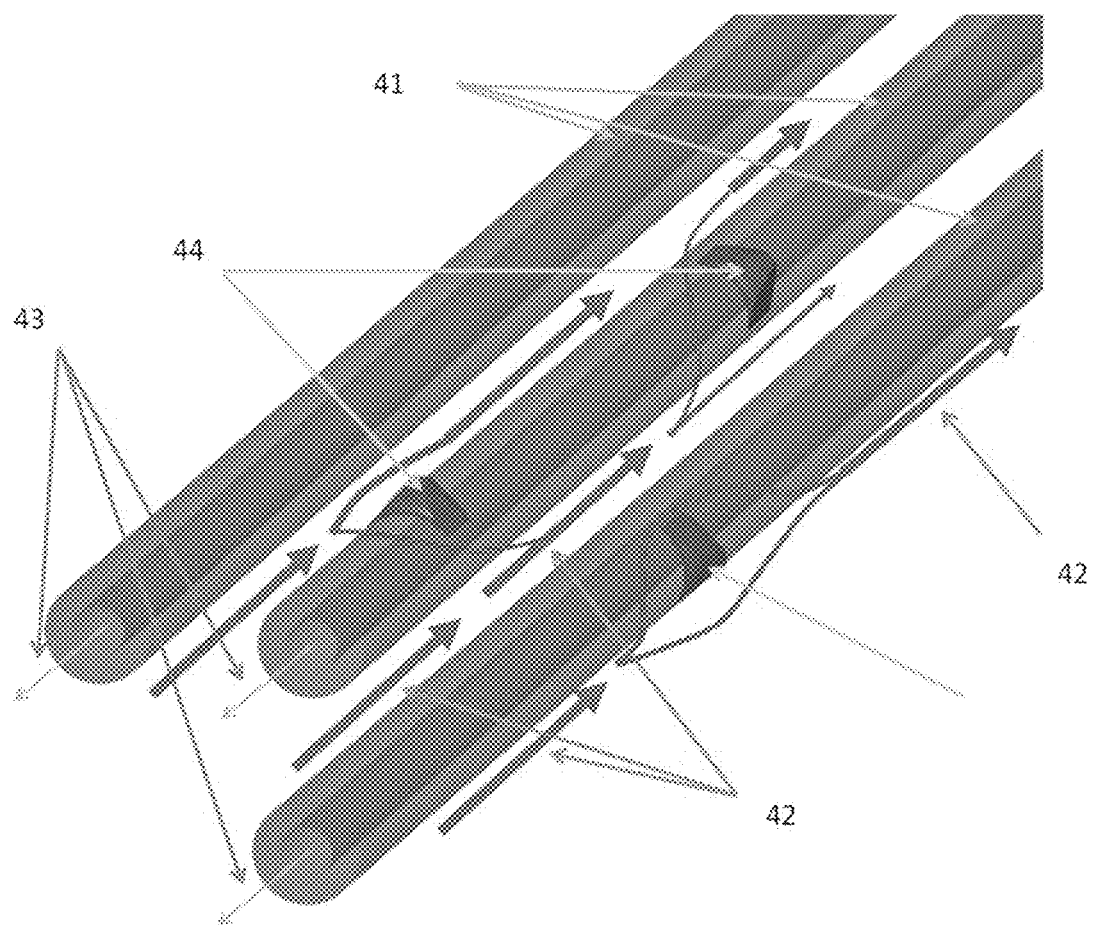
FIG. 5 is an oblique illustrative view of three fibers of the filter cartridge in FIG. 4, showing the effect of clotting.

In FIG. 5, the blood flow 42 and dialysate flow 43 are illustrated for the structure of Outside-in Flow Filtration cartridge 30 shown in FIG. 4. Assuming that blood clots 44 form, they are positioned on the exterior of fibers 41, in the interstitial space between the fibers. Since the interstitial space between fibers 41 is all interconnected, blood can easily detour around clots, and continue along the fiber bundle 32. Thus blood clots 44 render only a very small portion of the length of any fiber ineffective, and there still remain some fluid flow paths open in the inter fiber space.

While the flow regime illustrated in FIG. 5 has advantages over the conventional flow regime of the conventional cartridge of FIG. 1, there still remain some inefficiencies resulting from the details by which the blood is admitted into fiber bundle 32 through blood inlet 36.

Figure 6A:
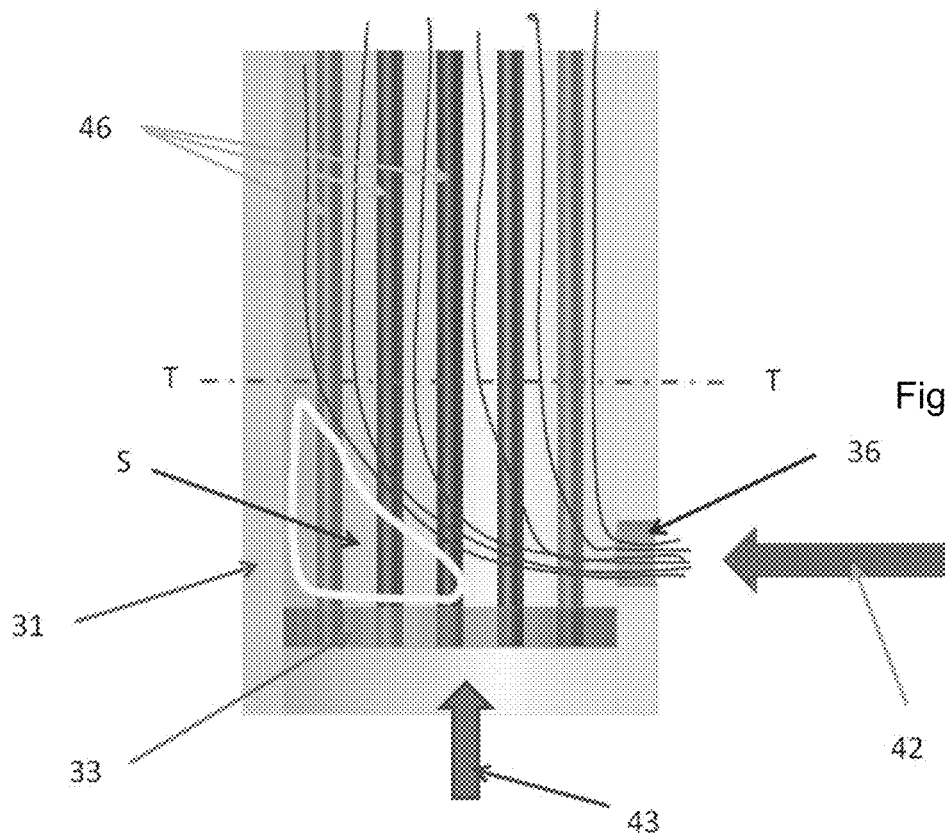
FIG. 6A is a partial cross-sectional view of the filter cartridge of FIG. 4, illustrating the blood flow into the fiber bundle, for a cartridge that does not have an orbital distributor.
Figure 6B:
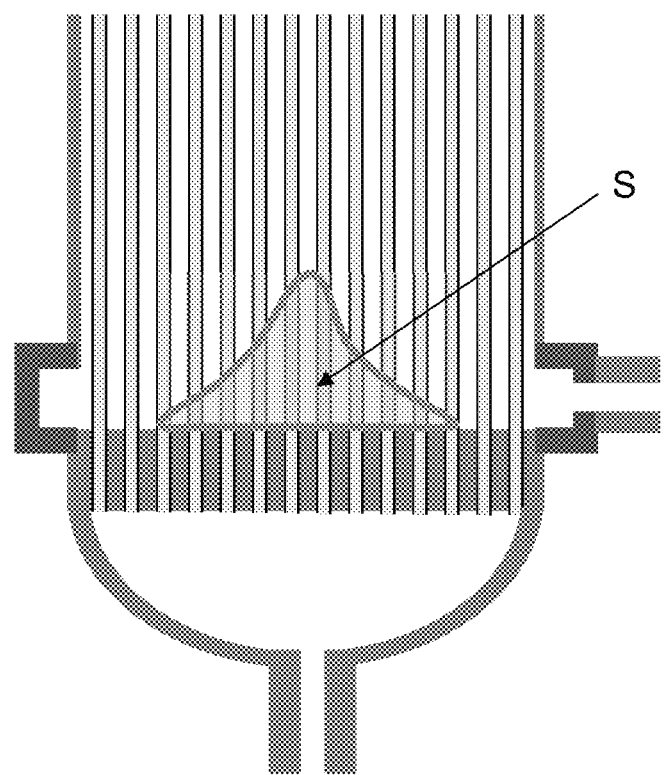
FIG. 6B is a cross-sectional view of a filter cartridge showing flow patterns in a situation where the cartridge contains an orbital distributor.

FIG. 6A illustrates one such problem. For this relatively simple geometry as illustrated, blood flow 42 from a patient enters the filter cartridge through blood inlet 36, and flows into the interstitial space between filter fibers 46, somewhat impeded by the filter fibers that are located directly adjacent to blood inlet 36. Within a portion of the length of filter fibers 46, approximately up to line T-T, the blood flow 42 transitions from the lateral or radial flow through blood inlet 36, to an axial flow along the longitudinal direction of filter fibers 46. Blood flow in the area labeled S may have a relatively small velocity, or may be stagnant, and thus the portions of filter fibers 46 within area S may operate at a lower efficiency for filtration or dialysis. Low flow velocity and stagnation also increase the propensity for the blood to form clots in those locations or may lead to sequestration or retention of leukocytes. These events may lead to adverse consequences including complete clogging of the filter. What is illustrated in FIG. 6A is a relatively simple design of dialyzer, which does not include an orbital distributor for the flow in the inter fiber space. In some other designs of dialyzers, there may be provided an orbital distributor, which conducts fluid around substantially the entire perimeter of the fiber bundle so that fluid can enter or exit the fiber bundle substantially all around the perimeter of the fiber bundle. This is illustrated in FIG. 6B. In a dialyzer cartridge that contains an orbital distributor, there may be a flow stagnation region having a slightly different location and shape from what is illustrated in FIG. 6A. For this situation, a flow stagnation region may exist near the end of the inter fiber space, on or near the axis of the fiber bundle. This is illustrated as Region S in FIG. 6B.

In embodiments of the invention, it is desired to have flow in the inter fiber space be as uniform as possible for as great a length as possible, and it is desired that flow stagnation regions be either eliminated or made as small as possible. If the fluid flowing in the inter fiber space is blood, this strategy can be beneficial in terms of reducing clot formation and other undesirable effects. If the fluid flowing in the inter fiber space is dialysate or a similar liquid, this strategy can be beneficial in terms of improving the efficiency and clearance of the dialyzer. It is possible that the need for flow uniformity and lack of stagnation regions may be more stringent when the fluid in the inter fiber space is blood (as opposed to dialysate), but such importance can be determined according to the details of a particular situation.

It is believed, although it is not wished to be limited to this explanation, that the following guidelines help to achieve and maintain uniformity of distribution of spacing of fibers within the housing (with the exception of the spacing of fibers at the void flow channels described herein that may be intentionally created near the ends of the cartridge): the use of fibers that are wavy; and a porosity of the fiber bundle ranging from 70% to 40% (corresponding to a packing fraction ranging from 30% to 60%), more particularly a porosity fraction that is between 50% and 62%. For use in situations that provide blood flowing in the inter fiber space, the fibers may have exterior surfaces that are smooth and hemocompatible.

In many situations, cartridges of the types described herein have two ends that are mirror images of each other or are symmetric about a plane that is perpendicular to the longitudinal axis of the filter. Such plane may be located midway between the ends of the cartridge and may be referred to as the midplane of the cartridge. However, embodiments are also possible in which the ends of the cartridge differ from each other in some respect. For example, such differences could be in the presence or absence of a distributor; design of the distributor at respective ends of the cartridge; presence or absence of fanning of fibers; fanning angle, area ratio or other details of fanning of fibers at respective ends; and presence or absence or design details of void flow channels at respective ends of the cartridge. At a middle or midplane (midway between the ends of the hollow fibers), the fibers may be substantially uniformly distributed, having an average spacing between the fibers, which can be described as an average fiber-centerline-to-fiber-centerline distance.

Various embodiments of the invention may be provided to overcome or improve upon less-than-ideal flow situations such as were illustrated in FIGS. 6A and 6B.

Embodiment 1

Figure 11A:
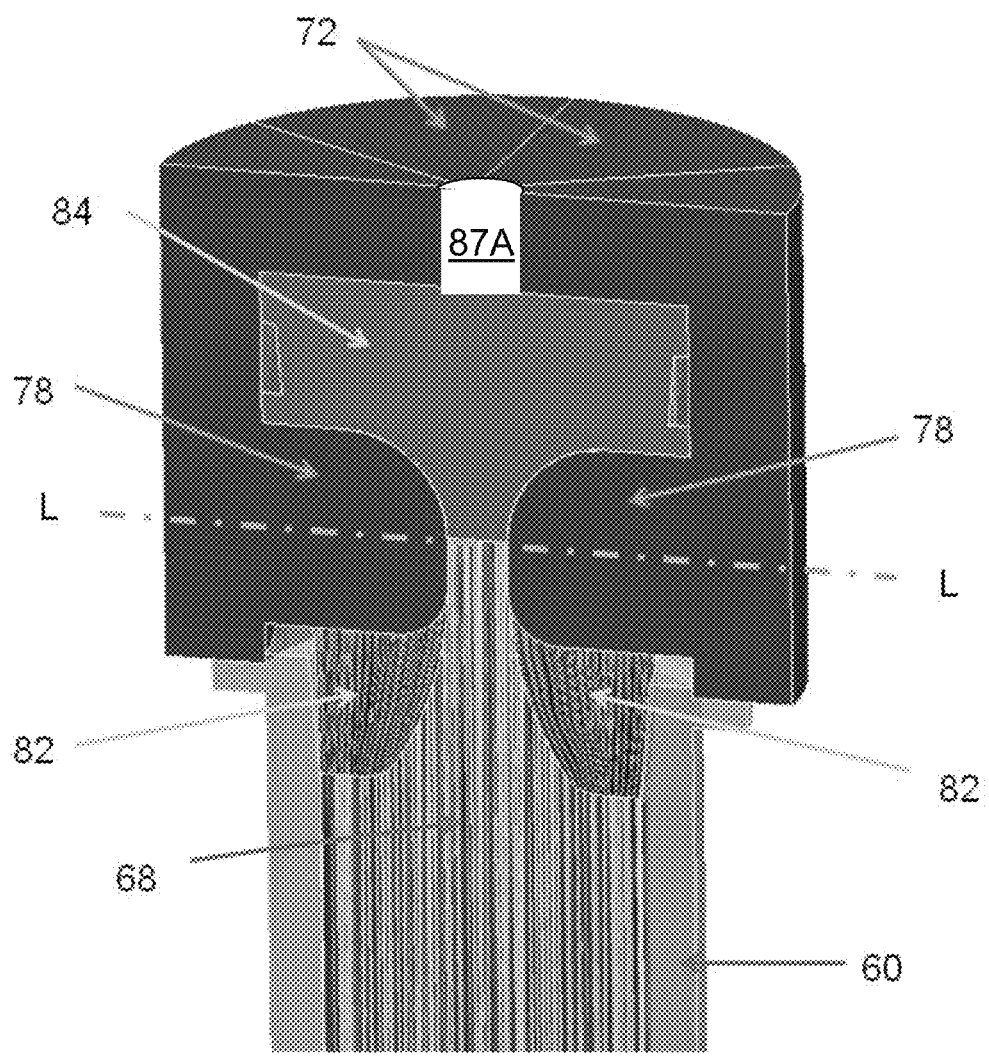
FIG. 11A is an oblique partial cross-sectional view of the filter cartridge and potting tool of FIG. 10, after a potting material has been injected and cured.
Figure 11B:
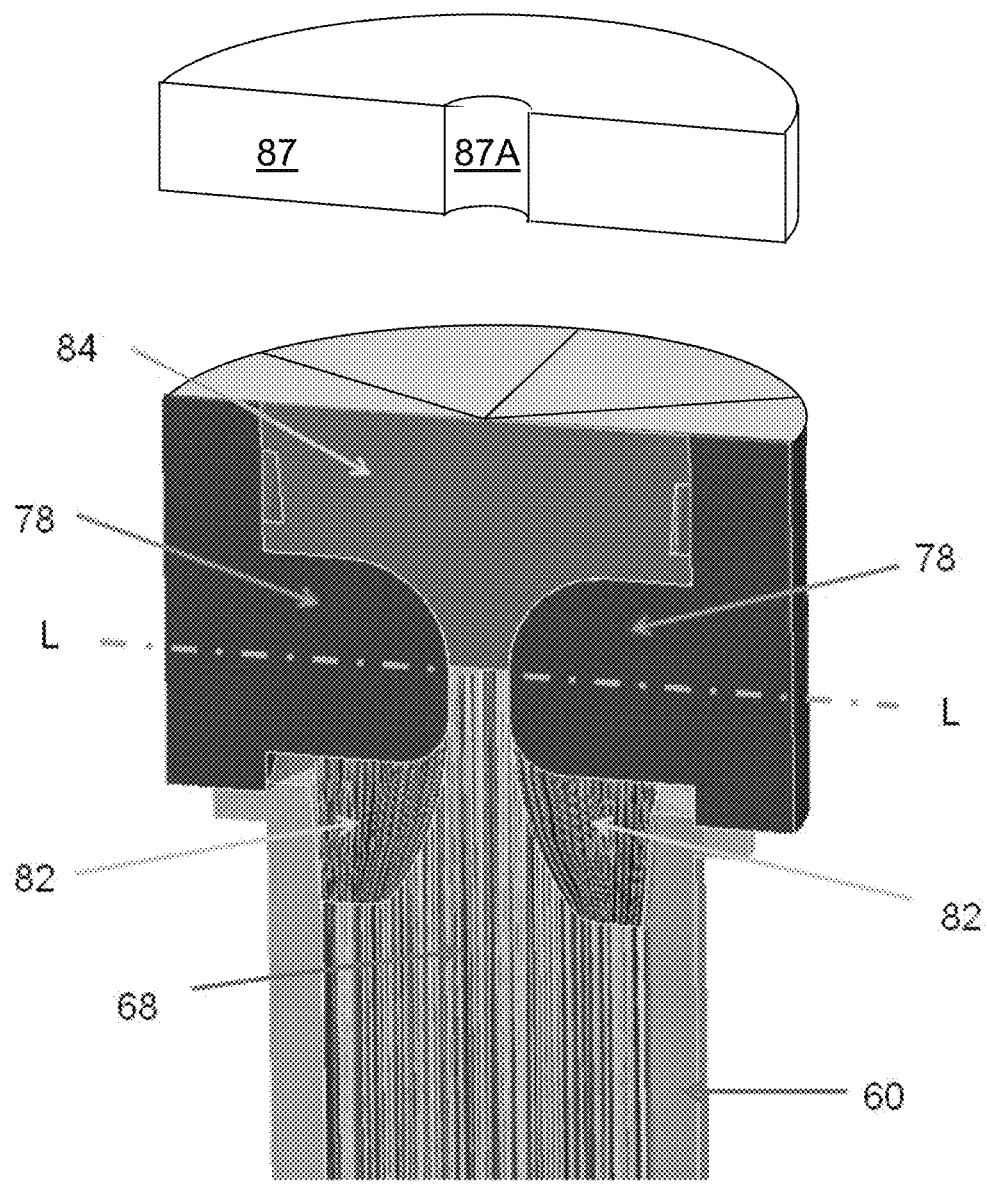
FIG. 11B is another possible tooling arrangement, in which there is provided a potting cap that is separate from the potting tool fingers.
Figure 12A:
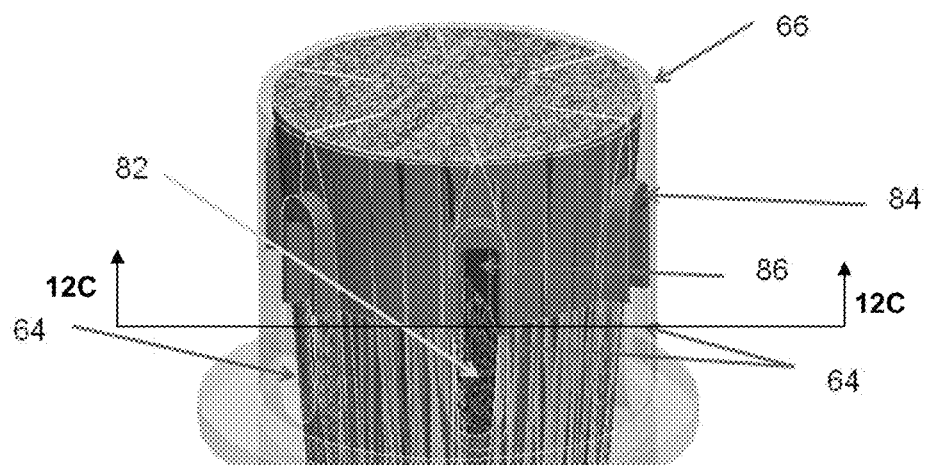
FIG. 12A is an oblique partial view of a potted filter assemblage, with the filter assemblage having been cut and polished in a first location, showing an outwardly-facing surface.
Figure 12B:
FIG. 12B is a similar view of the potted filter assemblage having been cut and polished in a second, slightly different location.
Figure 12C:
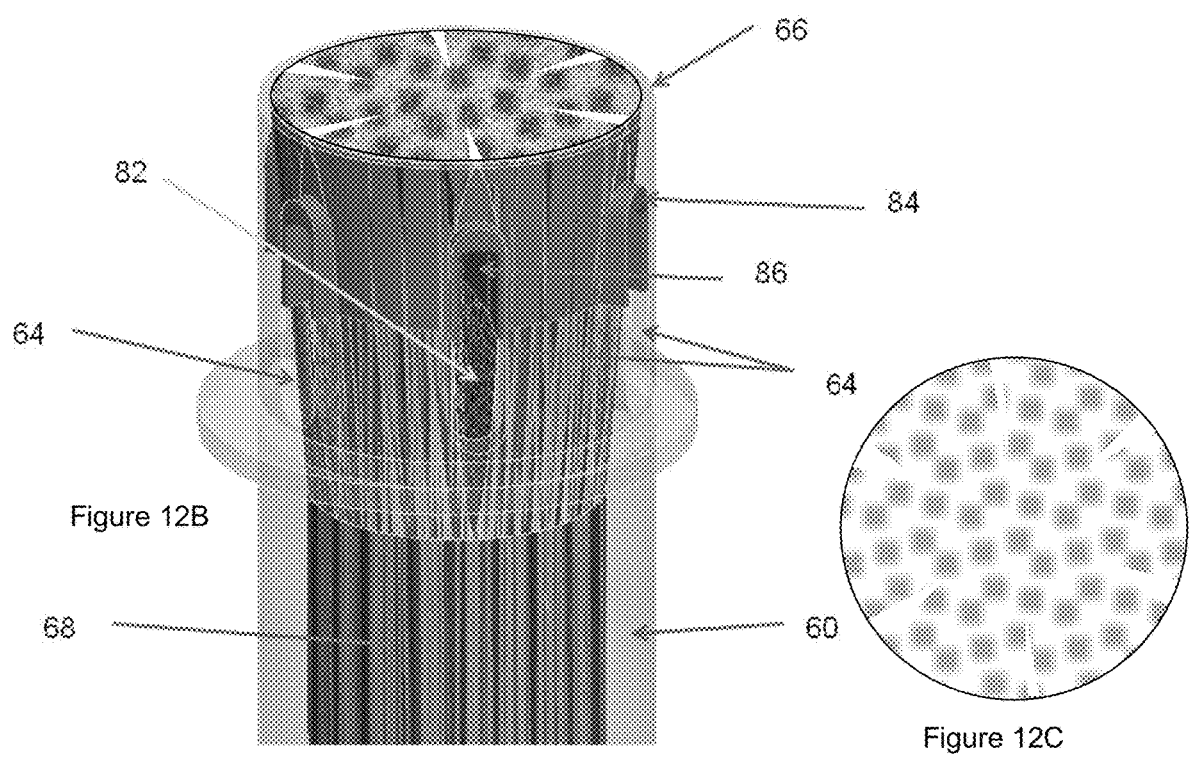
FIG. 12C is a view in the direction indicated in FIG. 12A, showing void flow channels and distribution of fibers on an inwardly-facing surface of the barrier.
Figure 12D:
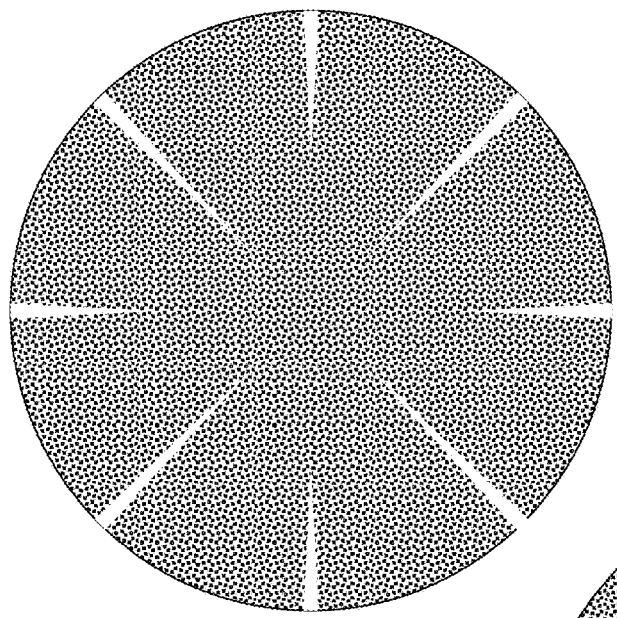
FIG. 12D shows an embodiment in which the void flow channels are of two different sizes, alternating in position around the circumference of the fiber bundle.
Figure 12E:
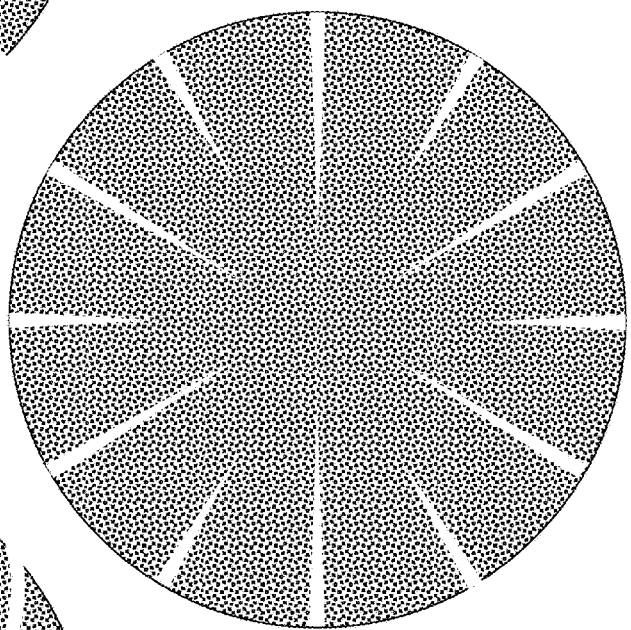
FIG. 12E shows an embodiment similar to FIG. 12D, in which twelve such void flow channels are shown.
Figure 12F:
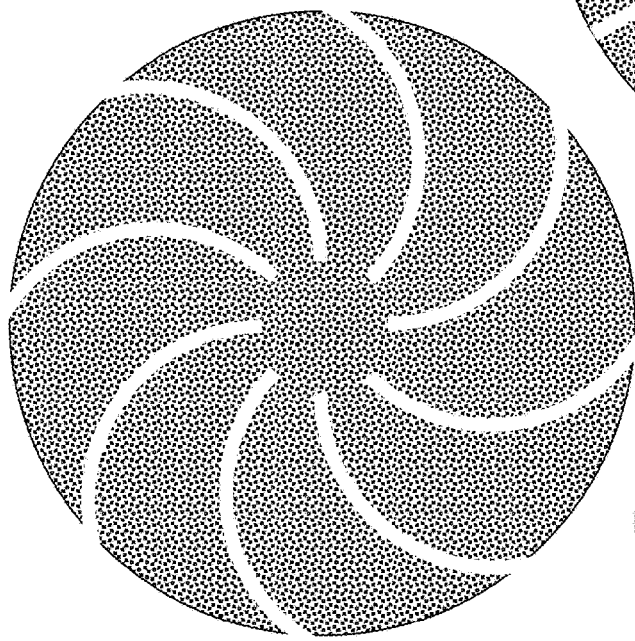
FIG. 12F shows yet another possible arrangement of void flow channels, in which the void flow channels are curved.
Figure 12G:
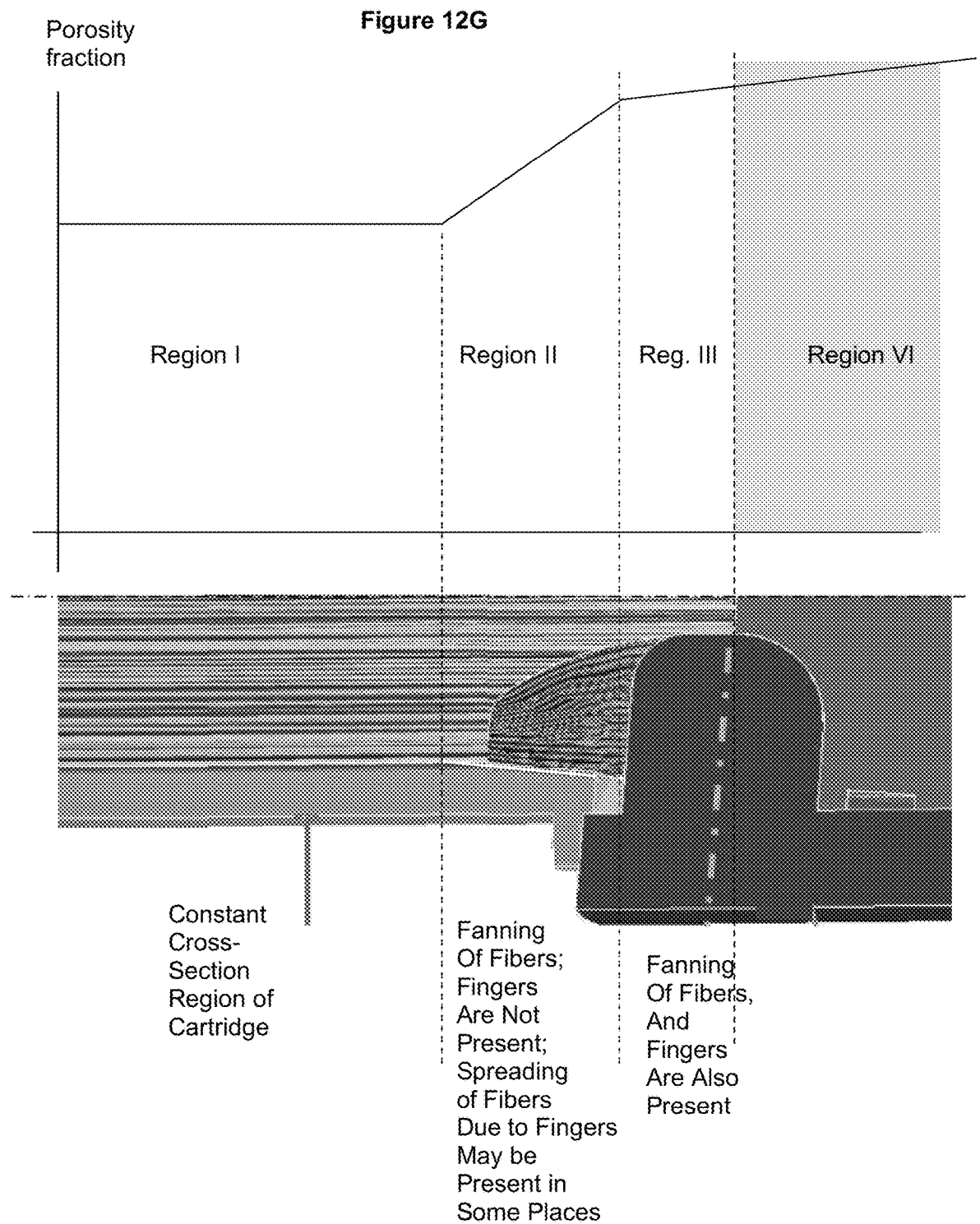
FIG. 12G is an illustration showing how the local fiber porosity could vary as a function of position along the longitudinal axis of the cartridge, taking into account both fanning of fibers and fiber rearrangement caused by the potting tool fingers.
Figure 13:
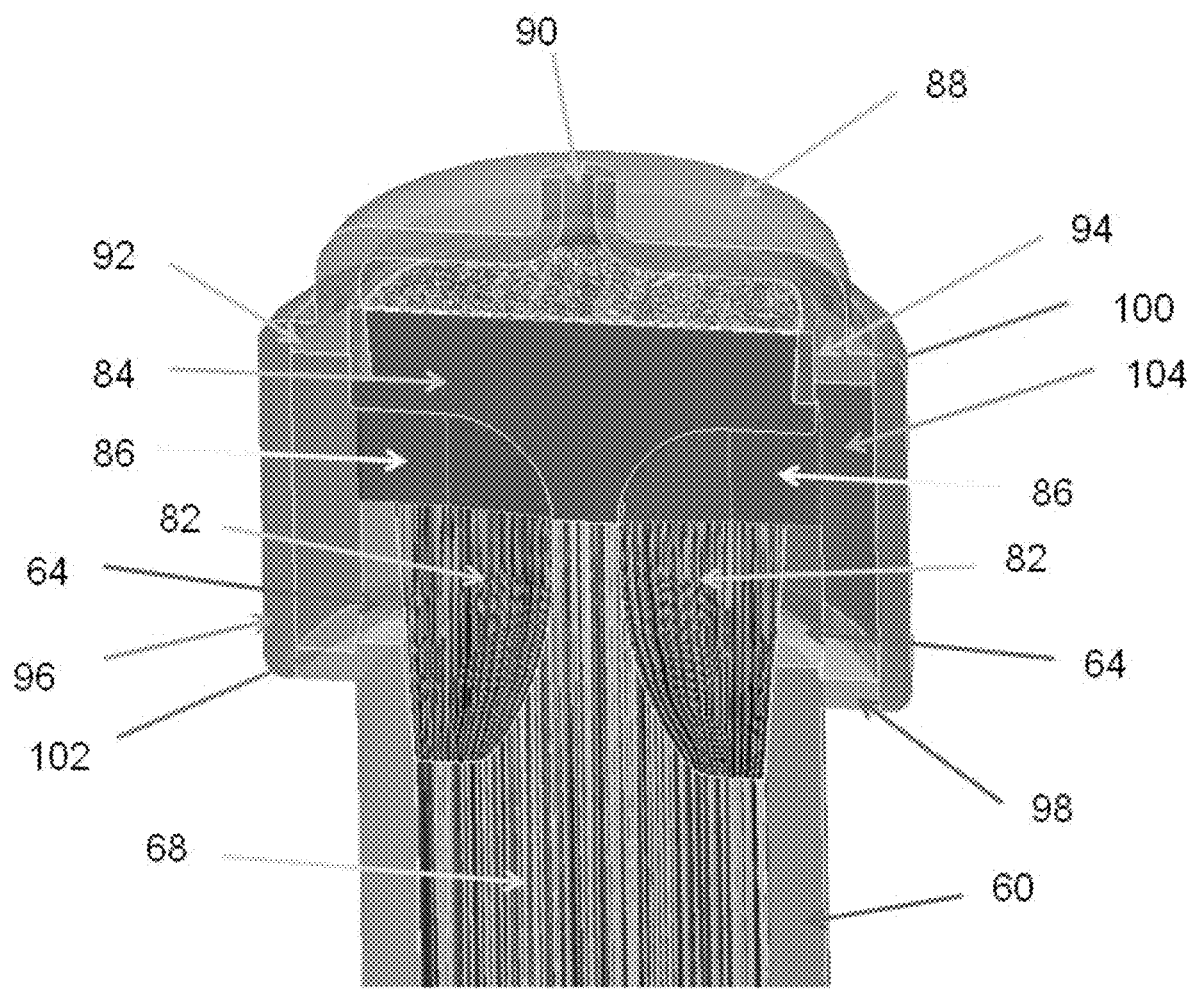
FIG. 13 is an oblique partial cross-sectional view of a completed filter cartridge of the first embodiment.

A first embodiment of the invention is described in FIGS. 7A through 13. The completed cartridge is shown in FIG. 13, and it may be constructed in accordance with the steps shown in FIGS. 7A through 12G. In this first embodiment, void flow channels are provided extending into the fiber bundle from the outside circumference of the fiber bundle.

The embodiments and construction steps described below are described in reference to a first end of such a cartridge, but it is intended that identical steps could also be performed in the manufacturing of the second end of the cartridge. It is also contemplated, alternatively, that the two ends of the cartridge could differ from each other in some way, as discussed elsewhere herein.

In embodiments of the invention, there may be provided a housing, and a plurality of fibers, at least some of the fibers being hollow and having porous walls or being semipermeable membranes, at least portions of the fibers being contained within the housing. The fibers may have an average fiber-to-fiber spacing at a mid-region of the cartridge, with mid-region referring to midway between the two ends of the cartridge with respect to a longitudinal direction of the cartridge. Similarly, midplane can be a plane cutting through the cartridge, perpendicular to the longitudinal axis of the cartridge, midway between the two ends of the cartridge. The term fiber-to-fiber spacing may be understood to refer to distance between centerlines of nearest-neighbor fibers.

In some embodiments of the invention, some local void flow channels are provided in the fiber bundle near an end of the fiber bundle. The void flow channels can be considered to be regions having no fibers, such that the void flow channel has a transverse dimension that is at least 3 times or at least 5 times an average fiber-centerline-to-fiber-centerline spacing at the midplane of the cartridge. Transverse can mean generally perpendicular to the principal or lengthwise direction of the void flow channel, and also generally perpendicular to the longitudinal direction of the cartridge. The void flow channels can allow fluid in the void flow channel to flow into interior portions of the fiber bundle more easily than would be true if the void flow channel were absent and the flow had to cross or pass by a number of typically-spaced fibers to reach interior portions of the fiber bundle. With respect to the longitudinal direction of the cartridge, in this embodiment, the void flow channels may occupy a limited region near an end of the cartridge. It is envisioned that for a substantial fraction of the length of the cartridge especially the middle of the cartridge, the fiber bundle would contain fibers that are substantially uniformly spaced within the housing. The presence of the void flow channels near an end of the fiber bundle can allow the entering fluid flow to enter more easily and directly into the interior of the fiber bundle, and to do so within a relatively small distance along the longitudinal direction of the cartridge. It is expected that as entering fluid flow approaches the fiber bundle at the outer circumference of the fiber bundle, depending on the design of the orbital distributor, a portion of the flow may enter the fiber bundle directly if the design of the orbital distributor permits this, and a significant portion of the flow may enter the void flow channel(s) and may flow inward into the fiber bundle along the principal direction of the void flow channel(s), with the flow gradually exiting from the void flow channel through the boundaries of the void flow channel into the fiber bundle. Thus, flow can easily access portions of the fiber bundle that are well inside the fiber bundle, without having to flow past or around a large number of fibers to get deep inside the fiber bundle. If a similar geometry is provided at the discharge end of the cartridge, it can be expected that there would exist similar flow patterns at the discharge end of the cartridge, but the flow patterns would be oppositely directed in the sense of exiting rather than entering. It may also be desirable that the exit distributor be of the orbital type such that it will function as a trap to capture any loose clots that may become loose during treatment, and thus prevents their travel with blood stream to the patient's body.

It is expected that, as a result of such design features, the flow transitions into a uniform axial flow along the longitudinal direction of the cartridge, within a transition region that occupies only a relatively short length along the longitudinal direction of the cartridge. This represents an improvement over, for example, the situation illustrated in FIGS. 6A and 6B.

Figure 7A:
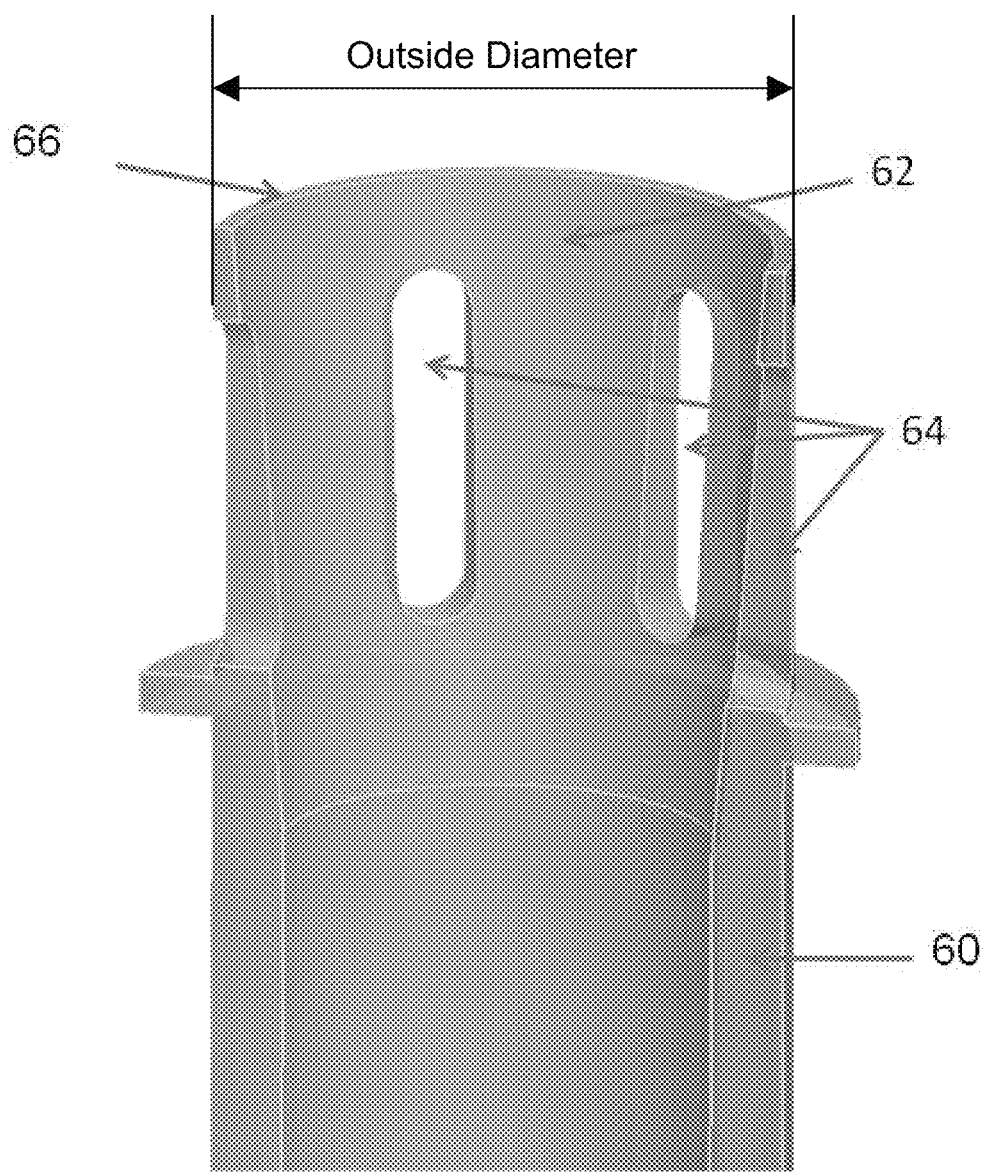
FIG. 7A is an oblique partial cross-sectional view of a housing of a first embodiment of the invention, having a plurality of radial inlet ports, and having an interior that is tapered near the end while having a generally cylindrical tube exterior.
Figure 7B:
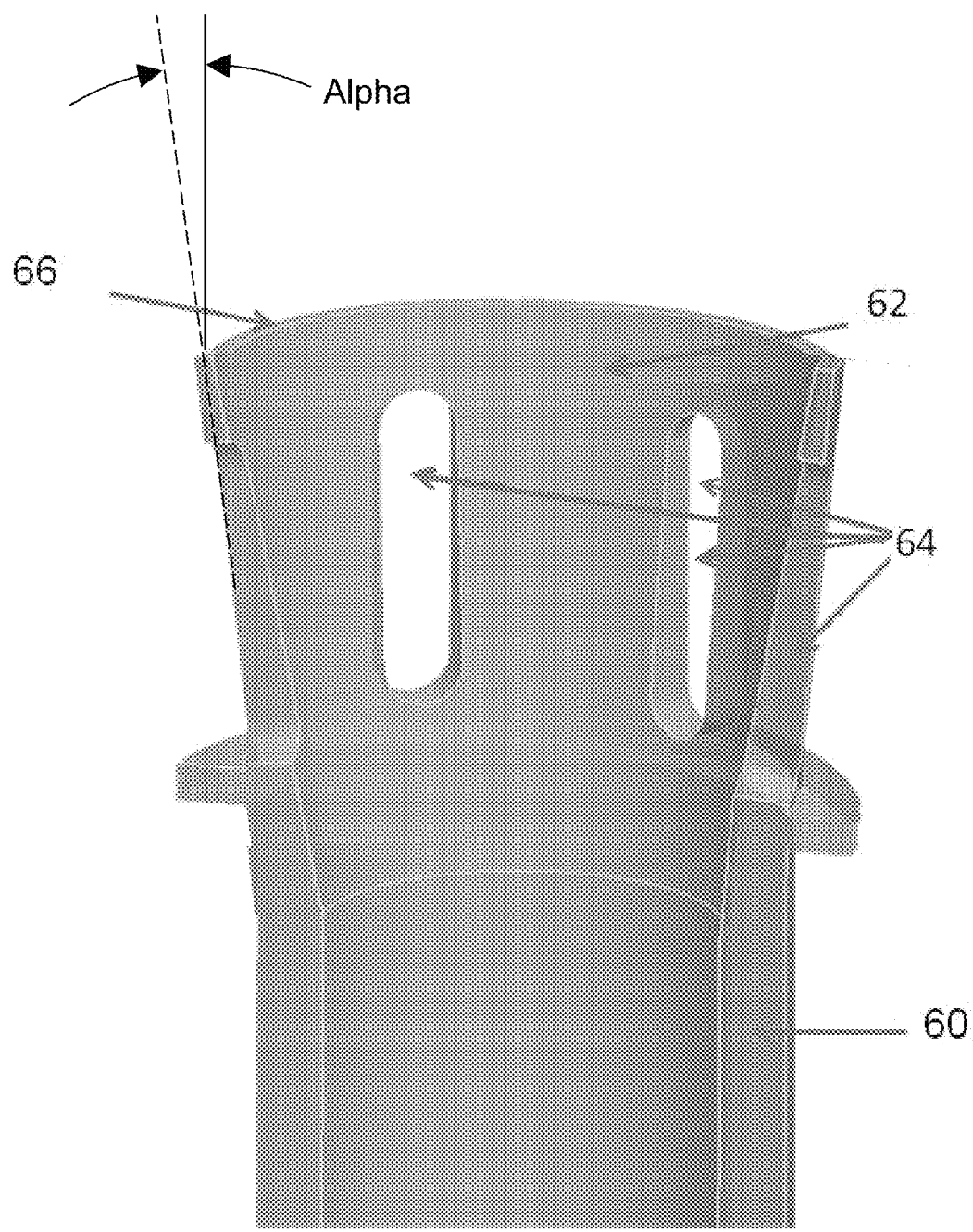
FIG. 7B is a similar view of a housing in which both the outside of the tube and the inside of the tube are tapered.

Referring now to FIGS. 7A and 7B, a housing 60 has a tube end portion 62 having an interior that is tapered near the end such that the inner diameter of the tube increases toward tube end 66. A plurality of radial ports 64 are provided in tube end portion 62 of the housing 60, in proximity to tube end 66. In FIG. 7A, the outside of the tube is illustrated as being generally cylindrical even while the inside of the tube is tapered near the end of the tube. Accordingly, it is illustrated in FIG. 7A that the tube has an outside diameter. In FIG. 7B, the inside of the tube is again internally tapered near the end of the tube, and in FIG. 7B the outside of the tube is tapered near the end of the tube. Accordingly, it is illustrated in FIG. 7B that there is a taper angle alpha describing the taper of the outside of the tube with respect to a longitudinal centerline of the tube. Other geometries near the end of the tube are also possible. Furthermore, with regard to both FIG. 7A and FIG. 7B, it is possible that an additional piece may at some point be joined to the outside of the tube to provide an orbital distributor or other feature. Also, although the tube is shown as being generally axisymmetric, other shapes are also possible for one skilled in the art, such as oval, rectangular, etc.

In this first embodiment (and later the second embodiment as well), it would be possible to manufacture the housing initially in two parts, with the two parts eventually being joined to each other. For example, the joint could be at or near the midplane of the cartridge. Such a technique would, for example, allow the formation of the internal taper near both ends of the housing. Alternatively, it may be possible to manufacture the housing as a single piece such as by extrusion, and form an internal taper if desired by appropriate means. In any instance, it is further possible for another piece such as an orbital distributor to be joined to the tubular housing at some stage of manufacture.

Figure 8:
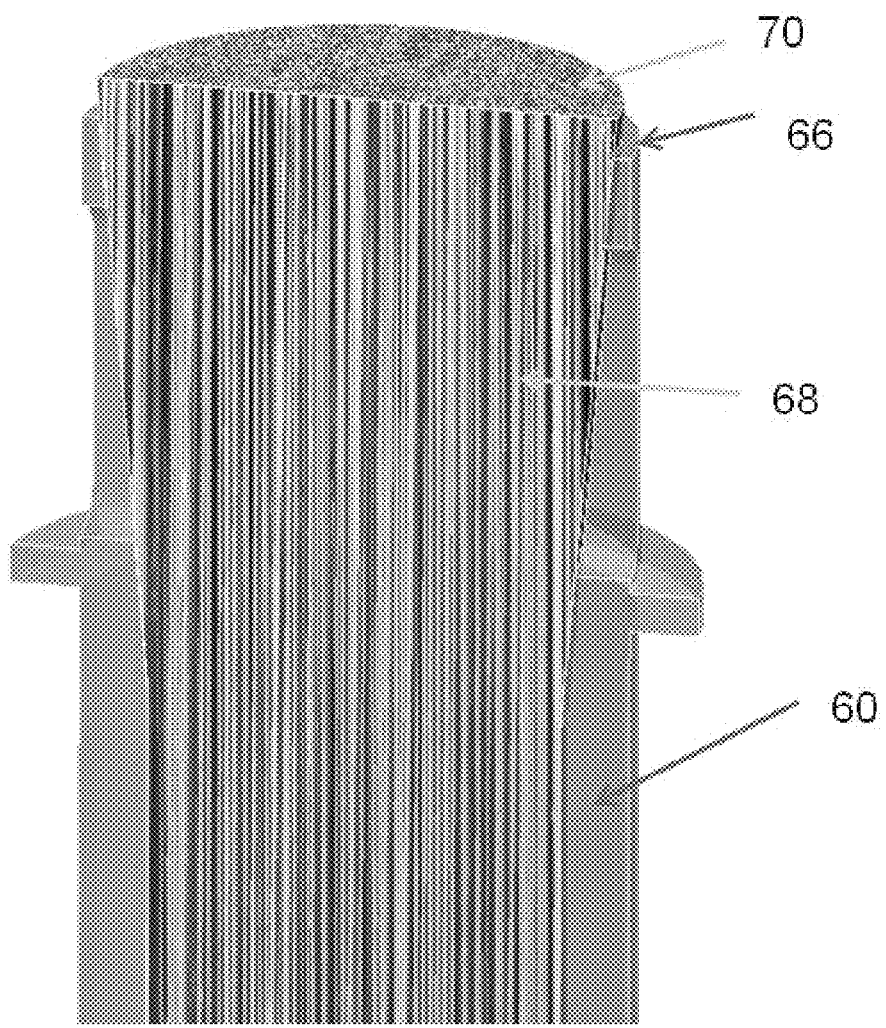
FIG. 8 is an oblique partial cross-sectional view of the housing of FIG. 7A, showing the placement of the fiber bundle.

Referring now to FIG. 8, a fiber bundle 68 has been placed into housing 60 of FIG. 7A. (Although this is illustrated using the housing of FIG. 7A, these steps could similarly be performed for the housing of FIG. 7B if that is the type of housing used.) Preferably, at this stage, fiber ends 70 protrude slightly beyond tube end 66.

It is possible that at this stage of manufacturing, prior to potting, the ends of the hollow fibers may be closed or sealed. Such a step would avoid intrusion of potting resin into the lumens of the fibers during the potting process. It is possible to seal the fiber ends using any form of application of heat. For example, a non-contact heat source such as radiant heating could be used. It is further possible that a laser could be used both for cutting the fibers to length and for sealing the ends of the fibers in a single operation, or alternatively, cutting could be a separate operation and sealing could be a separate operation. Either or both steps could be performed by a laser. Alternatively, still other manufacturing processes are also possible, such as multiple potting steps involving a first potting step to seal the fiber ends and a second potting process to cast the potting that will remain in the finished product. The sealing step could be performed after the fibers are in the housing, although if desired it would be possible to perform such step before the fibers are introduced into the housing.

Figure 9:
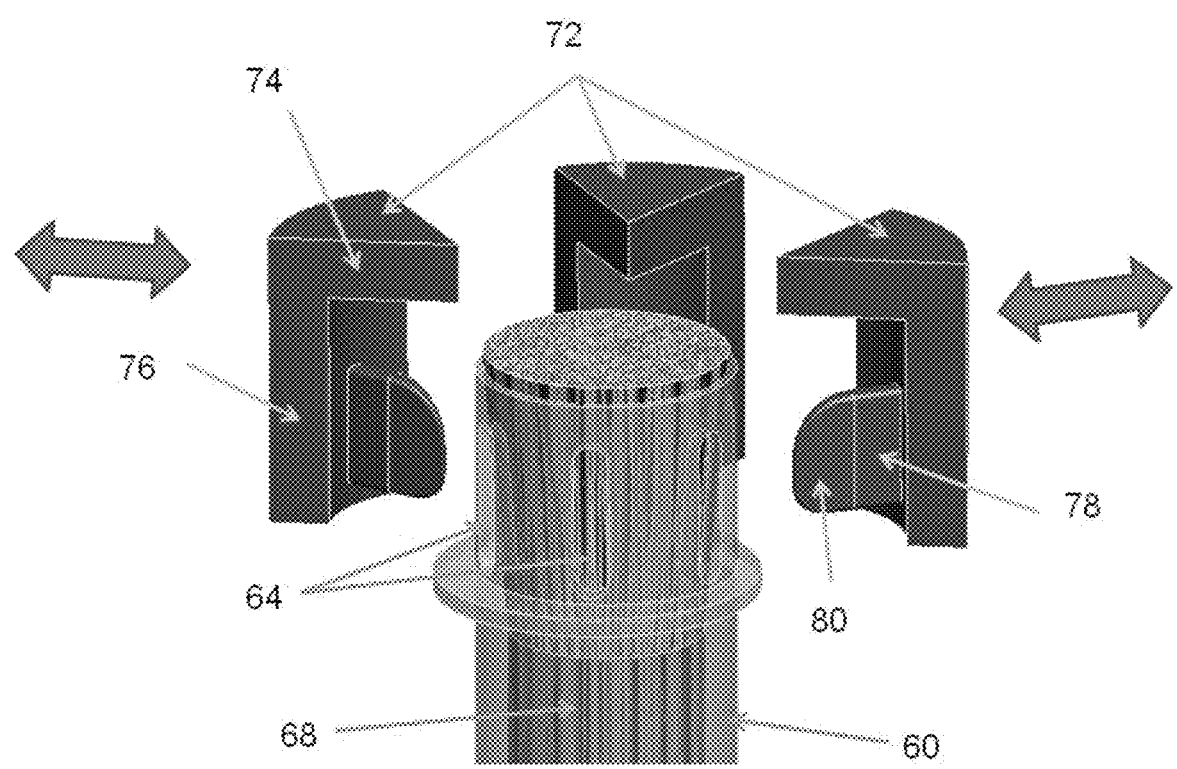
FIG. 9 is an oblique partial view of a housing, with fiber bundle in place, being introduced to potting tooling.

As illustrated in FIG. 9, into the filter assemblage of FIG. 8 are introduced a plurality of potting tool segments 72, each segment comprising a wedge shaped potting tool end segment 74, a potting tool cylinder segment 76, and a potting tool finger 78. (For clarity of illustration, the potting tool segments 72 are shown for only approximately half of the circumference of the fiber bundle.) Each potting tool finger 78 may have a potting tool finger tip 80.

The potting tool fingers 78 are illustrated as being solid entities. First of all, the potting tool finger 78 may have a surface that is smooth and may have edges that are rounded or tapered as appropriate for gently displacing fibers as the potting tool finger is advanced into the fiber bundle. However, in addition to what is illustrated, there also are other possible design features that could be used toward a goal of minimizing possible damage to the fibers. For example, it is contemplated that the potting tool finger could deliver flowing gas to the fiber bundle as the potting tool fingers are advancing into the fiber bundle to create the pattern of void flow channels. The gas could be delivered through small holes in the surface of the potting tool fingers. If this is done, the holes could be provided in the potting tool fingers in the region of the eventual inter fiber space, and not in the region of the potting tool that will be exposed to potting material. Alternatively, or in addition, it is possible that as the potting tool fingers are advancing into the fiber bundle, gas could be caused to flow in the inter fiber space along the axial direction of the fiber bundle. Another possibility is that the potting tool fingers could be made of multiple parts that separate from each other, such as by a hinge or by bending, after or while the potting tool fingers 78 are advanced into the fiber bundle. Not only can such process steps and features avoid damaging individual fibers, but they may present another advantage also. They may encourage the fibers to become uniformly spaced in the remaining space and shape of the fiber bundle, as opposed to having a "bunching-up" featuring an increased local packing density near the potting tool finger.

It is shown in FIG. 9 that proceeding in a radially inward direction, the potting tool finger 78 may be tapered to a thin edge that is rounded or radiused at its radially innermost tip. As illustrated, the potting tool finger 78 may extend radially inward more than half of a radial dimension of the fiber bundle but might end before it reaches a central longitudinal axis of the fiber bundle. Similarly, the void flow channels 82, which result from the positioning of the potting tool fingers and remain after potting, similarly may extend radially inward more than half of a radial dimension of the fiber bundle but might not extend entirely to a central longitudinal axis of the fiber bundle.

Each potting tool finger 78 also may have a taper with respect to an axial direction. As illustrated, the potting tool finger may taper so as to become thinner and eventually vanish in the direction toward the midplane or mid-region of the cartridge. The resulting void flow channel 82 created by the potting tool finger may have a similar tapering property and shape. Any edges of the potting tool fingers 78 may be contoured or radiused as desired, especially if they are located near or may contact fibers.

As illustrated, the number of potting tool segments and fingers is six. However, it can be appreciated that other numbers of potting tool segments and fingers are also possible. As illustrated, all of these features are distributed at equal angular intervals around the circumference of the fiber bundle. Such symmetry may be advantageous in achieving a uniform and rapid transition to a uniform axial flow where the axial component of the velocity vector is more than 70% or preferably more than 90% of the overall velocity vector, and the distribution of flow in the fiber bundle is substantially uniform. However, it can be understood that other patterns of positions of the potting tool fingers are also possible and symmetry is not essential.

Figure 10:
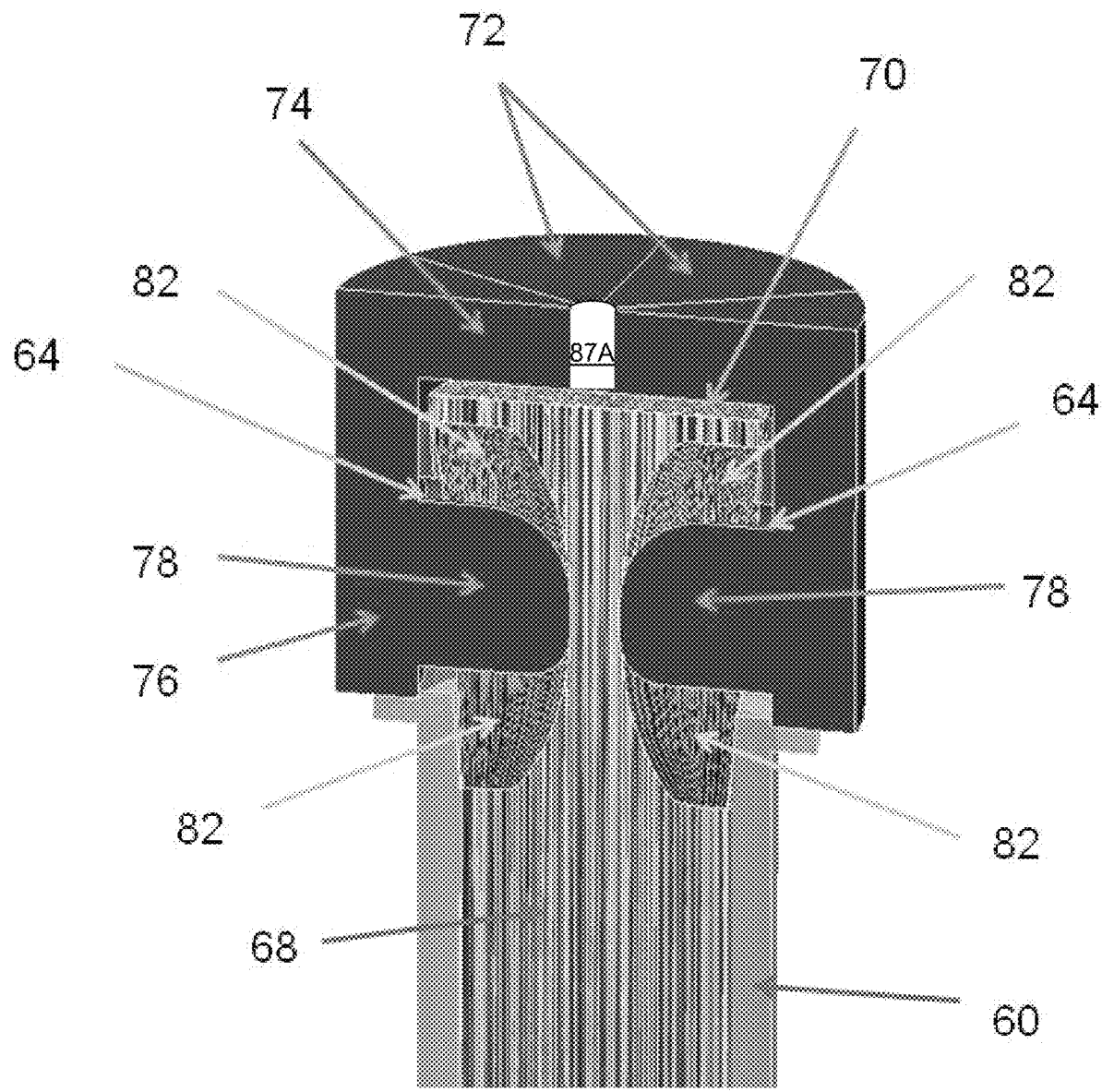
FIG. 10 is an oblique partial cross-sectional view of a housing, with fiber bundle in place, enclosed for potting.

The potting tool segments 72 shown in FIG. 9 are arranged to move radially inward so that when they meet they enclose the end of housing 60 as shown in FIG. 10. In FIG. 10, potting tool segments 72 have been moved inward radially to enclose the end of housing 60. (Again, for clarity of illustration, the potting tool segments 72 are shown for only approximately half of the circumference of the fiber bundle.) Potting tool end segments 74 have come together to form an enclosed space a short distance beyond the fiber ends 70 of fiber bundle 68. It can be considered that potting tool end segments 74 form a potting cap that contains and limits the flow of the resin during the potting process. The space inside the potting cap can be accessed through access port 87A. As illustrated in FIG. 10, potting tool fingers 78 have passed through radial ports 64 of housing 60, and into fiber bundle 68. Radial ports 64 may be dimensioned so as to allow potting tool fingers 78 to pass through them. The shape of radial ports 64 may be generally complementary to the shape of potting tool fingers 78 where potting tool fingers 78 pass through radial ports 64. Radial ports 64 may, for example, be rounded rectangles. Potting tool fingers 78 may locally displace fibers in fiber bundle 68 in a generally circumferential direction. Stiffness of the displaced fibers in fiber bundle 68 may result in the formation of separation patterns or void flow channels 82 in fiber bundle 68 that extend or continue for some distance immediately above and/or below potting tool fingers 78.

FIG. 11A shows the filter and potting tooling illustrated in FIG. 10, after injection and curing of a potting material 84. Potting materials are typically thermosetting materials which are injected into the potting tooling as a viscous liquid. Chemical reactions within the material then cause it to cross link and set into a relatively hard solid material. As illustrated in FIG. 11, potting material 84 may be injected until it fills a fiber void flow channel 82 that is near the end of the cartridge, fiber bundle interstitial space, and any additional space within potting tool segments 72, as far as a level depicted by line L-L. So, portions of the potting tool may serve as the potting cap that limits the spread of the resin during potting. The viscosity of the potting material 84, as it is injected, may be chosen such that the uncured potting material surrounds and conforms to the exteriors of the fibers but possibly does not enter the open fiber lumens to any great extent if the fiber lumens are open at their ends. It is furthermore possible that the ends of the fibers may have been sealed or closed prior to the potting operation.

Finger 78 may be tapered in such a way as to aid in removal of finger 78 from potting material after potting material has been cured, i.e., finger 78 may have a draft angle to aid in retraction of finger 78 from the potting material. The potting tool fingers can be made of a material that the potting material does not adhere to.

FIG. 11B shows another possible tooling arrangement, in which there is provided a potting cap 88 that is separate and distinct from the potting tool fingers 78. During the potting process, the potting cap 87 can serve to limit the flow of resin. After the resin has hardened, the potting cap 87 can be removed. The potting cap 88 may be reusable, such as for example by being made of a material that the potting material does not adhere to. In FIG. 11B, for clarity of illustration, the potting cap 88 is shown displaced upward from where it would normally be located. During use, the actual orientation would be such that potting cap 87 would be in contact with the corresponding surface of potting tool fingers 78. Potting cap 87 may have an inlet orifice 87A. The inlet orifice 87A may be such as to allow resin to be introduced into the potting cap and into the regions around the fibers that are to be potted.

As part of the potting process, centrifugation may be used. In such a process, the cartridge may be spun while the potting material is being introduced into the cartridge, while the potting material is curing, or both. The centrifugal force created by the spinning may urge the resin to the ends of the cartridge, where it can harden. Centrifugation can be convenient if both ends of the cartridge are of similar or identical design. In this way, both ends of the cartridge can be potted during a single manufacturing operation. The resin can, for example, be polyurethane. An alternative potting process would be by gravity driven potting, in which case the respective ends of the cartridge would have to be potted one end at a time.

Referring now to FIG. 12A, when potting material 84 has completely cured, the filter assemblage is removed from the potting tooling, and any potting material 84 and fiber bundle 68 extending beyond tube end 66 of housing 60 is cut away, thus re-exposing the lumens of the filter fibers. Polishing may also be performed. Because the fibers of fiber bundle 68 are now securely held in place by potting material 84, void flow channels 82 remain in fiber bundle 68 at least where the potting tool fingers had been, and radial channels 86 remain in potting material 84 in those locations that had been occupied by the potting tool fingers 78. It can be appreciated, as best seen in FIG. 12A and FIG. 13, that there can be both a void flow channel 82 in the fiber bundle and a radial channel 86 in a portion of the potting material 84, and these two features may be somewhat continuous with and in communication with each other. Both the radial channels 86 and the void flow channel 82 may be formed as space that is complementary to the potting tool finger 78.

It can further be appreciated, as illustrated in FIGS. 12A and 12B, that the pattern of rearrangement of fiber locations may extend through some extent of the potting material 84 in the axial direction, and may manifest itself at the surface of the potting material 84 that faces the end cap, i.e., faces away from the midplane of the cartridge. FIG. 12A shows a possible situation in which the disturbances in the fiber rearrangement, i.e., void flow channels 82, are slightly visible in the surface of potting material 84. It can be noted that the exposed surface exposing the lumens of the fibers would be a cut and polished surface, polished such that the lumens of the fibers are accessible for fluid communication with the lumens. In FIG. 12A, the void flow channel 82 is visible on that polished surface in the form of a narrow formation resembling a line, indicating that there is some but very little remaining influence of the pattern of rearrangement of the fibers due to the potting tool fingers 78.

FIG. 12B is similar to FIG. 12A but shows a possible pattern of fiber lumens at the outward-facing surface of the potting material 84 if the cutting and polishing of the potting material 84 were done a little bit closer to where the potting tool fingers 84 had been placed. In this situation, on the cut and polished surface, there could be identifiable regions containing substantially no fibers, and those regions could have shapes and positionings that would roughly resemble the shapes and positionings of the potting tool fingers 78. The pattern of fiber absence in the surface of the potting material 84 might possibly be narrower or less distinct than the shape of potting tool fingers 78, but would be more distinct or more visible than the pattern in FIG. 12A. The number of such shapes would be expected to be the same as the number of potting tool fingers 78. In FIG. 12B those regions containing substantially no fibers are illustrated as being triangular in shape, being wider at the outer circumference of the fiber bundle and tapering upon proceeding radially inward. This is based on the assumption that the potting tool fingers also have a shape that is at least somewhat triangular when viewed along the longitudinal axis of the cartridge.

It can be further appreciated that the pattern of void flow channels 82 due to rearrangement of fibers in the fiber bundle region may have some symmetry. For example, the fiber void flow channels 82 may be substantially equiangularly spaced around the circumference of the fiber bundle and may be substantially identical to each other. This illustrated pattern of the fiber void flow channels 82 may be advantageous in achieving a uniform and rapid transition and distribution of flow into the fiber bundle as uniform axial flow. However, it can be understood that other patterns are possible and symmetry is not essential.

It can be appreciated that there is a difference between the views of the potting material seen in FIGS. 12A-12B, and the views of the potting material seen in FIGS. 12C-12F. FIGS. 12A-12B illustrate outwardly-facing surfaces of the potting material. The term outward-facing refers to the fact that the particular surface faces outwardly away from the midplane of the cartridge. FIGS. 12C-12F illustrate inwardly-facing surfaces of the potting material, referring to the fact that the particular surface faces inwardly toward the midplane of the cartridge and toward the inter fiber space. The views of FIGS. 12C-12F include sectional cuts through the fibers.

FIG. 12C illustrates the appearance of an inwardly-facing surface of the barrier composed of the potting material 84. The inwardly-facing surface of the barrier faces the inter fiber space and the mid region of the cartridge. The surface visible in FIG. 12C is not polished, and actually has fibers protruding through it or emerging from it. It can be appreciated that in the view represented by FIG. 12C, and because of the manufacturing method illustrated involving the potting tool fingers 78, the surfaces that are visible in FIG. 12C might not all be coplanar with each other. Rather, in the illustrated cross-section, the visible surfaces that lack fibers may be recessed with respect to the visible surfaces that contain fibers. In regard to FIG. 12C, it can be explained that because FIG. 12C is a sectional view taken with a viewing direction as illustrated in FIG. 12A, the sectional cut cuts through the fibers so the view shows a cut surface of the fibers; but the radial channel is located at a different axial position with respect to the longitudinal axis of the cartridge, and so the sectioning plane would not actually cut through the potting material at the location of the radial channel. FIG. 12C illustrates the inwardly-facing surface of the potting material for the same construct as was illustrated in FIGS. 12A-12B.

In regard to FIGS. 12A-C, given potting tool fingers as illustrated, it would be possible, if the fill level of the potting material were chosen appropriately, to have the inward-facing surface of the potting material exactly match the corresponding surface of the potting tool finger or even have a gap between the potting material surface and the corresponding surface of the potting tool finger. In such a situation, there would be void follow channels 82 in the fiber bundle while there would not be any radial channel 86. However, in FIGS. 12A-B, the presence of radial channel 86 is illustrated, partly as a matter of manufacturing convenience.

Referring now to FIGS. 12D, 12E and 12F, there are shown additional possible sectional views with the same point of view and section definition as FIG. 12C. FIGS. 12D-12F illustrate still more possible patterns of fibers as the fibers emerge from the potting material. It can be appreciated that patterns similar to those of FIGS. 12D-12F could exist on the cut and polished outward-facing surfaces of the potting material, although the patterns might not be as pronounced as in FIGS. 12D-12F.

Referring now to FIGS. 12D and 12E, there are shown embodiments that would be created by potting tool fingers that are not all of equal size. Such a design is prompted by the realization that as the void flow channels proceed toward the interior of the fiber bundle, the void flow channels come closer to each other (i.e., closer than they are to each other near the outer circumference), and this close approach might not provide much additional benefit. Therefore, an alternative arrangement of the potting tool fingers would be an arrangement in which some of the potting tool fingers are one length and others of the potting tool fingers are another, different length. As illustrated, in such a situation, half of the potting tool fingers are longer and go more radially inward from the outer circumference, and the other half of the potting tool fingers are shorter and do not go as far radially inward from the outer circumference. For example, the longer potting tool fingers may extend more than half of the radial distance inward from the outer circumference, while the shorter potting tool fingers may extend less than half of the radial distance inward from the outer circumference. In FIGS. 12D and 12E, it is shown that the larger of the void flow channels come inward from the outer circumference by more than half of the radial dimension of the housing, while the smaller of the void flow channels come inward by a lesser distance than do the larger void flow channels. The smaller void flow channels come inward by less than half of the radial dimension of the housing. The longer void flow channels and the shorter void flow channels may alternate with each other, proceeding around the circumference of the fiber bundle. In FIG. 12D, such an arrangement is shown for a total of 8 void flow channels (4 large and 4 small). In FIG. 12E, such an arrangement is shown for a total of 12 void flow channels (6 large and 6 small).

FIG. 12F shows yet another possible arrangement of void flow channels. In this arrangement, the void flow channels are not generally straight in a radially inward orientation as they were in FIGS. 12A-12E. Rather, FIG. 12F shows that the void flow channels could be curved. Such curvature could create a situation in which the separation distance between adjacent void flow channels varies less strongly as a function of radius than is the case for the situation illustrated in FIG. 12A. The curving nature of the void flow channels (with the local slope of the outline of the void flow channel being closer to a tangential orientation near the outside of the fiber bundle and closer to a radial orientation further inward in the fiber bundle) may partially although not completely compensate for the changing size of the fiber bundle as a function of radius. Such void flow channels could be produced by potting tool fingers that are curved similarly to the illustrated void flow channels. Such potting tool fingers, if they are curved in the form of a circular arc as illustrated, could be swung into place by rotation around the respective centers of the respective circular arcs.

FIGS. 12A-12F mostly described patterns of fibers as visible on one or another surface of the potting. In addition, embodiments of the invention also pertain to the distribution of fibers in the inter fiber space near the potting. The spatial distribution of fibers may be non-uniform in a pattern that is intentional and is created when potting is performed, specifically, when the resin solidifies. Specifically, this pattern may feature fiber-free regions that correspond to flow void channels, and, in places other than the fiber-free regions that correspond to the flow void channels, these embodiments may feature may feature a relatively uniform distribution of fibers.

It can be noted that the distributions of fibers in three-dimensional space as discussed here, such as void flow regions, are built in to the fiber bundle and are not the result of random "clumping" of fibers as sometimes occurs in dialyzers (especially when the fibers of the dialyzer become wet on their outsides). In fact, cartridges of embodiments of the invention may be designed having features that are specifically intended to discourage the random "clumping" of fibers at places other than the intended void flow channels. Features that help to avoid random "clumping" of fibers include the use of wavy fibers and the use of specific void fractions as discussed elsewhere herein. The void flow channels may be created specifically as a result of the pattern of fibers where and when the fibers are immobilized at the place where the fibers enter the potting, at the time of hardening of the potting material.

The use of the potting tool fingers as already described may determine several geometric facts that may influence the long-term position of the fibers near the void flow channels. First, the potting tool fingers may determine the x-y location of the fibers at the place where the fibers emerge from the interior-facing surface of the potting material. (X-y refers to two Cartesian directions generally along a planar or almost-planar surface of the potting material.) Second, the potting tool fingers may determine the angle at which the fibers emerge from the interior-facing surface of the potting material. Commonly, this angle may be at least approximately parallel to the longitudinal axis of the cartridge, and such parallelism would especially be true if the surfaces of the potting tool fingers are substantially parallel to the longitudinal axis of the cartridge at or near the place where the potting tool fingers meet the interior-facing surface of the potting material. However, it is not absolutely necessary that the surfaces of the potting tool fingers, or the fibers themselves, be exactly parallel to the cartridge longitudinal axis at this location. Finally, the geometry of the potting tool fingers can help to determine the exact length of particular fibers from the emergence of the fiber at one potting end to the emergence of the same fiber at the other potting end. (This discussion does not consider possible waviness of the fibers.) Of course, this fiber length would nominally be the distance from the interior-facing surface of the potting at one end to the interior-facing surface of the potting at the other end. However, it would be possible for such fiber length to be slightly longer than the nominal distance, possibly influenced by the details of fanning of the fibers and also how the potting tool fingers displace the fiber. It can be appreciated that the distance to which the fiber bundle continues to exhibit the "disturbance" introduced by the potting tool features can be influenced by all of these factors, i.e., the x-y positioning of the emergence of any particular fiber from the potting, the angle of emergence of particular fibers from the potting, and the constrained length of a particular fiber. It can further be appreciated that the extent of the persistence of the "disturbance" in the fiber bundle also could be influenced to some extent by the stiffness or flexibility of the fibers, which would affect how they respond spatially to being displaced by the potting tool fingers. Yet another parameter that could possibly influence the positioning of the fibers in the potting might be how much extra length is provided for the fibers prior to potting and subsequent cutting-off of the fibers. This extra length could influence the positioning, especially the angular positioning, of the fiber ends. All of these parameters can be chosen so as to achieve a desired geometry of the void flow channel(s) in the fiber bundle.

It can be noted that the interior-facing surface of the potting may be idealized as a plane or may be at least approximately a plane. However, at a more exact level of detail, the interior-facing surface might have a slight curvature to it, especially if the potting process is a centrifugal potting process, and more particularly if the axis for spinning during the centrifugal potting process goes through the midpoint of the length of the cartridge, which would typically be the case if both ends of the cartridge are potted simultaneously.

By virtue of the potting, the position of the fibers immediately as they emerge from the potting is known. However, by the nature of the fibers being long and slender, the position of the fibers elsewhere in the inter fiber space is not so definite. More generally, as a description of the fiber placement in three-dimensional space within the fiber bundle, the pattern displayed on the potting interior-facing surface where the fibers emerge from the potting, may continue for some distance in the fiber bundle exhibiting void flow channels, but may eventually transition into a different distribution that may be more uniform than the pattern and distribution that exist immediately adjacent to the potting. This transition may happen together with a geometric fanning of the fibers. It is possible that the void flow channels may exist only in the fanning region of the fiber bundle, perhaps only in a portion of the fanning region of the fiber bundle. The unfanned region of the fiber bundle may have fibers that are substantially uniformly distributed.

To the extent that the geometry of voids and fibers near the cartridge end can be defined, and it is defined to at least some extent, the void flow channel, first of all, may have a principal direction that describes the path inward from the perimeter of the fiber bundle to wherever the void flow channel ends inside the fiber bundle or reaches most interiorly inside the fiber bundle. Additionally, the void flow channel may have a transverse dimension that is measured generally perpendicular to the principal direction of the void flow channel. The transverse dimension may generally be tapered, being greater at the perimeter of the fiber bundle and smaller more interiorly in the fiber bundle. Such tapering may be consistent with the expectation that as flow proceeds inwardly along the principal direction of the void flow channel, some of the flow would exit from the void flow channel into the fiber bundle adjoining the void flow channel. (This description applies to a flow inlet end of the cartridge; the opposite would be true at a flow exit or discharge end of the cartridge.) The void flow channel also may have a tapering in the axial direction proceeding away from the potting interior-facing surface. Such tapering may result from a natural tendency of the fibers to assume a more uniformly-spaced configuration, or from the fanning configuration of the fibers as imposed by the interior shape of the housing, or both.

Referring now to FIG. 12G, there is shown a combined illustration of how the local fiber porosity could vary as a function of position along the longitudinal axis of the cartridge, taking into account various features described herein. What is illustrated in FIG. 12G is most directly pertinent to the situation illustrated in FIGS. 12A, 12B and 12C, although in general such an illustration could be constructed representing any of the designs illustrated in FIGS. 12A-12F. What is plotted in FIG. 12G is the local porosity fraction within the fiber-occupied portions of the fiber bundle. The term "fiber-occupied portions of the fiber bundle" is intended to refer only to regions that do include fibers spaced near each other, while ignoring void flow channels if void flow channels are present.

The fiber bundle can be divided into three regions along the longitudinal direction of the cartridge, going from the midplane to an end of the cartridge, along with a fourth region that contains potting material. It can be pointed out that the central region of the cartridge, designated Region I, has a substantially uniform inside diameter of the housing and a substantially uniform packing fraction of the fiber bundle. The porosity in Region I can be referred to as the central porosity. Proceeding longitudinally away from the cartridge midplane, there is Region II, in which there is fanning of the fibers, i.e., the housing interior starts to taper so as to increase the internal cross-sectional area and the porosity fraction. In Region II there may be or there might not be influence of the potting tool fingers or the void flow channels created by the potting tool fingers. As illustrated In FIG. 12G, there is some influence in part of Region II and no influence in another part of Region II. The porosity in Region II can be referred to as the transitional porosity. At any given cross-section, this porosity can be considered to be the empty space between fibers not counting the identifiable void flow channels, divided by the space within the housing not counting the identifiable void flow channels. Thus, this porosity is essentially a descriptor of the distance of a fiber that is locally in a bundle configuration, to its nearest neighbor fibers. Next, there is Region III, in which there is both fanning of the fibers and the presence of the potting tool fingers and the associated void flow channels. The porosity of the fibers where the fibers emerge from the potting is the end porosity. It may be calculated just as the transitional porosity was calculated, omitting identifiable void flow channels.

There is also illustrated, in FIG. 12G, a Region IV that is inside the potting. This region does not affect the flow distribution in the inter fiber space, because in Region IV there is potting material rather than open space for fluid to flow. Nevertheless, the fanning of the fibers within the potting material can be expected to continue in approximately the same pattern exhibited in Regions II and III.

For the sake of a numerical example, this design may be discussed assuming that the porosity of the fiber bundle at the mid-region or midplane of the cartridge is 50%, and it may be assumed that at the mid-region or midplane the inside diameter of the cylindrical housing is 1 unit and the inside area of the cylindrical housing is 1 unit. Thus, the area occupied by the fibers would be 0.5 units and the void area also would be 0.5 units. This would describe the entirety of Region I up to the boundary with Region II. Further, it may be assumed that at the end of Region II, the inside diameter of the housing has increased to 1.1 units. Thus, the internal area has increased to 1.21 units, while the area occupied by the fibers remains at 0.5 units, so the area not occupied by the fibers would be 0.71 units. Thus, the porosity would be 0.71/1.21 or 59% if there is no spreading of fibers in Region II carried over from the potting tool fingers.

It may further be assumed that in Region III the tapering of the housing interior continues to increase so that at the end of Region III, the inside diameter is 1.2 units. Thus, the internal area would be 1.44 units, of which 0.5 units would be fiber cross-sectional area and 0.94 units would be empty space. So, if fibers were distributed throughout all of that space and there were no potting tool fingers or corresponding void flow channels, the porosity would be 0.94/1.44 or 0.65. However, it may be assumed that the potting tool fingers and the void flow channels created thereby occupy some space, which may be assumed to be 0.05 units. Thus, the actual empty space between fibers is 1.44−0.50−0.05 or 0.89 units. So, the porosity fraction would be 0.89/1.44, or 0.62. It can be seen with this numerical example that in Region III as one proceeds from the boundary between Region II and Region III, the porosity continues to increase toward the end of the cartridge, but only slightly. How much the porosity increases and, whether it increases at all, depends on the size of the potting tool fingers and the void flow channels. This illustrates that the size of the potting tool fingers can have an important influence on the local porosity of the fiber bundle. The porosity just calculated for Region III is for the fiber bundle of Region III omitting the void flow channels. The void flow channels are omitted from the calculation because the void flow channels are intended to serve an entirely different purpose, namely distributing flow easily from place to place within the cross-section of the fiber bundle. For present discussion the porosity fraction is intended to be illustrative of the local conditions of blood flow among fibers in the inter fiber space. This could be thought of as an analogy between local flow among the fibers and local flow through a porous medium, for which local porosity among the fibers would be an important descriptive parameter. For example, if the potting tool fingers were larger than just assumed, they might make the porosity of Region III where fibers are spaced next to each other smaller than desired. Indeed, if the assumed amount of space devoted to the void flow channels was a few percentage points larger than just assumed, it could make the porosity of Region III smaller than the porosity of Region II. The void dimensions and the geometry of the fanning-out of fibers may be related such that the local porosity fraction within the fiber-occupied portions of the fiber bundle is either constant or increases continuously from mid-cartridge out to the end of the cartridge. For example, it may be desirable to have the inside diameter of the housing near its end increase to a value that is larger than the factor of 1.2 that was just assumed. In Region IV, the fibers may continue along the trajectory that they had in Region III and may have substantially the same slope as in Region III, but the fibers are potted in the potting material. In Region IV, there is no flow past the outsides of the fibers.

Referring now to FIG. 13, the filter assemblage of FIG. 12 may be completed by adding a dialysate cap 88, which may be bonded to the end of housing 60 along circumferential cap-tube joint 94, and then by adding sleeve 96, which may be bonded to cap flange 92 along circumferential sleeve-cap joint 100, and also bonded to tube flange 98 along circumferential sleeve-tube joint 102. Sleeve 96, cap flange 92, tube flange 98, and the exterior of housing 60 may form a circumferential distribution channel to distribute a patient's blood (or to distribute other fluid) uniformly to a plurality of radial openings comprising radial ports 64, void flow channels 82 and radial channels 86. Alternatively, other designs could also provide a circumferential distribution channel and appropriate joining of parts.

This cartridge as constructed may have the property that it may provide a plurality of unobstructed radially oriented flow channels such as void flow channels 82 that provide a flowpath in a generally radial direction to allow flow to readily penetrate radially into the interior of fiber bundle 32. It is expected that as a result of the presence of the void flow channels 82, the overall flow entering the fiber bundle can transition to a uniform axial flow within the fiber bundle 32, within a much smaller region or axial distance than would be required for the simpler cartridge depicted in FIG. 6. In the configuration illustrated in FIG. 13, if there occur any regions within the fiber bundle having stagnation or low flow velocities, it can be expected that the size of such stagnation or low flow regions will be much smaller than would occur in a prior art cartridge. If similar geometry is provided at the exit or discharge end of the cartridge, similar behavior can also be expected at that end.

For understanding geometric proportions and relationships, it may be understood that the fibers in the fiber bundle may have an average fiber-to-fiber spacing at a mid-region of the cartridge, such as midway between the two ends of the cartridge. In the void flow channels 82, near an end of the cartridge, the fiber bundle may contain at least one substantially open void flow channel 82 that has a transverse dimension, at at least some location, that is at least 5 times the average fiber-to-fiber spacing that occurs at the mid-region of the cartridge. The void flow channel may have a transverse dimension, at at least some location, that is at least 3 times the average fiber-to-fiber spacing that occurs at the mid-region of the cartridge, or at least 5 times, or at least 10 times the average fiber-to-fiber spacing that occurs at the mid-region of the cartridge.

It can further be understood that at the place where fibers emerge from the potting to become the fiber bundle, the void flow channel is well defined because the location of the fibers is well defined by the potting. As one proceeds away from the end of the cartridge and the potting, and approaches relatively closer to the middle of the cartridge, the void flow channel 82 may become narrower or less well defined because the fibers have some flexibility and there is some opportunity for the fibers to rearrange themselves more uniformly. As distance away from the potting increases, the influence of fiber position at the potting, as determined by the positions of the potting tool fingers 84 in arranging the positions of the fibers, can be expected to diminish. The distribution of the fibers as a function of distance away from the potting may also be influenced by the shape (e.g. taper) of the potting tool fingers 84. Indeed, it may be desirable that in most of the middle region of the cartridge occupying a large fraction of the length of the cartridge, except for void flow channels 82, the fiber bundle be substantially uniformly distributed within the housing. It is believed that, other than at the transition region that includes the tapered housing interior and the void flow channels 82, it is desirable to have substantially uniform distribution of fibers within the housing.

It is possible that the fiber void flow channel 82 could be tapered in the radial direction, being wider near the outer circumference of the fiber bundle and narrower closer in toward the longitudinal axis of the fiber bundle. This can be understood from the shape of the potting tool fingers 78 illustrated in FIG. 9, which cause the fibers to be distributed so as to form the void flow channel 82. It is further possible that the void flow channel 82 can be tapered in the axial direction, being wider near the potting material and narrower away from the potting material. This also can be understood from the shape of the potting tool fingers 78 illustrated in FIG. 9. It can be seen in FIG. 9 that the potting tool fingers 80 are wider closer to the end of the cartridge and taper to a sharper shape having relatively narrow thickness at a location closer to the midplane of the cartridge and the fiber bundle.

As further examples of possible numerical parameters, in embodiments of the invention such as this first embodiment, the length of cartridge can be in the range of approximately 150 mm to approximately 300 mm or slightly longer. The total surface area of the hollow fiber membranes can range from 0.1 $m^2$ (which might correspond to a dialyzer for pediatric hemodialysis) to 3 $m^2$ (which would be at the upper end of the range of dialyzers for adult hemodialysis). The outside diameter of the housing (at or near the midplane of the cartridge) may vary in the range of approximately 20 mm to approximately 50 mm. If a cartridge at its midplane has an inside diameter of 35 mm, then the internal cross-sectional area of the housing is about 960 $mm^2$.

The fanning angle of the fibers, where fanning exists, could be in the range of 5 to 15 degrees, perhaps typically 10 degrees. This angle represents the slope of the outermost fiber relative to the centerline of the cartridge. The ratio of the cross-sectional area of the fiber bundle at ends of the fiber bundle, relative to the cross-sectional area at the start of fanning of the fibers, depends on the fanning angle and also on how long the fanned region is. Such area ratio could be in the range of 1.1 to 1.7.

The length of the end region of the cartridge (including fanning, and the features that make up an orbital distributor, and the dimensions of the potting tool fingers) could be such that approximately 10% of the overall length of the cartridge may be allocated to an end transition region at one end of the cartridge, and another 10% of the overall length of the cartridge may be allocated to an end transition region at the other end of the cartridge, and the remaining 80% of the overall length of the cartridge may be allocated for the middle region that is uniform and of constant cross-section, or nearly uniform and of nearly constant cross-section. Corresponding actual dimensions could be a length of 30 cm for the middle region and 2.5 cm to 3 cm for each of the end regions. Of course, these dimensions could be varied as desired.

In regard to the potting tool fingers, if it is assumed that there are six such fingers and they have an extent of 2 mm along the circumference of the fiber bundle, and the voids are triangular extending inward for half of the radial dimension of the fiber bundle, and if the diameter of the fiber bundle is 40 mm, then the total cross-sectional area of the six of them would occupy about 5% of the cross-sectional area of the fiber bundle. This is approximately what was assumed in hypothetical calculations discussed in connection with FIG. 12G.

It might be considered that a channel whose entrance is 2 mm wide is not as wide as might be desired, in view of various flow properties of blood. Accordingly, additional possible dimensions and dimensional combinations are presented here. In another possible set of dimensions, the diameter of the fiber bundle at the cartridge midplane might be 4 cm and the diameter of the fiber bundle at the potting might be 5 cm. Compared to the previous example, this numerical set of fanning parameters gives a somewhat greater expansion providing space for larger void flow channels. These two diameters provide a diameter ratio of 1.25 and an area ratio of 1.56. The cross-sectional area of the fiber bundle at the midplane is 12.56 cm2, and the cross-sectional area of a 5 cm diameter circle is 19.6 cm2, which is 7 cm^2 greater than the midplane cross-sectional area. If there were six void flow channels of triangular cross-section, and the base of each triangle were 1 cm measured along the circumference of the fiber bundle and the height of the triangle were 2 cm extending radially into the fiber bundle (compared to a fiber bundle radius of 2.5 cm at the location of the void flow channels), then the area of each such triangle would be 1 cm2 and the total area of the six void flow channels would be 6 cm2. This 6 cm2 total cross-sectional area of the void flow channels is about 30% of the assumed total cross-sectional area of the fiber bundle at the end. This would leave (19.6 cm2–6 cm2) or 13.6 cm2 of cross-sectional area for actual fiber bundle, which still is larger than the unfanned cartridge cross-sectional area of 12.56 cm2 at the midplane. So, even with some cross-sectional space being devoted to void flow channels, the fiber spacing in the actual grouped fibers still exhibits some fanning, i.e., some increase in local porosity or void fraction compared to the spacing of the fibers at the cartridge midplane. This is believed to be desirable. Of course, still other combinations of dimensions could be envisioned. For example, the circumferential dimension of a void flow channel at the outside circumference might be in the range of 3 mm to 10 mm, more specifically 4 mm to 7 mm. Choice of this dimension could be influenced by whether the fluid intended to be flowing in the inter fiber space is ordinary blood, anticoagulant-treated blood, or dialysate.

Still further discussion of fanning properties can be given here. The fanning angle of the outermost fibers in a fiber bundle may be in the range of 5 to 15 degrees, typically somewhere around 10 degrees. A typical diameter of a fiber bundle is 4 cm for sake of example. The length of the fanning region at any individual end of the cartridge can be in the range of 1 cm to 2.5 cm. This can provide an increase in diameter of the fiber bundle of from an initial 4 cm diameter to a final 4.2 cm diameter, or a final 4.4 cm diameter, or even a final 5 cm diameter. The fanning may be defined at least partially by an internal shape of the housing. The fanning does not have to be strictly a cone but could be any shape that provides gradual enlargement of cross-section as a function of distance along the longitudinal axis of the cartridge. Fanning can be described by a geometric fanning factor, which may be simply determined by the housing interior geometry such as by diameter ratios. For example, a diameter ratio of 1.25 to 1 gives a geometric fanning factor of 1.56, as discussed. In embodiments of the invention, the geometric fanning factor may be generally in the range of 1.1 to 1.7, more specifically in the range of 1.3 to 1.6. There may also be calculated a void-adjusted fanning factor. A void-adjusted fanning factor may describe the gradual change of the flow situation representing flow between neighboring fibers. For example, if there is geometric fanning but essentially all of the increase in cross-sectional area is devoted to void flow channels, then the actual spacing between neighboring fibers would not change and this fact would be represented by the void-adjusted fanning factor. The void-adjusted porosity at the end, adjacent to the potting material, may be defined as (total cross-sectional area of fiber region excluding void flow channels, minus total cross-sectional area of fibers), divided by (total cross-sectional area of fiber region excluding void flow channels), This may be compared to the porosity at the midplane. In embodiments of the invention, the void-adjusted porosity at the end may be greater than the midplane porosity by a factor of at least 1.1, or at least 1.2, or 1.3, or 1.4.

Regarding materials of construction, for the housing, polycarbonate and polypropylene are commonly used. For the potting material, a common choice is polyurethane. The hollow fibers can be made of any of various polymeric materials that are known for use in such fibers. Examples include polyethersulfone in combination with polyvinylpyrrolidone; polyacrylonitrile; cellulose triacetate; polyether polymer alloy polymethylmethacrylate; and other substances.

In the first embodiment as just described, the discussion has been presented as applied to the configuration in which blood flows in the inter fiber space and dialysate flows in the fiber lumens. It is appropriate, for this configuration, to pay especially close attention to the flow field of liquid, i.e., blood, flowing in the inter fiber space. The reason is that blood has a preferred range of shear rate and shear rate gradient. Some phenomena to be avoided are blood forming clots, and leukocytes segregating out from the flow. Specifically, it has been observed experimentally, with blood flowing in the inter fiber space, that the location where clots are most likely to form in the entire cartridge is at the first few layers of fibers where the blood enters the fiber bundle from the orbital distributor. It is believed (although it is not wished to be limited to this explanation) that the tendency for clots to form at that particular location may be related to the sharp change of shear rate experienced by the blood as the blood leaves the relatively wide open channel flow of the tubing and the orbital distributor, and enters the narrow interstices of the inter fiber space. It is further believed (although not wishing to be bound by this theory) that if there is a transition of local porosity as a function of position generally along the flowpath, this will provide a more favorable condition for blood flow to be introduced into the fiber bundle thereby avoiding clotting and sequestration of leukocytes.

It also can be kept in mind that this embodiment, and generally the various embodiments herein, are in general a vehicle for providing a more uniform and rapidly-equilibrated flow of liquid in the inter fiber space. The first embodiment provides a transition from flow entering through a side port, to generally axial flow in a majority of the length of the cartridge. The liquid in the inter fiber space does not have to be blood. If desired, that liquid flowing in the inter fiber space could be dialysate, instead of blood. Even for conventional dialysis systems in which the inter fiber space contains dialysate, it is known that the problem of achieving truly uniform flow of dialysate has not been completely solved in the prior art, and the nonuniformity of dialysate flow has an unfavorable impact on the efficiency and clearance of the dialyzer simply. Accordingly, it is possible to use embodiments of the invention in a configuration such that dialysate flows in the inter fiber space, simply for the purpose of improving the uniformity of that flow of dialysate.

It is believed that having the porosity continuously decreasing upon progressing along the longitudinal direction is useful for the situation where blood flows in the inter fiber space. This is because experimentally there has been some observation of clotting occurring at the entrance to the fiber bundle from an orbital distributor. The ratio of maximum porosity in the end region, to the mid-region porosity, may be chosen so as to achieve desired results in such regard as avoiding the formation of blood clots in the inter fiber space (if blood is the fluid flowing in the inter fiber space). This may be done by achieving a desired shear rate or shear rate gradient for the blood flow at the entrance to the inter fiber space. The orbital distributor used with the cartridge may be of any desired design, such that it serves to distribute the flow to substantially the full circumference of the fiber bundle.

Overall, a description of the lengthwise features of the cartridge may be such that approximately 10% of the overall length of the cartridge may be allocated to an end transition region at one end of the cartridge, and another 10% of the overall length of the cartridge may be allocated to an end transition region at the other end of the cartridge, and the remaining 80% of the overall length of the cartridge may be allocated for the middle region that is uniform and of constant cross-section, or nearly uniform and of nearly constant cross-section.

Embodiment 2

A second embodiment of the invention is illustrated in FIGS. 14-18. The completed cartridge of this embodiment is depicted in FIG. 18. Methods of manufacturing such a cartridge are illustrated in FIGS. 14-17A. Much of the discussion about void flow channels from the first embodiment also applies to the second embodiment, with the difference being a change of the geometric orientation by which the void flow channels approach the fiber bundle. In this embodiment, the flow into the inter fiber space is introduced in a generally axial direction. Thus, the equilibration of this flow may require some spreading out from the point(s) of introduction, but there is no overall large change of direction of this flow. This lack of change of direction of the flow is a contrast to what was present in the first embodiment (in which the flow underwent a directional change of approximately 90 degrees). It can be appreciated that in this second embodiment, the introduction of the flow that goes through the inter fiber space, and introduction of the flow that goes through the lumens of the fibers, are in flow directions that are substantially aligned with each other.

As discussed in connection with the first embodiment, it is again believed that in order to avoid clotting and other undesirable phenomena with regard to introducing blood flow into the inter fiber space (if blood is the fluid flowing in the inter fiber space), it is desirable to minimize sudden change in the shear rate of the flowing blood.

A cartridge of this embodiment of the invention may be constructed in accordance with the following steps.

Referring now to FIG. 14, a housing 106 may have a tapered end portion, and may be filled with a fiber bundle 112. This internal taper is favorable for creating fanning of the fibers near the end of the cartridge. FIG. 14 shows a housing that is internally tapered near an end, but on the outside is generally cylindrical. Discussion in connection with FIGS. 7A and 7B is also applicable here. It would also be possible for the housing 106 to be internally tapered and externally tapered similar to what was shown in FIG. 7B. Preferably, at this stage, fiber ends 114 extend a short distance beyond housing end 110 of housing 106. The fibers may have already had their ends closed, or the fibers may be subjected to a closing operation at this stage of the manufacturing process.

In FIG. 15, a potting cap 116 may be applied to the filter assemblage of FIG. 14. A circumferential potting sleeve 118 may then slip over the outside of housing 106. Potting cap 116 may contain a receiving orifice and manifold 140 for receiving potting resin and distributing it throughout the region that is to be potted. A potting cap end 120 may be positioned a short distance beyond filter fiber ends 114. Potting cap end 120 may support a plurality of fiber displacement fingers 122. Fiber displacement fingers 122 may comprise a finger shoulder 124 having a substantial diameter, and may comprise a finger extension 126 having a lesser diameter. Finger extension 126 may preferably be tapered, for example, conical, and may end in a blunt tip 128. Fiber displacement fingers may be advanced in a longitudinal direction with respect to the overall cartridge. Potting tool fingers in Embodiment 1 and fiber displacement fingers in Embodiment 2 could generally be referred to as fingers or displacers, because of their role in displacing the positions of fibers near them. As discussed in connection with another embodiment, it is possible for the fiber displacement fingers 122 to deliver a flow of a gas before, while or after they are being advanced into the fiber bundle. It is also possible that gas could be caused to flow through the fiber bundle itself as these operations take place. As discussed, not only can such process steps and features avoid damaging individual fibers, but they may present another advantage also. They may encourage the fibers to become uniformly spaced in the remaining space of the fiber bundle, as opposed to having a "bunching-up" featuring an increased local packing density near the potting tool finger.

As discussed in connection with another embodiment, the viscosity of the potting material 180, as it is injected, may be chosen such that the potting material 180 enters the open fiber lumens only to a minimal distance. It is furthermore possible that the ends of the fibers may be sealed prior to the potting operation. For example, the fiber bundle may be cut to length by a laser cutting operation that also leaves the ends of the fibers closed shut as a result of the heat involved in the cutting process. When potting material 180 is fully cured, the potting cap 116 may be removed.

Fiber displacement fingers 122 may displace filter fiber ends 114 radially from fiber displacement fingers 122, the extent of that displacement being defined by the diameters of finger shoulders 124. As the fibers of fiber bundle 112 are somewhat stiff, void flow channels 130 are created within fiber bundle 112, around finger extensions 126, both adjacent to and immediately below finger shoulders 124.

Referring now to FIG. 16, potting material 132 may be introduced until void flow channels 130, filter fiber interstitial space, and any additional space within potting cap 116 is filled as far as a level depicted by line L-L. The viscosity of the potting material 132, as it is injected, may be chosen such that the material enters the open fiber lumens only to a predetermined minimal distance.

Referring now to FIG. 17A, when potting material 132 has completely cured, potting cap 116 may be removed from the filter assemblage, and any potting material 132 and fiber bundle 112 extending beyond tube end 110 of housing 106 may be cut away, thus re-exposing the filter fiber lumens. Because the fibers of fiber bundle 112 are now rigidly held by potting material 132, void flow channels 130 remain in fiber bundle 112, and axial channels 134 remain in potting material 132 in those locations where fiber displacement fingers 122 previously resided. The void can be tapered in the axial direction, being wider near the potting material and narrower away from the potting material. This can be understood from the shape of the potting tool fingers 122 and finger extensions 126 illustrated in FIG. 16. Again, the void flow channel in the fiber bundle may be such that the void flow channel, at at least at some location, has a transverse dimension that is at least 3 times, or at least 5 times the average fiber-to-fiber spacing at the mid-region of the cartridge. The void flow channel in the fiber bundle may be such that the fiber void flow channel, at at least at some location, has a transverse dimension that is at least 3 times, or at least 5 times, or at least 10 times or at least 20 times the average fiber-centerline-to-fiber-centerline spacing at the mid-region of the cartridge. The transverse dimension of the void flow channel can be tapered along the principal direction of the void flow channel, similar to the tapering of the void flow channels in the first embodiment. An actual transverse dimension of the void flow channel or an actual transverse dimension of the potting tool finger 122 or finger extension 126 may range from one to several millimeters at a narrower end, to approximately 3 to 10 millimeters at the potting material. The length of the fanning region may be similar to the length of the fanning region discussed in Embodiment 1, such as a distance of 1 to 2.5 cm. Parameter ranges for the geometric fanning factor and the void-adjusted fanning factor may be similar to those for Embodiment 1.

Referring now to FIG. 17B, the fiber bundle can be divided into three regions along the longitudinal direction of the cartridge, going from the midplane to an end of the cartridge, along with a fourth region that contains potting material. It can be pointed out that the central region of the cartridge, designated Region I, has a substantially uniform inside diameter of the housing and a substantially uniform packing fraction of the fiber bundle. Proceeding longitudinally away from the cartridge midplane, there is Region II, in which there is fanning of the fibers, i.e., the housing interior starts to taper so as to increase the internal cross-sectional area and the porosity fraction. In Region II as illustrated there is no influence of the potting tool fingers or the void flow channels created by the potting tool fingers. As illustrated In FIG. 17B, there is some influence in part of Region III and no influence in another part of Region III. Next, there is Region III, in which there is both fanning of the fibers and the void flow channels created by the potting tool fingers. There is also shown Region IV, in which the fibers may continue along the trajectory that they had in Region III and may have substantially the same slope as in Region III, but are potted in the potting material. In Region IV, there is no actual flow past the outsides of the fibers.

Referring now to FIG. 18, to complete the construction of this second embodiment of a cartridge, distributor plate 138 may be first inserted into filter cap 136, and may be bonded along circumferential distributor-cap joint 142. Filter cap 136 may then be assembled to housing 106, and may be bonded along circumferential cap-tube-joint 144, with distribution tubes 140 inserted into axial channels 134 of potting material 132. Sealing at distributor tube-channel joints 146 may be achieved either by inserting the tapered distribution tubes 140 into the tapered axial channels 134, with sufficient force, or by the use of a bonding agent. Tapered distribution tubes 140, or potting material 132, or the combination of them, may be chosen so as to provide sufficient softness or dimensional properties of at least one of those materials so as to create a seal for keeping the blood and the dialysate compartments separate and isolated from each other.

Blood, entering blood inlet/outlet 150 of filter cap 136, flows through distribution tubes 140, through axial channels 134, into void flow channels 130 in fiber bundle 112, where it enters the interstitial spaces between fibers in fiber bundle 112, establishing a uniform axial flow within a short distance. With the provision of a plurality of axial channels 134 as described and illustrated, any possible areas of low flow velocity, or stagnation, within fiber bundle 112 can be expected to be small and limited.

As illustrated, the axial channels 134 may be provided in a quantity and in a geometric arrangement such that there are seven axial channels 134. One of the axial channels 134 is centrally located substantially coinciding with the longitudinal axis of the cartridge, and the other six axial channels 134 are arranged in a hexagon-like distribution surrounding the central axial channel 134. Such an arrangement provides a useful symmetry and good packing or spacing properties of the axial channels 134. It is believed that this is helpful for achieving a nearly-uniform velocity over the entire cross-section, and achieving it within a short distance. It can be appreciated that, alternatively, other numbers and patterns of axial channels 134 could be provided, subject to practical manufacturing considerations and other considerations.

Dialysate entering dialysate inlet/outlet 148 readily flows into and through the lumens of the fibers of fiber bundle 112. As illustrated, the dialysate inlet/outlet 148 could be used in such a way that dialysate could flow in either of two possible directions with respect to the blood flow. Thus, the relative flow of the blood and the dialysate could be either co-flow or counter-flow, as desired.

In both the first and second embodiments as just described and illustrated, the flow direction of the blood and the flow direction of the dialysate could be either counterflow (blood flow and dialysate flow are opposite to each other) flowing generally parallel to each other but in directions that are the opposite of each other) or co-flowing (parallel and flowing generally the same direction as each other).

Embodiment 3

A third embodiment, illustrated in FIGS. 19 to 24, provides yet another way to achieve uniform flow distribution in the inter fiber space. Whereas the first two embodiments attempted to mitigate the effects of non-uniform blood flow in the interstitial space between the fibers of a fiber bundle, by providing means to channel the blood into the interior of the fiber bundle in close proximity to the potting material used to encase the fiber ends and creating flow of fluid (blood) along the longitudinal (axial) direction of the fibers, in contrast this third embodiment utilizes a yet another flow pattern to achieve uniformity. In this embodiment, the flow of fluid (blood) in the inter fiber space is generally perpendicular to the fibers generally everywhere in the cartridge.

Referring now to FIG. 19, there is shown filter base 152, used in the construction of a flat cross-flow filter cartridge. Filter base 152 comprises a filter base plate 154, with upstanding side walls 156 rising from opposing side edges of filter base plate 154. Upstanding end walls 158 extend a short distance from side walls 156 along opposing top and bottom edges of filter base plate 154. Inlet/outlet ports 160 are positioned on sidewalls 156. Upstanding flow diverters 162 are located on filter base plate 154, adjacent inlet/outlet ports 160, and are used to spread incoming flows entering distribution chambers 164.

Additionally, as shown in FIG. 20, there may be provided a screen 170. Such screen 170 may be helpful for maintaining the fibers in generally the region in which it is intended that they be located. Screen 170 also may be helpful in causing the flow to be distributed as desired. Screen 170 may take the form of a wire mesh screen, or alternatively may be a portion of a perforated sheet material. Screen 170 may be supported at its ends by screen support ribs 166 extending from end walls 158 support and capture one end of screen 170. Screen support grooves 168 in filter base plate 152 may support and capture the edges of screen 170.

As shown in FIG. 21, a rectangular fiber bundle 172, having a bundle cross-sectional shape that is generally rectangular, may be placed on filter base plate 154, between screens 170. At this stage of manufacture, fiber ends 174 may preferably extend a short distance beyond end walls 158.

As shown in FIG. 22, after this step, cover 176 (which is shown as being semi-transparent) has been placed on top of upstanding side walls 156 and upstanding end walls 158. Screen support grooves (not shown) in the underside of cover 176 may support and capture the top edges of screens 170. Cover 176 may be bonded to the tops of upstanding side walls 156 and upstanding end walls 158 by means of solvent welding, adhesive bonding, ultrasonic welding, or other suitable means.

Referring to FIG. 23, the filter assemblage of FIG. 22 then may have potting caps (not shown) applied to both filter ends 178, and potting material 180 may be injected, to fill all available free space and fiber interstitial space to a distance indicated by lines L-L. As discussed herein in connection with another embodiment, the viscosity of the potting material 180, as it is injected, may be chosen such that the potting material 180 enters the open fiber lumens only to a minimal distance. It is furthermore possible that the ends of the fibers may be sealed prior to the potting operation. For example, the fiber bundle may be cut to length by a laser cutting operation that also leaves the ends of the fibers closed shut as a result of the heat involved in the cutting process. When potting material 180 is fully cured, the potting caps may be removed.

As shown in FIG. 24, the filter construction may be completed by first cutting away excess potting material 180 and any fiber bundle protruding beyond end walls 158, thus re-exposing the filter fiber lumens. This operation, as illustrated on the lower end of the filter in FIG. 24, may be performed on both ends of the cartridge. Finally, as illustrated on the upper end of the cartridge in FIG. 24, a dialysate cap 182 may be applied to each end of the cartridge, and may be bonded along the entire dialysate cap bond edge 188, by solvent welding or other suitable means. It can be noted that, for ease of illustration, FIG. 24 only shows half of the fiber bundle with respect to the direction of blood flow. The remaining half, as defined by a sectioning plane along a central plane of symmetry of the cartridge, is omitted. Also, FIG. 24 shows one dialysate cap but, for ease of illustration, does not show the second dialysate cap.

Dialysate entering dialysate inlet/outlet port 184, may be approximately evenly distributed in dialysate header 186 formed between dialysate cap 182 and filter end 178, then may flow as indicated through the lumens of fiber bundle 172. At the opposite end of the filter, the dialysate may collect in the header of the second dialysate cap (not shown), and may exit through the second inlet/outlet port.

Blood from a patient may be introduced through inlet/outlet port 160, and may be steered by flow diverter 162 into both halves of distribution chamber 164, where it may transition into a uniform flow normal to screen 170, passing through the first screen 170, through the interstitial space in fiber bundle 172, in the direction indicated, in the rectangular space defined by filter base plate 154, cover 176, and potting material 180 at both ends 178 of the filter.

At the other end of the cartridge, similarly to the flow pattern for the end that is illustrated herein, blood may then pass through the second screen (not shown), collect in the second distribution chamber (not shown), and exit through the second inlet/outlet port (not shown).

In this embodiment, given that the blood flow is directed through the filter fiber interstitial space in a direction perpendicular to the fiber axes, it is possible to design an inlet distribution structure that transitions the blood flow to a uniform flow, without stagnation areas, before the blood enters the fiber bundle. A similar structure at the outlet end can collect blood leaving the fiber bundle.

Embodiment 4

Yet another embodiment of the invention, which is a fourth embodiment, is illustrated in FIGS. 25-32. In this embodiment, the flow past the fibers again is generally perpendicular to the fibers. More specifically, the cartridge in this embodiment has a generally axisymmetric geometry and the flow flows past the fibers in a generally radial direction with respect to the overall generally axisymmetric geometry. In order to achieve the generally radial flow past the fibers, there may be provided a central void 232 (FIG. 31) forming a channel that extends generally along the longitudinal axis, which may conduct blood in an axial direction until the blood transitions to a radially outward flow direction flowing past the fibers. On the outside of the fiber bundle, there may be a fluid collection space in the form of a radial filter screen, which allows fluid that exits from the fiber bundle to collect and transition toward the outlet of the housing. (This description is given assuming that blood enters the fiber bundle along the axis and exits the fiber bundle at the outside circumference of the fiber bundle. The opposite is also possible.

Referring now to FIG. 25, there is shown a filter screen used in the construction of this embodiment. This screen may comprise an inner wire 192, which may be formed into a helix, and a plurality of longitudinal wires 194. Inner wire 192 is preferably a small diameter wire, wound with a large spacing of the helical turns. Outer wires 194 may preferably be larger diameter wire, and may be joined to inner wires 192, on the outside of the helix, to form a radial filter screen 190 having a substantial free area for flow in the axial direction.

Referring now to FIG. 26, there is shown a fiber bundle 198 that is inserted into radial filter screen 190. The length of fiber bundle 198 is preferably greater than the length of radial filter screen 190, such that fiber bundle ends 200 extend a moderate distance beyond screen ends 196.

As shown in FIG. 27, radial filter screen 190 and fiber bundle 198 may be inserted into housing 202. Housing 202 is preferably of a length midway between the length of axial filter screen 190 and fiber bundle 198, such that axial filter screen 190 is entirely within housing 202, whereas both fiber bundle ends 200 extend a short distance beyond housing ends 204.

In FIG. 28, a plurality of screen support ribs 206, extending inward from the wall of housing 202, in close proximity to inner wire 192 of axial filter screen 190, may insure that axial filter screen 190 and fiber bundle 198 are centered within housing 202, thus creating a uniform clearance space 208 within housing 202.

In FIG. 29, a first potting tool 210, comprising a first potting tool end 212, a first potting tool sleeve 214, and a slender potting tool arbor 216, may be prepared for use, by assembling an entry sleeve 218 all the way onto potting tool arbor 216, and attaching an arbor support 220 to the tip of potting tool arbor 216. All of these just-listed components may be axisymmetric.

First potting tool 210 may then be assembled onto housing 202, as illustrated in FIG. 29. As potting tool arbor 216, entry sleeve 218, and arbor support 220 pass through the center of fiber bundle 198, they may displace filter fibers radially outward so as to form what will become central void 232.

Second potting tool 222, comprising second potting tool end 224, and second potting tool sleeve 226, may then be assembled to housing 202. An arbor support recess 228 in second potting tool end may receive the tip of arbor support 220, for the purpose of centering and supporting the tip of potting tool arbor 216.

Referring now to FIG. 30, a potting material 230 may be injected into first potting tool 210, and may fill all free space, and all fiber interstitial space within first potting tool 210 and housing 202, to the level illustrated in FIG. 30. In a like manner, potting material 230 may be injected into second potting tool 222. The viscosity of the potting material 230, as it is injected, may be chosen such that the material enters the open fiber lumens only to a minimal distance. When potting material 230 is fully cured, first potting tool 210 and second potting tool 222 may be removed.

Referring now to FIG. 31, excess potting material 230, excess fiber bundle 198, a portion of inlet sleeve 218, and a portion of arbor support 220 may be cut back so that the surfaces of the remaining portions of the fibers and potting are flush with housing ends 204 of housing 202. This process re-exposes the lumens of the fibers in fiber bundle 198. Potting tool arbor 216, entry sleeve 218, and arbor support 220 displaced filter fibers radially outward, when they were inserted. Cured potting material 230 has now rendered the ends of fiber bundle 198 immobile, such that when potting tool arbor was removed, a central void 232 was left in fiber bundle 198.

The filter assemblage of FIG. 31 is now completed, ready for end caps to be added.

An inlet cap 234, having a blood inlet 236, an inlet tube 238, and a dialysate inlet 240 is assembled to housing 202, with inlet tube 238 inserted into inlet sleeve 214. Inlet cap 234 is bonded to housing 202 at inlet cap-housing joint 242. A seal may be established at inlet tube-entry sleeve joint 244 by adhesive bonding or by other suitable means.

An outlet cap 246, having a dialysate outlet 248, may be bonded to housing 202 at outlet cap-housing joint 250.

An outlet sleeve 256, having a blood outlet 252, may be positioned over outlet cap 246 and housing flange 254, and may be bonded along outlet sleeve-tube flange joint 262, and outlet sleeve-outlet cap joint 264.

A plurality of housing outlet ports 258, through the wall of housing 202, may connect outer clearance/collection space 208, of FIG. 28, to outlet channel 260, thence to blood outlet 252.

The completed cartridge is illustrated in FIG. 32.

In use, this fourth embodiment of an improved cartridge for dialysis or ultrafiltration receives a dialysate solution through dialysate inlet 240, and the dialysate solution then passes down through the lumens of the fibers of fiber bundle 198, and out through dialysate outlet 248. Blood from a patient is introduced through blood inlet 236, then flows through inlet tube 238 and inlet sleeve 218, into central void 232. From central void 232, blood flows more or less uniformly radially outward through the interstitial space in fiber bundle 198, passing through axial filter screen 190, into clearance space 208, then moving downward in clearance/collection space 208 to pass radially outward through housing outlet ports 258, into outlet channel 260. Blood then moves circumferentially in outlet channel 260 to blood outlet 252.

Further Comments

Although the various embodiments of the invention have been described in connection with blood flowing in the inter fiber space, it would also be possible to use embodiments of the invention in a more conventional system configuration in which blood flows in the fiber lumens and dialysate flows in the inter fiber space. Such an arrangement could achieve more uniform distribution of dialysate in the inter fiber space than is achieved in the prior art. Such improved dialysate flow distribution could have benefit in improving the magnitude and consistency of clearance provided by such dialyzers. It is known, in conventional hemodialysis, that nonuniform distribution of dialysate flowing in the inter fiber space does occur and can make the cartridge less efficient than would be the case for a more uniform flow distribution.

It is possible that design of embodiments of the invention could be further optimized by Computational Fluid Dynamics or by experimentation or by a combination of both methods. In general a goal of any such optimization can be to provide flow in the inter fiber space that is substantially uniform and has either no stagnation points or stagnation points that are as few and as small as possible.

The various embodiments of the invention could be used for dialysis or related therapy or generally for any therapy or modality. Void flow channels could be used with any type of orbital distributor, even if the geometry is not as illustrated in the first embodiment. Embodiments of the invention could be used for purposes other than the described cartridges that were intended for processing bodily fluids.

The ports of the cartridge could comprise Luer lock connectors for ports that are intended to handle blood, and could comprise Hansen style connectors for ports that are intended to handle dialysate, regardless of which compartment of the cartridge that is.

All cited references are incorporated by reference herein in their entirety. Features described herein may be combined in any combination. Steps of a method may be performed in any order that is physically possible. Although embodiments of the invention have been described herein, it is desired that the scope be limited only by the scope of the following claims.

We claim:

1. A cartridge for processing a fluid, said cartridge comprising:
    a housing that is generally tubular, having a housing wall, a first end, an opposite second end, and having a midplane located midway between the first end and the opposite second end;
    a plurality of fibers, at least some of said plurality of fibers being hollow and having porous walls or a semipermeable membrane, at least portions of said plurality of fibers being contained within said housing, said plurality of fibers being potted near their ends in a potting material,
    wherein said plurality of fibers are arranged as a bundle of fibers that are generally parallel to each other at said cartridge midplane of said housing, and wherein at said midplane of said housing, said plurality of fibers are substantially uniformly distributed throughout an interior region of said housing, and said plurality of fibers in said bundle of fibers having an average fiber-centerline-to-fiber-centerline spacing,
    wherein, said bundle of fibers contains at least one axial channel that is substantially open and has a transverse dimension that is at least 3 times said average fiber-centerline-to-fiber-centerline spacing, and
    wherein said cartridge has a potted region, and the at least one axial channel extends through said potted region from an outward-facing surface of said potted region to an opposed inward-facing surface of said potted region and the at least one axial channel is surrounded by the potting material in said potted region.

2. The cartridge of claim 1, wherein said cartridge contains a plurality of supply passageways, and at least some of said supply passageways are arranged at equal radial distances with respect to a longitudinal axis of said cartridge and are angularly spaced at equiangular intervals with respect to said longitudinal axis.

3. The cartridge of claim 1, wherein said at least one axial channel has the transverse dimension that is at least 5 times said average fiber-centerline-to-fiber-centerline spacing.

4. The cartridge of claim 1, wherein at said midplane of said cartridge, said fibers are distributed substantially uniformly across a cross-section of said housing taken perpendicular to a longitudinal direction of said housing.

5. The cartridge of claim 1, wherein said at least one axial channel is tapered in an axial direction, being wider near the potting material and narrower away from the potting material.

6. The cartridge of claim 1, wherein said at least one axial channel is tapered in an axial direction, being wider near said potting material and narrower closer to said midplane.

7. The cartridge of claim 1, wherein said plurality of fibers has a central porosity through said plurality of fibers near said midplane of said cartridge, and has a transitional porosity through said plurality of fibers further away from said midplane toward an end, and has an end porosity through said plurality of fibers adjacent to said potting material, and wherein said end porosity through said plurality of fibers is greater than said transitional porosity through said plurality of fibers, and said transitional porosity through said plurality of fibers is greater than said central porosity through said plurality of fibers.

8. A cartridge for processing a fluid, said cartridge comprising:
    a housing, having a housing wall comprising a housing wall first end and housing wall second end;
    a plurality of fibers, at least some of said plurality of fibers being hollow and having porous walls, at least portions of said plurality of fibers being contained within said housing, wherein said plurality of fibers are arranged as a bundle of fibers that are generally parallel to each other along a longitudinal axis, and wherein an inter fiber space is provided between said plurality of fibers, wherein the bundle of fibers have a bundle of fibers first end and a bundle of fibers second end, the bundle of fibers first end being embedded in a first potting material and the bundle of fibers second end being embedded in a second potting material, wherein fluid in said inter fiber space flows perpendicular to said bundle fibers and generally radially with respect to a longitudinal axis of said cartridge, wherein the bundle of fibers comprises a central void forming a channel that extends generally along the longitudinal axis between the first potting material and the second potting material for conducting the fluid in an axial direction until the fluid transitions to a radial direction through the inter fiber space, wherein the central void is surrounded by the plurality of fibers, wherein the housing and the bundle of fibers form a fluid collection space located radially outwardly of the bundle of fibers and radially inwardly of the housing, a first end cap on the housing wall first end and having a first port and a second port, the first port in communication with interiors of the bundle of fibers, and the second port being in communication with the central void via flow through the first potting material, a second end cap on the housing wall second end and having a third port in communication with the interiors of the plurality of fibers, and a fourth port in the housing wall in communication with the fluid collection space.

9. The cartridge of claim 8, wherein said first port comprises a blood inlet, and said second port comprises a blood outlet.

10. The cartridge of claim 8, wherein said central void extends from the first potting material to the second potting material.

11. A cartridge for processing a fluid, said cartridge comprising:
a housing, having a housing wall comprising a housing wall first end and a housing wall second end;
a plurality of fibers, at least some of said fibers being hollow and having porous walls, at least portions of said fibers being contained within said housing, wherein said plurality of fibers are arranged as a bundle of fibers that are generally parallel to each other along a longitudinal axis, and wherein an inter fiber space is provided between said plurality of fibers,
wherein the bundle of fibers have a bundle of fibers first end and a bundle of fibers second end, the bundle of fibers first end being embedded in a first potting material and the bundle of fibers second end being embedded in a second potting material,
a first end cap on the housing wall first end and having a first inlet, the first inlet in communication with interiors of the bundle of fibers,
a second end cap on the housing wall second end and having a first outlet in communication with the interiors of the bundle of fibers,
wherein said housing wall comprises a second inlet and a second outlet, said second inlet and said second outlet being located on opposite sides of the plurality of fibers and in line with each other so that fluid flowing in through said second inlet and out through said second outlet flows through said inter fiber space in a direction substantially perpendicular to said longitudinal axis of said cartridge.

12. The cartridge of claim 11, wherein said bundle of parallel fibers has a rectangular cross section.

13. The cartridge of claim 11, wherein said housing further comprises an inlet flow diverter downstream of the inlet port for distributing a fluid from the inlet port along the plurality of fibers.

14. The cartridge of claim 11, wherein said housing further comprises an outlet flow diverter upstream of the outlet port for distributing a fluid from the plurality of fibers to the outlet port.

15. A cartridge for processing a fluid, said cartridge comprising:
a housing, having a housing wall comprising a housing wall first end and a housing wall second end;
a plurality of fibers, at least some of said fibers being hollow and having porous walls, at least portions of said fibers being contained within said housing, wherein said plurality of fibers are arranged as a bundle of fibers that are generally parallel to each other along a longitudinal axis, and wherein an inter fiber space is provided between said plurality of fibers,
wherein the bundle of fibers have a bundle of fibers first end and a bundle of fibers second end, the bundle of fibers first end being embedded in a first potting material and the bundle of fibers second end being embedded in a second potting material,
a first end cap on the housing wall first end and having a first inlet, the first inlet in communication with interiors of the bundle of fibers,
a second end cap on the housing wall second end and having a first outlet in communication with the interiors of the bundle of fibers,
wherein said housing wall comprises a second inlet and a second outlet, said second inlet and said second outlet being located on opposite sides of the plurality of fibers so that fluid flowing in through said second inlet and out through said second outlet flows through said inter fiber space in a direction substantially perpendicular to said longitudinal axis of said cartridge,
wherein said bundle of parallel fibers has a rectangular cross section,
said housing further comprises an inlet flow diverter downstream of the second inlet for distributing a fluid from the second inlet along the plurality of fibers, and
an outlet flow diverter upstream of the second outlet for distributing a fluid from the plurality of fibers to the second outlet.

* * * * *